US012709757B2

(12) United States Patent
Shih et al.

(10) Patent No.: US 12,709,757 B2
(45) Date of Patent: Aug. 18, 2026

(54) PRODUCTION OF MILK OLIGOSACCHARIDES IN PLANTS

(71) Applicant: The Regents of the University of California, Oakland, CA (US)

(72) Inventors: Patrick M. Shih, Berkeley, CA (US); Collin Robert E. Barnum, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 106 days.

(21) Appl. No.: 18/805,564

(22) Filed: Aug. 15, 2024

(65) Prior Publication Data

US 2024/0401069 A1 Dec. 5, 2024

Related U.S. Application Data

(63) Continuation of application No. PCT/US2023/063730, filed on Mar. 3, 2023.

(60) Provisional application No. 63/316,945, filed on Mar. 4, 2022.

(51) Int. Cl.

| | |
|---|---|
| ***C12N 15/82*** | (2006.01) |
| ***C12N 15/52*** | (2006.01) |
| *C12N 9/10* | (2006.01) |
| *C12N 9/88* | (2006.01) |

(52) U.S. Cl.
CPC ......... *C12N 15/8243* (2013.01); *C12N 15/52* (2013.01); *C12N 9/1051* (2013.01); *C12N 9/88* (2013.01); *C12Y 204/01069* (2013.01); *C12Y 204/01274* (2013.01); *C12Y 402/01047* (2013.01)

(58) Field of Classification Search
CPC ...... C12N 15/8243; C12N 15/52; C12P 19/00
See application file for complete search history.

(56) References Cited

FOREIGN PATENT DOCUMENTS

| | | | |
|---|---|---|---|
| WO | 2022034067 | 2/2022 | |
| WO | WO-2022034067 A1 * | 2/2022 | ............ C08B 37/00 |

OTHER PUBLICATIONS

Biotech Updates. Scientists Genetically Engineer Plants to Produce Healthier Milk for Babies. 2024 (Year: 2024).*
Barnum et al (Engineered plants provide a photosynthetic platform for the production of diverse human milk oligosaccharides. Nature Food. p. 480-p. 491, 2024) (Year: 2024).*
Zeuner et al (Enzymatic transfucosylation for synthesis of human milk oligosaccharides. Carbohydrate Research. p. 1-22, 2020). (Year: 2020).*
Dasgupta (How many plant species are there in the world? Scientists now have an answer. Mongabay, 2016) (Year: 2016).*
International Search Report, Written Opinion, in priority application PCT/US2023/063730, 10 pages (Jul. 5, 2023).

* cited by examiner

*Primary Examiner* — Wayne Zhong
(74) *Attorney, Agent, or Firm* — Richard Aron Osman

(57) ABSTRACT

Mammalian milk oligosaccharides (MMO) are produced in plants engineered to express recombinant MMO biosynthetic pathways.

20 Claims, 5 Drawing Sheets

Specification includes a Sequence Listing.

2'FL

Intensity ($x10^5$)

6.0 5.0 4.0 3.0 2.0 1.0 0.0

10 11 12

Acquistion time (min)

PRODUCTION OF MILK OLIGOSACCHARIDES IN PLANTS

CROSS-REFERENCES TO RELATED APPLICATIONS

This application is a continuation of PCT/US23/63730, filed Mar. 3, 2023, which claims priority to U.S. Provisional Application No. 63/316,945, filed Mar. 4, 2022, the disclosures of which are hereby incorporated by reference in its entirety for all purposes.

GOVERNMENT SUPPORT CLAUSE

This invention was made with government support under Department of Energy award DEAC02-05CH11231. The government has certain rights in the invention.

REFERENCE TO A SEQUENCE LISTING

A Sequence Listing in XML format is incorporated by reference into the specification. The name of the XML file containing the Sequence Listing is B22-088-3US.xml. The XML file is 83,560 bytes and was created on Aug. 24, 2024.

INTRODUCTION

Human breast milk is a complete and comprehensive food perfectly evolved to nourish and protect infants. A key component to the distinct bioactive properties of breast milk is the presence of a wide diversity of human milk oligosaccharides (HMOs) that are well documented in establishing the nascent gut microbiota of infants to prevent diseases and ensure healthy development. Although commercial infant formulas have tried to replicate the biochemical properties of breast milk, these synthetic cocktails are unable to recapitulate the unique health benefits of breast milk due to an inability to produce the diversity of HMOs found in human milk at scale.

Currently, HMOs for infant formula have been largely produced via fermentation using engineered microbes; however, this approach is expensive and has been limited to the production of a small number of simple HMOs. Thus, there is great interest in developing new production hosts for HMOs. As such, plants serve as an attractive production platform, as they have an innate ability to generate a vast array of sugars and use them to produce complex oligosaccharide and polysaccharides. All HMOs can be grouped into three broad classes: neutral, fucosylated, and acidic. Here, we engineer plants to produce diverse sets of all three classes of HMOs (FIG. 1A). This includes the production of HMOs via transient expression and expression in stably transformed plants. Additionally, we increased accumulation of HMOs in plants through modulating nucleotide sugar pathways (FIG. 1B) to optimize the pool of substrate needed for HMO production. Finally, we demonstrate how plants can be used to make complex HMOs that have never before been produced through heterologous production, highlighting the advantages of engineering plants as an ideal production platform of HMOs.

SUMMARY OF THE INVENTION

For this invention we chose plants serve as a production platform, as they have an innate ability to generate a vast array of sugars and use them to produce complex oligosaccharide and polysaccharides. Mammalian milk oligosaccharide (MMOs) can be grouped into three broad classes: neutral, fucosylated, and acidic. We engineered plants to produce diverse sets of all three classes of MMOs (FIG. 1A). Additionally, we increased accumulation of MMOs in plants through modulating nucleotide sugar pathways to optimize the pool of substrate needed for MMO production (FIG. 1B). Finally, we demonstrated how plants can be used to make complex MMOs that have never before been produced through heterologous production. Our approach allows the production of complex human milk oligosaccharides at an agricultural scale, permitting high production. This enables the supplementation of infant formula with complex MMOs, provide researchers with complex MMOs to conduct research on their bioactivity, and treat diseases in adults.

The invention provides methods and compositions for plant production of mammalian (e.g. human) milk oligosaccharides.

In an aspect the invention provides a method of producing a mammalian milk oligosaccharide (MMO) in a plant, comprising growing a plant comprising and expressing a recombinant MMO biosynthetic pathway sufficient to produce the MMO.

In an aspect the invention provides a composition comprising a plant or plant part comprising and expressing a recombinant MMO biosynthetic pathway sufficient to produce the MMO.

In an aspect the invention provides a composition comprising an MMO isolated from a plant comprising and expressing a recombinant MMO biosynthetic pathway sufficient to produce the MMO.

In an aspect the invention provides a method of isolating an MMO comprising isolating the MMO from a plant comprising and expressing a recombinant MMO biosynthetic pathway sufficient to produce the MMO.

In embodiments the invention provides a plant, method or composition herein, wherein the plant is further comprising and expressing a eukaryotic (e.g. human) or prokaryotic (e.g. bacterial, such as *E. coli*) nucleotide sugar biosynthetic pathway sufficient to increase the production of the MMO.

In embodiments the invention provides a plant, method or composition herein, wherein the plant is further comprising and expressing a prokaryotic (e.g. bacterial, such as *E. coli*) nucleotide sugar biosynthetic pathway sufficient to increase the production of the MMO, wherein the use of a prokaryotic (as opposed to a eukaryotic) pathway substantially avoids pathway feedback inhibition in the plant.

In embodiments the invention provides a plant, method or composition herein, wherein the plant is further comprising and expressing a prokaryotic (e.g. bacterial, such as *E. coli*) nucleotide sugar biosynthetic pathway sufficient to increase the production of the MMO, wherein the pathway comprises one, two or three pathways (and corresponding enzymes):

a) GDP-fucose (ManA, ManB, ManC, Gmd, WcaG), b) UDP-galactose (pgi, pgm, GalU, GalE), and c) UDP-GlcNAc (glmS, glmM, glmU).

In embodiments the invention provides a plant, method or composition herein, wherein the MMO is of a mammal selected from human, cow and goat.

In embodiments the invention provides a plant, method or composition herein, wherein the MMO is a human milk oligosaccharide (HMO).

In embodiments the invention provides a plant, method or composition herein, the plant comprising and expressing a plurality of recombinant MMO biosynthetic pathways sufficient to produce a plurality (e.g. at least 2, 3, 4, 5, 6, 7, 8, 9 or 10) of different MMOs.

In embodiments the invention provides a plant, method or composition herein, wherein the plant is a dicot or monocot plant, such as tobacco, potato, tomato, sorghum, soybean, sugarcane, *Arabidopsis*, rice, sugar beet, wheat, cassava, and oat.

In embodiments the invention provides a plant, method or composition herein, further comprising isolating the resultant MMO from the plant.

In aspects and embodiments the invention provides:

a composition, plant or plant part herein, producing a mammalian milk oligosaccharide (MMO), comprising and expressing a recombinant MMO biosynthetic pathway sufficient to produce the MMO, wherein the pathway comprises recombinant enzymes:

- a β1-4 galactosyltransferase (β1-4-GalT; e.g. GalTPM1141), which glycosylates glucose using UDP-galactose to make lactose; and
- a β1-3 N-acetylglucosaminyltransferase (β1-3-GnT; e.g. NmLgtA) generates lacto-N-triose (LNTII) through the transfer of GlcNAC from UDP-GlcNAc to the galactose in the lactose; and at least one of:
- a β1-3-galactosyltransferase (β1-3-GalT; e.g. Cvβ3GalT) and a β1-4-GalT (e.g. HP0826 or NmLgtB), convert the LNTII to lacto-N-tetraose (LNT) and lacto-N-neotetraose (LNnT), respectively.

In aspects and embodiments the invention provides:

- a composition, plant or plant part herein, comprising and expressing of a β1-4-GalT (e.g. GalTPM1141), a β1-3-GlcNAcT (e.g. NmLgtA), a β1-4-GalT (e.g. HP0826 or NmLgtB), and a β1-3-GalT (e.g. Cvβ3GalT) (FIG. 1) to produce LNnT and LNT;
- a composition, plant or plant part herein producing non-fucosylated neutral MMOs (nMMOs, preferably nHMOs) comprising a lactose core with decorations of galactose and N-acetylglucosamine (GlcNAc);
- a composition, plant or plant part herein producing fucosylated MMOs (preferably HMOs), particularly comprising a lactose core decorated with one or more fucose moieties;
- a composition, plant or plant part herein comprising and expressing a β1-4-GalT (e.g. GalTPM1141), a β1-3-GlcNAcT (e.g. NmLgtA), a β1-4-GalT (e.g. HP0826 or NmLgtB), a β1-3-GalT (e.g. Cvβ3GalT) and a α1-2-fucosyltransferase (α1-2-FucT) (e.g. Te2FT) (FIG. 1) to produce lacto-N-fucopentaose I (LNFPI), a fucosylated pentasaccharide generated by the addition of an α-1,2-linked fucose to the terminal galactose in lacto-N-tetraose (LNT);
- a composition, plant or plant part herein, producing fucosyllactose, lacto-N-tetraose or lacto-N-neotetraose, and lacto-N-fucopentaose I (and particularly, 2'FL, LNT, LNnT and LNFPI) respectively (FIG. 3, Table 1);
- a composition, plant or plant part herein, wherein to improve LNFPI yields, nucleotide sugar biosynthetic pathways (FIG. 1B) are expressed to increase the availability of GDP-fucose (ManA, ManB, ManC, Gmd, WcaG), UDP-galactose (pgi, pgm, GalU, GalE), and UDP-GlcNAc (glmS, glmM, glmU) combinatorially (FIG. 4);
- a composition, plant or plant part herein, wherein when expressing the LNFP1 biosynthetic pathway (FIG. 1A) and the GDP-fucose biosynthetic pathway (FIG. 1B), there the plant metabolism harbors the innate ability to further glycosylate simple MMOs to create MMOs of higher complexity (such as lactodifucotetraose (LDFT) and lacto-N-difucohexaose I (LNDFHI); FIG. 3, Table 1). that have not been previously produced through any other heterologous hosts;
- a composition, plant or plant part herein, producing acidic MMOs, particularly comprising a lactose or nMMO core with one or more N-acetylneuraminic acid (Neu5Ac) moieties, comprising in the plant
- a mammalian CMP-Neu5Ac pathway, a UDP-GlcNAc pathway and aMMO biosynthetic genes resulting in production of aMMOs, particularly production of CMP-Neu5Ac;
- a plant herein, comprising and expressing a three gene bacterial pathway (neuA, neuB, neuC) or a four gene mammalian pathway (GNE, NANS, NMANP, CMAS) which utilize UDP-GlcNAc as a precursor for the production of CMP-Neu5Ac;
- a composition, plant or plant part herein, comprising and expressing a mammalian CMP-Neu5Ac pathway, GalTPM1141, NmLgtA, Cvβ3GalT, HpO826 (or NmnLgtB) and either PmSt3 or St6 (FIG. 1A) to produce 3'SL, 6'SL and isomers of LST;
- a composition, plant or plant part herein, that is a stable, transgenic plant, comprising constructs for the constitutive production of 2'FL and LNFPI (e.g. in stably transformed *N. benthamiana*); in embodiments, MMO10 (FIG. 6) contains genes for the four enzymes required to produce lactose, 2'FL, LNTII, LNT, and LNFPI connected via 2A peptides to allow multiple coding sequences to be driven by a single promoter, wherein each transcriptional unit is driven by a strong constitutive promoter to enable MMO production in all tissues, or MMO11 (FIG. 6), which contains a GDP-D-mannose-4,6-dehydratase (Gmd) from the GDP-fucose pathway, wherein both constructs provide the production of multiple MMOs, specifically 2'FL (FIG. 7) and LNFPI (FIG. 8);
- a method of producing a mammalian milk oligosaccharide (MMO) in a plant herein, comprising growing the plant comprising and expressing a recombinant MMO biosynthetic pathway sufficient to produce the MMO;
- a composition comprising an MMO isolated from a plant herein comprising and expressing a recombinant MMO biosynthetic pathway sufficient to produce the MMO;
- a food product composition comprising composition, plant or plant part (such as leaves, stems, roots, seeds, fruit or flowers) herein comprising and expressing a recombinant MMO biosynthetic pathway sufficient to produce the MMO.

The invention encompasses all combinations of the particular embodiments recited herein, as if each combination had been laboriously recited.

DESCRIPTION OF PARTICULAR EMBODIMENTS OF THE INVENTION

Plant Material

Figure 1A:
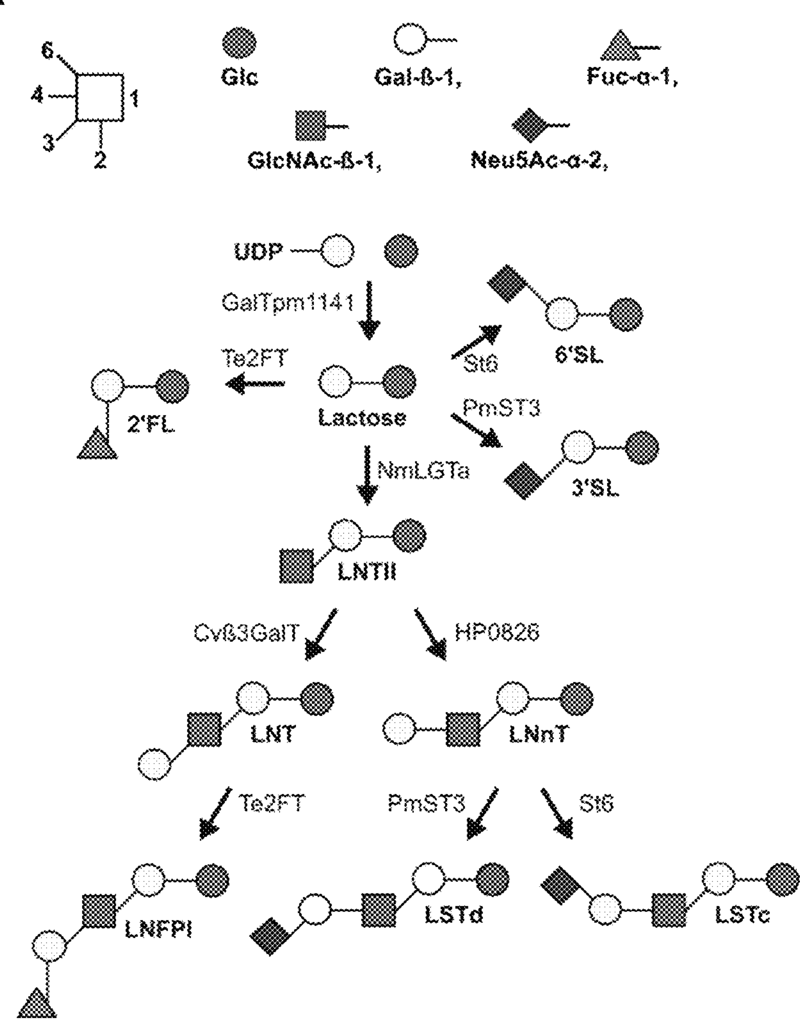
FIGS. 1A-B. A) MMO biosynthetic pathways used in this study. B) Nucleotide sugar biosynthetic pathways.

*Nicotiana benthamiana* was grown in 3.5 inch square pots in a controlled environment facility under a 12/12 day/night cycle (12 hours light, 12 hours dark) at ~100 μmol photons $m^{-2}$ $sec^{-1}$. Daytime temperatures were 26° C., and night temperatures were 25° C. Relative humidity was between 60-75%. Plants used in this study were 4 weeks old.

Cloning

Putative and known human milk oligosaccharide biosynthetic genes were either synthesized or acquired from other labs. Genes were PCR amplified. Amplified candidate genes were then cloned into the binary vector PMS057 using Golden Gate assembly, Gibson assembly, or standard digestion and ligation assembly. 2-4 μL of the assembly reactions were transformed into XL1B chemically competent *E. coli* cells via heat shock as previously described. Colonies were selected on LB agar plates containing 50 μg/mL kanamycin and sequence-verified using Sanger sequencing (McLab). Sequence verified plasmids were used to transform *Agrobacterium tumefaciens* str. GV3101 by electroporation as described by. Competent cells were then plated on LB agar plates containing 50 μg/mL rifampicin, 10 μg/mL gentamicin, 50 μg/mL kanamycin.

Transient Expression in *N. benthamiana*

Overnight cultures of *A. tumefaciens* str. GV3101 were grown in LB to an OD600 between 0.8 and 1.2. Cultures were centrifuged at 4000×G for 10 min and the supernatant was removed. Bacterial pellets were resuspended in infiltration media (10 mM $MgCl_2$, 10 mM MES, 500 μM acetosyringone, pH: 5.6). Following an hour incubation, *Agrobacterium* strains containing HMO biosynthetic genes were mixed in various combinations to a final OD600 of 0.5. *A. tumefaciens* strains were normalized to the level of the highest number of strains used in an experiment. For experiments that had less than the highest number of strains, an additional *A. tumefaciens* strain harboring the unrelated gene (dsRed) was added to reach a final OD600 of 0.5. An *A. tumefaciens* strain harboring the p19 silencing suppressor was used in all experiments at the same concentration as other strains. *A. tumefaciens* suspensions were syringe infiltrated into the abaxial side of the seventh leaf of 4-week old *N. benthamiana.*

Extractions

*N. benthamiana* leaves were harvested 5 days post-infiltration. Major veins of *N. benthamiana* were removed from the leaf tissue, and the tissue was frozen in liquid nitrogen before lyophilization. Lyophilized leaf tissue was bead beaten using a single steel bead at 20 Hz for 10 min.

Oligosaccharides were extracted from lyophilized leaf tissue by ethanol precipitation. To each sample, 1 mL of 80% ethanol was added before homogenization on a bead mill at 4 m/s for 1 min. Samples were then precipitated overnight at −20° C. and centrifuged at 10,000 rpm for 15 min. The supernatant was transferred to a 2 mL screw-cap tube. The pellet was washed twice by adding 500 μL of 80% ethanol, homogenizing via bead mill for 1 min, and centrifuging at 10,000 rpm for 15 min. The supernatant and washes were combined and dried in a vacuum centrifuge. Dried supernatants were reconstituted in 200 μL of water and subjected to both C18 and porous graphitized carbon (PGC) solid phase extractions (SPE) in 96-well plate format. C18 cartridges containing 25 mg of stationary phase were first conditioned by two additions of 250 μL of acetonitrile (ACN) followed by four additions of 250 μL water. Samples were then loaded and eluted with two volumes of 200 μL water. PGC cartridges containing 40 mg of stationary phase were conditioned by addition of 400 μL water, 400 μL 80% (v/v) ACN and water, followed by two volumes of 400 μL water. The sample eluate from C18 SPE was then loaded, washed thrice with 500 μL water, and eluted using two volumes of 200 μL 40% (v/v) ACN and water. The purified extracts were dried in a vacuum centrifuge and reconstituted in 100 μL of water before injecting 5 μL for liquid chromatography-mass spectrometry (LC-MS) analysis.

Initial chromatographic separation was carried out using a Thermo Scientific Vanquish UHPLC system equipped with a Waters BEH C18 Amide column (HILIC) (1.7 μm, 100 mm×2.1 mm). A 10 min binary gradient was employed based on Xu et al. (2017): 0.0-4.0 min: 25-35% A; 4.0-8.50 min, 35-65% A; 8.50-8.70 min: 25% A. Mobile phase A consisted of 3% ACN (v/v) in water with 0.1% formic acid, and mobile phase B consisted of 95% ACN (v/v) in water with 0.1% formic acid.

Chromatographic separation of oligosaccharides was carried out on an Agilent 1260 Infinity II LC equipped with a Hypercarb PGC column from Thermo Scientific (5 μm, 150 mm×1 mm). A 45 min binary gradient was employed: 0.00-2.50 min: 0.0-0.0% A; 2.50-15.00 min: 0.0-16.0% B; 15.00-20.00 min: 16.0-58.0% B; 20.00-22.00 min: 58.0-100.0% B; 22.00-28.00 min: 100.0-100.0% B; 28.00-30.00 min: 100.0-0.0% B; 30.00-40.00 min: 0.0-0.0% B. Solvent A consisted of 3% (v/v) ACN in water+0.1% formic acid and solvent B consisted of 90% (v/v) ACN in water+0.1% formic acid.

For identification of HMOs, a Thermo Scientific qExactive mass spectrometer equipped with an electrospray ionization source was operated in positive ionization mode with the following parameters: scan range=133.4-2000 m/z, spray voltage=2.5 |kV|, capillary temperature=320° C., aux gas heater temperature=325° C., sheath gas flow rate=25, aux gas flow rate=8, sweep gas flow rate=3. MS/MS analysis was performed using stepped collision energies of 20, 30, 40 [eV].

For quantification of LNFPI and HMO profiling, mass spectral analysis was carried out on an Agilent 6530 Accurate-Mass Q-TOF MS operated in positive mode using data dependent acquisition. The gas temperatures were held at 150° C. The fragmentor, skimmer, octopole, and capillary were operated at 70 V, 55 V, 750 V, and 1800 V, respectively. The collision energy was based on the empirically derived linear formula (1.8×m/z−3.6). The reference mass used for calibration was 922.009798 m/z. The Agilent MassHunter Qualitative software was used for data analysis. Oligosaccharides were identified using an in-house library, their MS/MS spectra, and comparison to either authenticated standards or a pool of human milk oligosaccharides of known composition. The reference mass used for calibration was 922.009798 m/z.

Results

Production of Neutral HMOs

Non-fucosylated neutral HMOs (nHMOs) are composed of a lactose core with various decorations of galactose and N-acetylglucosamine (GlcNAc). nHMOs are the most abundant class of HMOs in breast milk, comprising 42-55% of HMOs (Totten et al., 2012). While nHMOs provide various health benefits, they also serve as the core scaffold for the production of various complex HMOs.

Figure 1B:
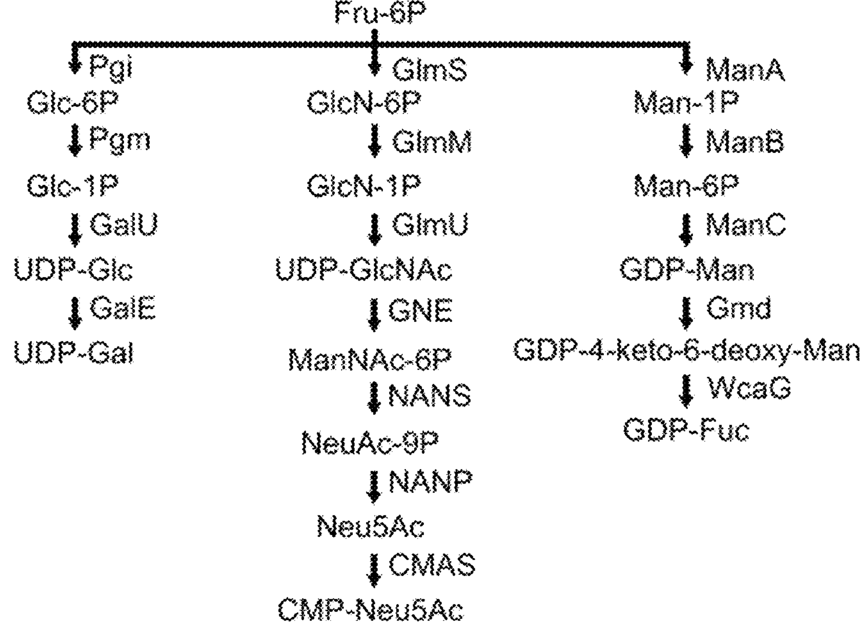
Figure 2:
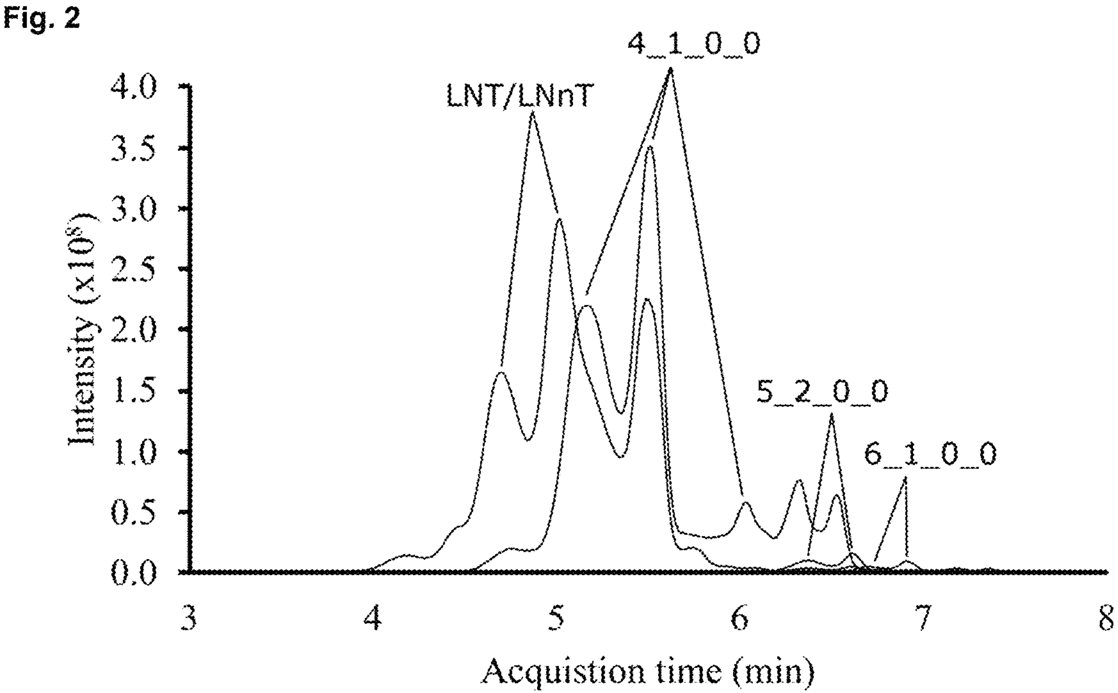
FIG. 2. Production of neutral MMOs in planta. Extracted mass chromatogram identifying the in planta production of Lacto-N-tetraose/Lacto-N-neotetraose (LNT/LNnT), 4_1_0_0, 5_2_0_0 and 6_1_0_0. Data collected using liquid chromatography-MS with a HILIC column. Numbered codes refer to the number of Hexose_HexNAc_Deoxyhexose_N-acetylneuraminic acid saccharides in the oligosaccharide as determined by MS/MS fragmentation.

To produce nHMOs, lactose is first made by a β-1,4-galactosyltransferase, GalTPM1141, which glycosylates glucose using UDP-galactose (Parschat et al., 2020). Following lactose production, a β-1,3-N-acetylglucosaminyltransferase, NmLgtA, generates lacto-N-triose (LNTII) through the transfer of GlcNAC from UDP-GlcNAc to the galactose in lactose (McArthur et al., 2019). LNTII serves as a branch point for the production of various complex HMOs that can be further modified to generate large, complex HMOs. LNTII can then be used to generate lacto-N-tetraose (LNT) and lacto-N-neotetraose (LNnT), using β-1,3-galactosyltranserase, Cvβ3GalT, and a β-1,4-galactosyltransferase (e.g. HP0826 or NmLgtB), respectively (Fang et al., 2018; McArthur et al., 2019). Expression of GalTPM1141, NmLgtA, HP0826 (or NmLgtB), and Cvβ3GalT (FIG. 1) results in the production of ions with a m/z of 708.2565 and 708.2568 corresponding to LNnT and LNT respectively (FIG. 2, Table 1). Analysis using HILIC and PGC chromatography with analytical standards, retention time and MS/MS fragmentation further validated the identification of these structures, demonstrating the ability of plants to make nHMOs. Additionally, neutral HMOs with a higher degree of polymerization composed of 4 hexose sugars/1 hexNAc sugar, 5 hexose sugars/2 hexNAc sugars, and 6 hexose sugars/1 hexNAc were identified (FIG. 2, Table 1). These ions had values for m/z of 870.3091, 1235.4430, and 1194.4120, respectively. This displays the ability of plants to create HMOs with a high degree of polymerization.

Production and Optimization of Fucosylated HMOs

Fucosylated HMOs (fHMOs) are a key component of breast milk and are characterized by the presence of a lactose or nHMO core decorated with one or more fucose moieties. While their abundance is dependent on the genotype of the mother, they are estimated to account for 35-50% of HMOs found in breast milk (Totten et al., 2012). fHMOs are of particular interest as they have distinct bioactivities from other HMOs. 2'-fucosyllactose (2'FL) is one of the most abundant HMOs found in human breast milk. Microbial production is currently able to produce 2'FL at a commercial scale; however, production of larger, abundant fHMOs such as lactodifucotetraose (LDFT), lacto-N-difucohexaose (LNDFH) and lacto-N-fucopentaose (LNFP) has not been possible at a commercial scale.

Figure 3:
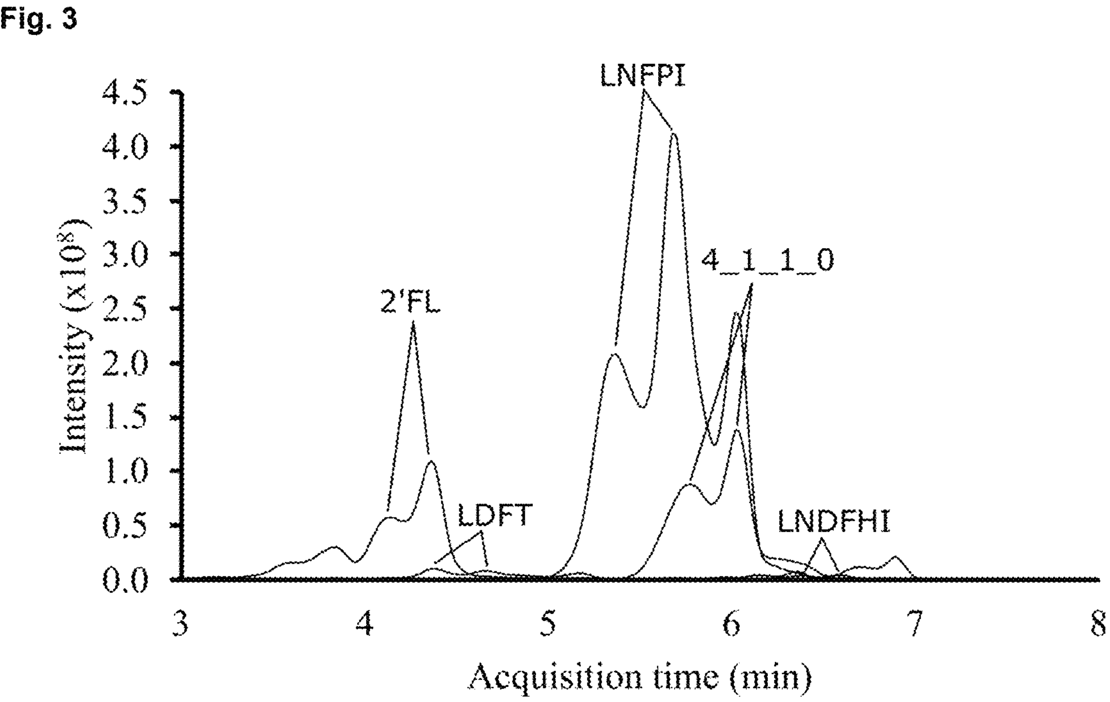
FIG. 3. Production of fucosylated MMOs in planta. Extracted ion chromatogram identifying the in planta production of 2'-fucosyllactose (2'FL), lacto-N-fucopentaose I (LNFPI), lactodifucotetraose (LDFT), lacto-N-difucohexaose I (LNDFHI), and 4_1_1_0. Data collected using liquid chromatography-mass spectrometry with a HILIC column. Numbered codes refer to the number of Hexose_HexNAc_Deoxyhexose_N-acetylneuraminic acid saccharides in the oligosaccharide as determined by MS/MS fragmentation.
Figure 4A:
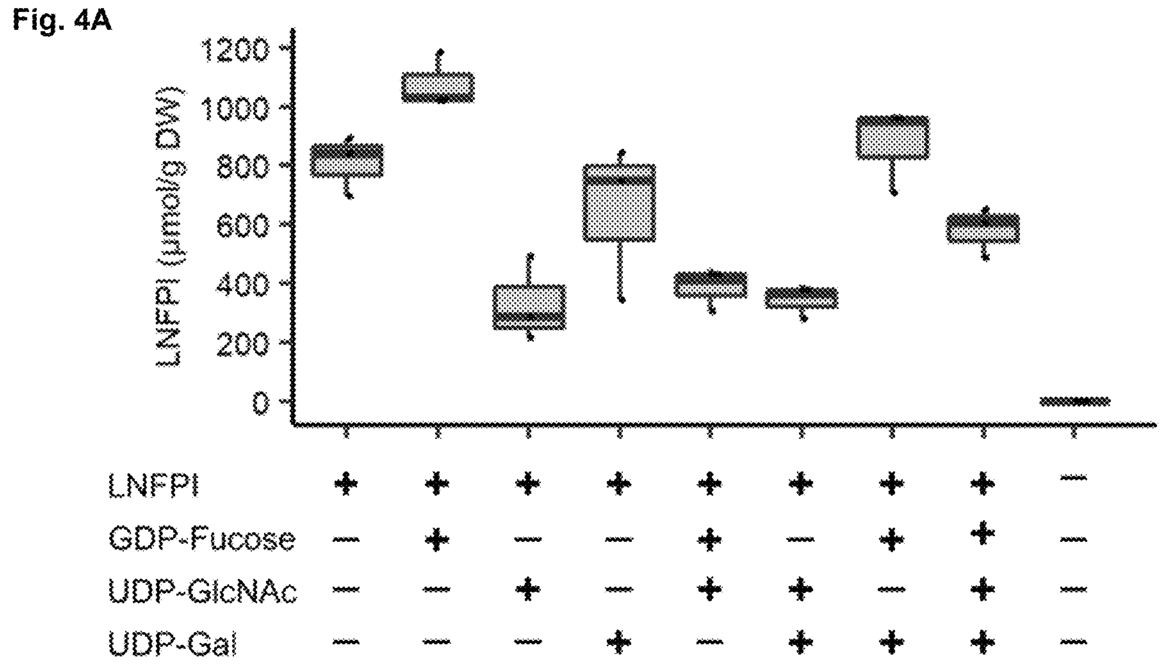
FIGS. 4A-B. Optimization of fucosylated MMO production. A) Quantification of LNFPI produced when expressing the LNFPI and nucleotide sugar biosynthetic pathways. B) Oligosaccharide profiles of leaf tissue expressing various nucleotide sugar biosynthetic pathways. Negative control produces negligible amounts of oligosaccharides compared to experimental samples. Hexose, HexNAc and deoxyhexose refer to the presence of at least one hexose sugar, N-acetylhexosamine sugar, and deoxyhexose sugar, respectively.

Lacto-N-fucopentaose I (LNFPI) is a fucosylated pentasaccharide generated by the addition of an α-1,2-linked fucose to the terminal galactose in lacto-N-tetraose (LNT). To produce LNFPI, we transiently expressed GalTPM1141, NmLgtA, Cvβ3GalT, HP0826 and Te2FT in *N. benthamiana* (FIG. 1). The expression of this pathway alone resulted in the production of an ions with m/z of 489.1824, 708.2568, 708.2565 and 854.3150, corresponding to fucosyllactose, lacto-N-tetraose or lacto-N-neotetraose, and lacto-N-fucopentaose I, respectively (FIG. 3, Table 1). Analysis using HILIC and PGC chromatography with analytical standards, retention time and MS/MS fragmentation identified these structures as 2'FL, LNT, LNnT and LNFPI (Table 1). Leaves expressing the LNFPI pathway produced LNFPI at a concentration of 809 μg/g DW (FIG. 4A). To improve LNFPI yields, nucleotide sugar biosynthetic pathways (FIG. 1B) were expressed to increase the availability of GDP-fucose (ManA, ManB, ManC, Gmd, WcaG), UDP-galactose (pgi, pgm, GalU, GalE), and UDP-GlcNAc (glmS, glmM, glmU) combinatorially (FIG. 4). The highest LNFPI yields were obtained by the expression of the GDP-fucose pathway with the LNFPI pathway, reaching a concentration of 1075 μg/g DW (1.33-fold improvement) (FIG. 4A). The increased yield following the expression of the GDP-fucose pathway suggests that native GDP-fucose levels are limiting (FIG. 4A); thus, our pathway engineering efforts demonstrate a metabolic strategy to address this bottleneck and improve overall yields of fHMOs like LNFPI.

Figure 4B:
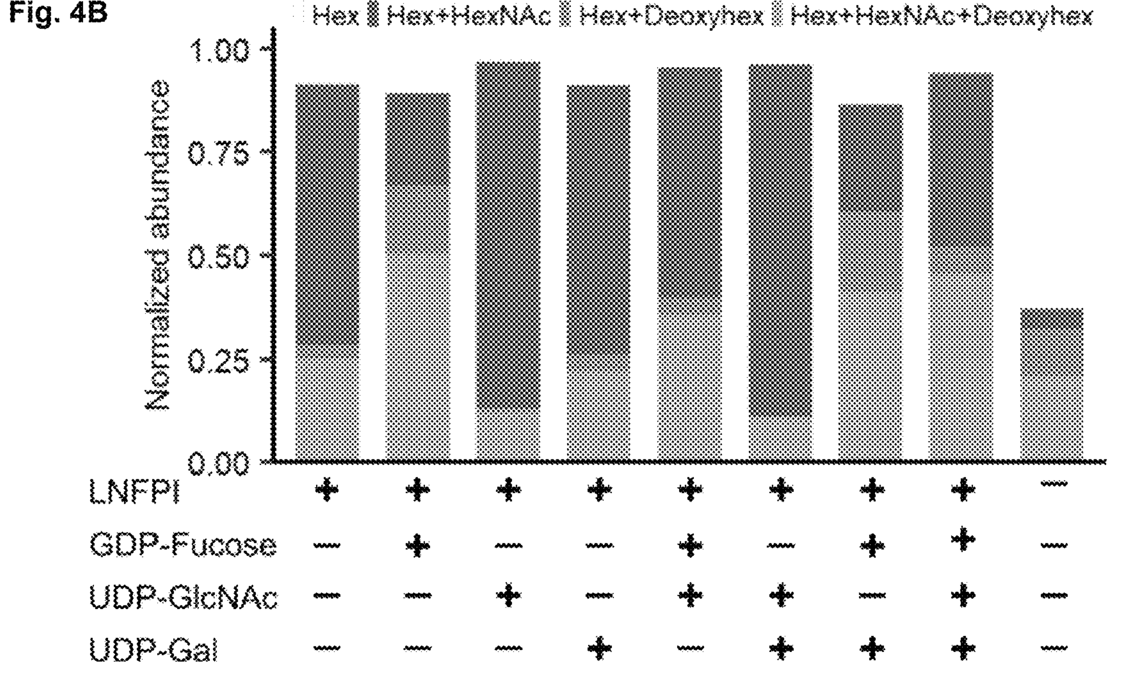

HMO composition was also affected by changes in nucleotide sugar levels. Expression of the GDP-fucose pathway dramatically increased the relative amounts of oligosaccharides containing a deoxyhexose moiety, which likely corresponds to an increased abundance of fucosylated oligosaccharides (FIG. 4B). Expression of the UDP-GlcNAc pathway increased the relative amounts of oligosaccharides containing at least one hexose and one N-acetylhexosamine (hexNAc) (FIG. 4B). Together, these results display our ability to generate neutral and fucosylated HMOs in a single leaf and alter HMO composition by overexpression of various nucleotide sugar biosynthetic pathways.

In addition to producing the expected HMOs when expressing the LNFP1 biosynthetic pathway (FIG. 1A) and the GDP-fucose biosynthetic pathway (FIG. 1B), we identified the unanticipated production of two additional ions of m/z 635.2411 and 1000.3700. Analysis using HILIC and PGC chromatography with analytical standards, retention time and MS/MS fragmentation, the ion with m/z 635.2411 was identified as the HMO, lactodifucotetraose (LDFT), and the ion with m/z 1000.3700 was identified as the HMO, lacto-N-difucohexaose I (LNDFHI) (FIG. 3, Table 1). Since none of the enzymes used in this pathway are reported to have either α-1,3- or α-1,4-fucosyltransferase activity, we suspect that these additional glycosylations are products of endogenous plant enzymes; thus demonstrating some of the natural unanticipated advantages of using plants as a chassis for the production of HMOs. The discovery that plants have enzymes to fill in the last steps involved in making HMOs such as LDFT and LNDFHI highlight how plants may serve as a more attractive host for production of HMOs than current microbial platforms. Specifically, plant metabolism harbors the innate ability to further glycosylate simple HMOs to create HMOs of higher complexity that have not been previously produced through any other heterologous hosts.

Production of Acidic HMOs

Acidic HMOs (aHMOs) are a class of HMO characterized by the presence of a lactose or nHMO core with one or more N-acetylneuraminic acid (Neu5Ac) moieties. aHMOs represent a structurally diverse class of HMOs, accounting for 12-14% of HMOs found in human breast milk (Totten et al., 2012). While aHMOs are not currently commercially available, simple aHMOs, such as 3'-sialyllactose (3'SL) and 6'-sialyllactose (6'SL), have been produced in *E. coli* (Ruffing & Chen, 2006); however, microbial systems have been unable to produce larger aHMOs, such as isomers of sialyl-lacto-N-tetraose (LST), To overcome this limitation, we sought to produce both simple and complex aHMOs using transient expression in *N. benthamiana.*

Since plants do not natively produce CMP-Neu5Ac, we tested a three gene bacterial pathway (neuA, neuB, neuC) and a four gene mammalian pathway (GANE, NANS, NANP, CMAS) which utilize UDP-GlcNAc as a precursor for the production of CMP-Neu5Ac (Castilho et al., 2008; Vimr et al., 2004). Expression of the bacterial CMP-Neu5Ac pathway and aHMO biosynthetic genes did not produce any aHMOs. Expression of the mammalian CMP-Neu5Ac pathway, UDP-GlcNAc pathway and aHMO biosynthetic genes resulted in the successful production of aHMOs, displaying the successful production of CMP-Neu5Ac.

Figure 5:
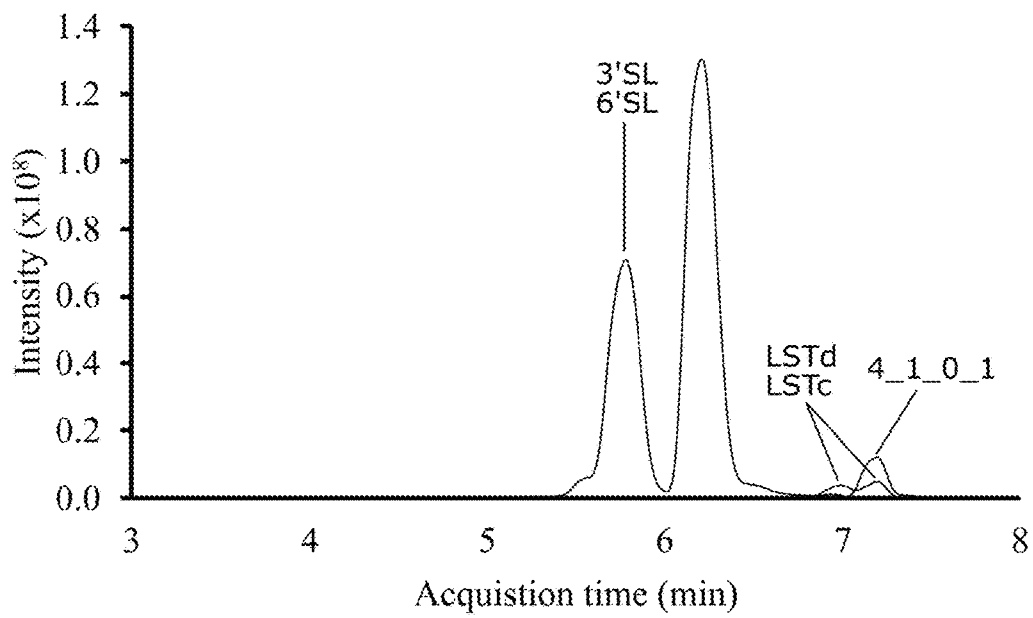
FIG. 5. Production of neutral MMOs in planta. Extracted ion chromatogram identifying the in planta production of 3'-sialyllactose (3'SL), 6'-sialyllactose (6'SL), sialyllacto-N-neotetraose d (LSTd), sialyllacto-N-neotetraose c (LSTc), and 4_1_0_1. Data was collected using liquid chromatography-mass spectrometry with a HILIC column. Numbered codes refer to the number of Hexose_HexNAc_Deoxyhexose_N-acetylneuraminic acid saccharides in the oligosaccharide as determined by MS/MS fragmentation.

Simple aHMOs, such as 3'SL and 6'SL, are produced through the α2-3 or α2-6 sialylation of lactose. LST is a complex pentasaccharide aHMO with multiple isomers. Production of LST requires the production of Lacto-N-neotetraose (LNnT) and its subsequent addition of an α-2,6-linked or α-2,3-linked Neu5Ac. To produce 3'SL, 6'SL and isomers of LST, we expressed a mammalian CMP-Neu5Ac pathway, GalTPM1141, NmLgtA, Cvβ3GalT, Hp0826 (or NmLgtB) and either PmrS3 or St6 (FIG. 1A). Following HILIC LC-MS analysis a peak was identified for m/z 634,2189, indicating sialyllactose was present (FIG. 5). Further analysis using PGC chromatography with analytical standards, retention time and MS/MS fragmentation indicates the presence of two sialyllactose isomers, corresponding to 3'SL and 6'SL (FIG. 5, Table 1). Multiple peaks are also present for m/z 999.3483, indicating the production of LST. Further analysis using PGC chromatography with analytical standards, retention time, and MS/MS fragmentation indicate the production of LSTc and LSTd in planta (FIG. 5, Table 1). This is especially notable, as this is the first successful production of LST in a heterologous host.

The production of 3'SL, 6'SL, LNnT, LNT, and multiple isomers of LST in a heterologous host has never been described before. Additionally, this is the first demonstration of producing LST isomers in a heterologous host, displaying the utility of plants as a platform. The production of aHMOs will serve as a starting point for the production of HMOs decorated with both fucose and Neu5Ac moieties.

Production of HMOs in Stably Transformed Plants

Figure 6:
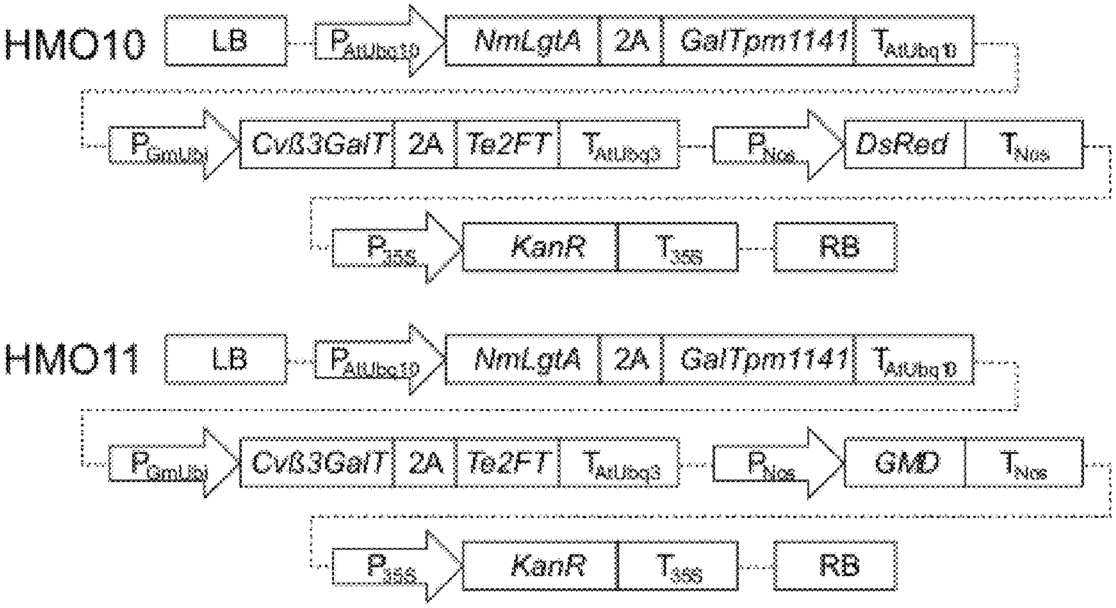
FIG. 6. Constructs used in the generation of stably transformed *N. benthamiana.*
Figures 7, 8:
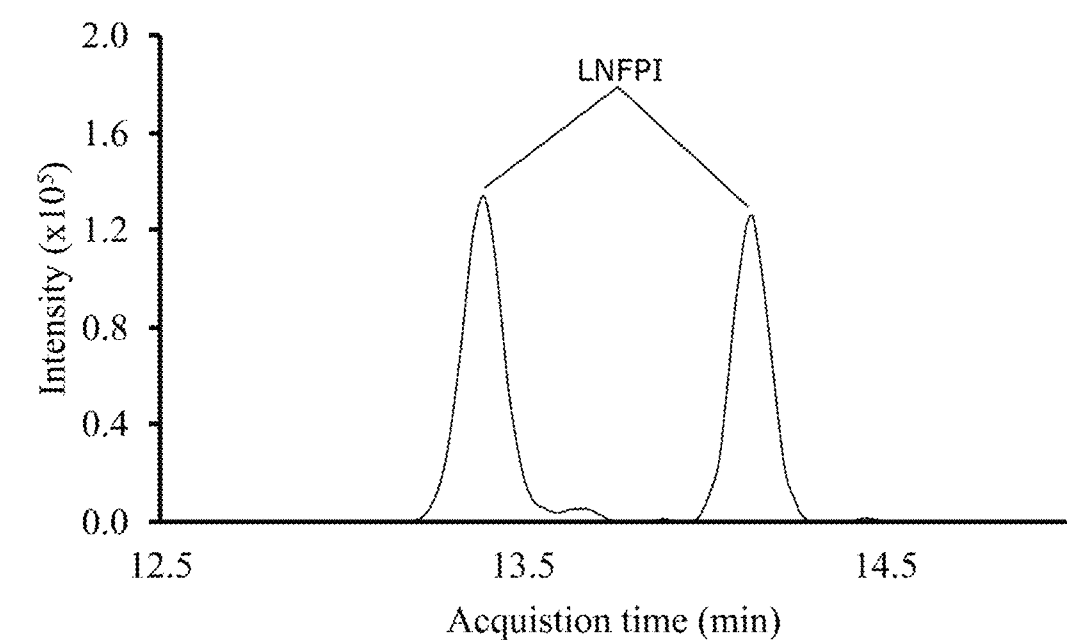
FIG. 7. Identification of 2'-fucosyllactose (2'FL) produced in stably transform *N. benthamiana*. Data was collected using liquid chromatography-mass spectrometry with a porous graphitic carbon column.
FIG. 8. Identification of lacto-N-fucopentaose I (LNFPI) produced in stably transform *N. benthamiana*. Data was collected using liquid chromatography-mass spectrometry with a porous graphitic carbon column.

To test the ability of stable transgenic plants to produce HMOs, we generated two constructs for the constitutive production of 2'FL and LNFPI in stably transformed *N. benthamiana*. HMO10 (FIG. 6) contains genes for the four enzymes required to produce lactose, 2'FL, LNTII, LNT, and LNFPI connected via 2A peptides to allow multiple coding sequences to be driven by a single promoter. Each transcriptional unit is driven by a strong constitutive promoter to enable HMO production in all tissues. To explore the effects of overexpressing portions of the GDP-fucose pathway, we also generated stable lines expressing HMO11 (FIG. 6), which contains a GDP-D-mannose-4,6-dehydratase (Gmd) from the GDP-fucose pathway. Both constructs enabled the production of multiple HMOs, specifically 2'FL (FIG. 7) and LNFPI (FIG. 8).

REFERENCES

Castilho, A., et al. (2008). Construction of a Functional CMP-Sialic Acid Biosynthesis Pathway in *Arabidopsis. Plant Physiology,* 147(1), 331-339.

Fang, J.-L., Tsai, T.-W., Liang, C.-Y., Li, J.-Y., & Yu, C.-C. (2018). Enzymatic Synthesis of Human Milk Fucosides α1,2-Fucosyl para-Lacto-N-Hexaose and its Isomeric Derivatives. *Advanced Synthesis & Catalysis,* 360(17), 3213-3219. https://doi.org/10.1002/adsc.201800518

McArthur, J. B., Yu, H., & Chen, X. (2019). A Bacterial β1-3-Galactosyltransferase Enables Multigram-Scale Synthesis of Human Milk Lacto-N-tetraose (LNT) and Its Fucosides. *ACS Catalysis,* 9(12), 10721-10726. https://doi.org/10.1021/acscatal.9b03990

Parschat, K., et al. (2020). High-Titer De Novo Biosynthesis of the Predominant Human Milk Oligosaccharide 2'-Fucosyllactose from Sucrose in *Escherichia coli. ACS Synthetic Biology,* 9(10), 2784-2796. https://doi.org/10.1021/acssynbio.0c00304

Ruffing, A., & Chen, R. R. (2006). Metabolic engineering of microbes for oligosaccharide and polysaccharide synthesis. *Microbial Cell Factories,* 5(1), 25. https://doi.org/10.1186/1475-2859-5-25

Totten, S. M., et al. (2012). Comprehensive Profiles of Human Milk Oligosaccharides Yield Highly Sensitive and Specific Markers for Determining Secretor Status in Lactating Mothers. *Journal of Proteome Research,* 11(12), 6124-6133. https://doi.org/10.1021/pr300769g Virnr, E. R., et al. (2004). Diversity of Microbial Sialic Acid Metabolism. *Microbiology and Molecular Biology Reviews*. https://doi.org/10.1128/MMBR.68.1.132-153.2004

Xu, G, et al. (2017). Absolute quantitation of human milk oligosaccharides reveals phenotypic variations during lactation. *The Journal of Nutrition,* 147(1), 117-124.

Unless contraindicated or noted otherwise, in these descriptions and throughout this specification, the terms "a" and "an" mean one or more, the term "or" means and/or. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

| Name | Hex | HexNAc | Deoxyhex | Neu5Ac | Enzymes | m/z (exptl) | Retention time (min) | MS/MS (top 3) |
|---|---|---|---|---|---|---|---|---|
| 2'FL* | 2 | 0 | 1 | 0 | GalTpm1141, NmLgtA, Cvβ3GalT, Te2FT, ManA, ManC, Gmd, WcaG | 489.1824 | 10.97 | N/A |
| 3'SL* | 2 | 0 | 0 | 1 | GalTpm1141, NmLgtA, Hp0826, PmSt3, GNE, NANS, NANP, CMAS | 634.2183, 634.2189 | 17.18, 17.85 | 163.0604, 274.0928, 292.1034 |
| 6'SL* | 2 | 0 | 0 | 1 | GalTpm1141, NmLgtA, Cvβ3Gal, Hp0826, St6, GNE, NANS, NANP, CMAS | 634.2197, 634.2002 | 13.40, 14.61 | N/A |
| LNT* | 3 | 1 | 0 | 0 | GalTpm 1141, NmLgtA, Cvβ3GalT | 708.2568, 708.2571 | 14.33, 13.95 | 186.0765, 204.0872, 366.1404 |
| LNnT* | 3 | 1 | 0 | 0 | GalTpm1141, NmLgtA, Hp0826 | 708.2565 | 14.29 | 138.0553, 168.0659, 366.1404 |
| LSTc* | 3 | 1 | 0 | 1 | GalTpm1141, NmLgtA, Cvβ3Gal, Hp0826, St6, GNE, NANS, NANP, CMAS | 999.3483 | 18.21 | N/A |
| LSTd* | 3 | 1 | 0 | 1 | GalTpm1141, NmLgtA, Hp0826, PmSt3, GNE, NANS, NANP, CMAS | 999.3484 | 19.37 | N/A |
| LNFPI* | 3 | 1 | 1 | 0 | GalTpm1141, NmLgtA, Cvβ3GalT, Te2FT, ManA, ManC, Gmd, WcaG | 854.3150, 854.3159, | 13.15, 13.91 | 204.0872, 366.1404, 512.1996 |
| LDFT* | 2 | 0 | 2 | 0 | GalTpm 1141, NmLgtA, Cvβ3GalT, Te2FT, ManA, ManC, Gmd, WcaG | 635.2411 | 10.73 | N/A |
| LNDFHI* | 4 | 1 | 2 | 0 | GalTpm1141, NmLgtA, Cvβ3GalT, Te2FT, ManA, ManC, Gmd, WcaG | 1000.3700, 1000.3750 | 10.23, 10.62 | N/A |
| 4100 | 4 | 1 | 0 | 0 | GalTpm1141, NmLgtA, Cvβ3Gal, Hp0826 | 870.3091 | 17.40, 17.70 | 204.0872, 366.1404, 528.1935 |
| 5200 | 5 | 2 | 0 | 0 | GalTpm1141, NmLgtA, Cvβ3Gal, Hp0826 | 1235.443 | 18.15 | 366.1404, 731.2735, 1235.4497 |
| 6100 | 6 | 1 | 0 | 0 | GalTpm1141, NmLgtA, Cvβ3Gal, Hp0826 | 1194.4120, 1194.4130 | 18.51, 18.71 | 204.0872, 366.1404, 690.2472, |
| 4000 | 4 | 0 | 0 | 0 | GalTpm1141, NmLgtA, Cvβ3Gal, Hp0826 | 667.2294 | 17.5 | 163.0606, 325.1144, 630.7106 |
| 4101a | 4 | 1 | 0 | 1 | GalTpm1141, NmLgtA, Hp0826, PmSt3, GNE, NANS, NANP, CMAS | 1161.403 | 19.8 | 366.1406, 292.1034, 657.2365 |
| 4101b | 4 | 1 | 0 | 1 | GalTpm1141, NmLgtA, Hp0826, PmSt3, GNE, NANS, NANP, CMAS | 1161.402 | 20.61 | 366.1405, 292.1036, 657.2365 |
| 4101c | 4 | 1 | 0 | 1 | GalTpm1141, NmLgtA, Cvβ3GalT, PmSt3, GNE, NANS, NANP, CMAS | 1161.403 | 19.89 | 366.1406, 292.1041, 657.2370 |
| 4110a | 4 | 1 | 1 | 0 | GalTpm1141, NmLgtA, Cvβ3GalT, Te2FT, ManA, ManC, Gmd, WcaG | 1016.365 | 14.66 | 204.0872, 366.1403, 512.1988 |
| 4110b | 4 | 1 | 1 | 0 | GalTpm 1141, NmLgtA, Cvβ3GalT, Te2FT, ManA, ManC, Gmd, WcaG | 1016.365 | 15 | 204.0874, 366.1396, 512.1982 |
| 4110c | 4 | 1 | 1 | 0 | GalTpm1141, NmLgtA, Cvβ3GalT, Te2FT, ManA, ManC, Gmd, WcaG | 1016.365 | 16.57 | 366.1404, 204.0872, 512.1989 |

Table 1. Chromatographic retention time and mass spectrum peaks of HMOs identified using liquid chromatography-mass spectrometry with a porous graphitic carbon column. * denotes identification with an authenticated standard.
HMO Gene Sequences: Gene Name, Accession, Nucleotide and Amino Acid Sequence

```
GalTpm1141 AEC04686
                                                        (SEQ ID NO: 1)
ATGCCCATGACGAACTACGTAATATCACTAAGTTCAGCCAGAGAGCGTAGGCGTCATGT

GATGAACGAATTTTCCAAGCACCACGTTCCATTCCAGTTCTTCGACGCAGTTTCACCATCTTCT

CAGCTGGATTTCCTCATTCAAAGACTTGTGCCTAACCTTAACGGAACAAGCCTTACAGGTGGAG

AGAAAGGGTGCCTTATCTCACATGTGGCCTTATGGCATAAGTGCATACAAGACAATCTGCCATA

TATAGCAATCTTCGAAGATGACATACTCCTTGGCAGGGACGCCCGTGCCTTCTTGGCAGAGGAC

GAGTGGCTATTCTCTCGATTCAACTGTGACGATATCTTCATTATCAGACTGGAAACTTTTCTTC

AGGAAACTATCTGCGAAGCGCTCCCCAACCCCGTGTCATATTGCGGCAGGGACTTCTTGGCACT

TAAAGATGAACACCTTGGGACGGCTGGTTATATCATTTCACTTGGGGCCGCCAAATATTTATTG

GAAATCTTTAAGAACATGGAGAGTAACAACATTTTCCCAATCGACCACTTGATTTTCAATCGTT

TCTTAGCGGGTGAAGAACTGATGGTTTACCAGCTATCTCCTGCTCTGTGCATTCAAGAGCTTCA

ATTGAACGAAAACGAGTCTTTGTTGGACAGCCAACTTGAGTCCGAACGCAAGAACTATCGTCTT

GCTGAGAAGGCTAGAAAGAAGAAAACCTGGCGTGAAAAGGTTTACCACATCTTCACAAAGCCAC

AAAGAATGCTTAAGAAAAGAAAGGAAAGGGCTGAGAAGAATGCCAAAATGAAACTCAAATGCAT

CGTCAAATTCGAGTAA

                                                        (SEQ ID NO: 2)
MPMTNYVISLSSARERRHVMNEFSKHHVPFQFFDAVSPSSQLDFLIQRLVPNLNGTSL

TGGEKGCLISHVALWHKCIQDNLPYIAIFEDDILLGRDARAFLAEDEWLFSRENCDDIFIIRLE

TFLQETICEALPNPVSYCGRDFLALKDEHLGTAGYIISLGAAKYLLEIFKNMESNNIFPIDHLI

FNRFLAGEELMVYQLSPALCIQELQLNENESLLDSQLESERKNYRLAEKARKKKTWREKVYHIF

TKPQRMLKKRKERAEKNAKMKLKCIVKFE*

NmLgtA AAC44084.1
                                                        (SEQ ID NO: 3)
ATGCAGCCTTTAGTCAGCGTATTGATTTGCGCCTACAACGTAGAAAAATATTTCGCCCA

ATCATTAGCCGCCGTCGTGAATCAAACTTGGTGCAACTTGGATATTTTGATTGTCGATGACGGC

TCGACAGACGGTACGCTTGCCATTGCCAAGGATTTTCAAAAGCGGGACAGCCGTATCAAAATCC

TTGCACAAGCTCAAAATTCCGGCCTGATTCCCTCTTTAAACATCGGGCTGGACGAATTGGCAAA

GTCGGGGGGGGGGGAATATATTGCACGCACCGATGCCGACGATATTGCCGCCCCCGACTGGATT

GAGAAAATCGTGGGCGAGATGGAAAAAGACCGCAGCATCATCGCGATGGGCGCGTGGCTGGAAG

TGTTGTCGGAAGAAAAGGACGGCAACCGGCTGGCGCGGCATCACAGGCACGGCAAAATTTGGAA

AAAGCCGACCCGACACGAAGATATTGCCGACTTTTTCCCTTTCGGCAACCCCATACACAACAAC

ACGATGATTATGAGGCGCAGCGTCATTGACGGCGGTTTGCGTTACAACACCGAGCGGGATTGGG

CGGAAGATTACCAATTTTGGTACGATGTCAGCAAATTGGGCAGGCTGGCTTATTATCCCGAAGC

CTTGGTCAAATACCGCCTTCACGCCAATCAGGTTTCATCCAAATACAGCATCCGCCAACACGAA

ATCGCGCAAGGCATCCAAAAAACCGCCAGAAACGATTTTTTGCAGTCTATGGGTTTTAAAACCC

GGTTCGACAGCCTTGAATACCGCCAAATAAAAGCAGTAGCGTATGAATTGCTGGAGAAACATTT
```

-continued

GCCGGAAGAAGATTTTGAACGCGCCCGCCGGTTTTTGTACCAATGCTTCAAACGGACGGACACG

CCGCCCGCCGGCGCGTGGCTGGATTTTGCGGCAGACGGCAGGATGCGGCGGCTGTTTACCTTGA

GGCAATACTTCGGCATTTTGCACCGATTGCTGAAAAACCGTTAA (SEQ ID NO: 4)

MQPLVSVLICAYNVEKYFAQSLAAVVNQTWCNLDILIVDDGSTDGTLAIAKDFQKRDSR

IKILAQAQNSGLIPSLNIGLDELAKSGGGEYIARTDADDIAAPDWIEKIVGEMEKDRSIIAMGA

WLEVLSEEKDGNRLARHHRHGKIWKKPTRHEDIADFFPFGNPIHNNTMIMRRSVIDGGLRYNTE

RDWAEDYQFWYDVSKLGRLAYYPEALVKYRLHANQVSSKYSIRQHEIAQGIQKTARNDFLQSMG

FKTRFDSLEYRQIKAVAYELLEKHLPEEDFERARRFLYQCFKRTDTPPAGAWLDFAADGRMRRL

FTLRQYFGILHRLLKNR

Cv?3GalT WP_048405302.1

(SEQ ID NO: 5)

ATGGACACCATCATGATTAAACGTCCGCTGGTTAGCGTTATTCTGCCGGTGAATAAAAA

CAATCCGCATCTGGAAGAAGCAATCCAGAGCATTAAAAACCAGACCTATAAAGAGCTGGAACTG

ATCATTATTGCCAACAACTGCGAGGATAACTTTTATAGCCTGCTGCTGAAATATCAGGACCAGA

AAACCAAAATTATCCGCACCAGCATCAAATATCTGCCGTTTAGCCTGAATCTGGGTGTTCATCT

GAGCCAGGGTGAATATATTGCACGTATGGATTCAGATGATATCAGCGTTCTGGATCGCATTGAA

AAACAGGTTAAACGCTTTCTGAATACACCGGAACTGAGCATTCTGGGTAGCAATGTTGAATATA

TCAATGAAGCCAGCGAAAGCATTGGCTATAGCAACTATCCGCTGGATCATAGCAGCATTGTTAA

TAGCTTTCCGTTTCGTTGTAATCTGGCACATCCGACCATTATGGTTAAAAAAGAAGTGATTACC

ACGCTTGGTGGCTATATGTATGGTAGCCTGAGCGAAGATTATGATCTGTGGATTCGTGCAAGCC

GTCATGGCAATTTCAAATTTAGCAATATTGATGAACCGCTGCTGAAGTACCGTATTCATAAAGG

TCAGGCAACCAATAAAAGCAACGCCTATAACATCTTTGCCTTTGATAGCAGCCTGAAAATCCGT

GAATTTCTGCTGAATGGTAATGTGCAGTATCTGCTGGGTGCAGCACGTGGTTTTTTTGCATTTC

TGTATGTGCGTTTCATCAAAAAATAA (SEQ ID NO: 6)

MDTIMIKRPLVSVILPVNKNNPHLEEAIQSIKNQTYKELELIIIANNCEDNFYSLLLKY

QDQKTKIIRTSIKYLPFSLNLGVHLSQGEYIARMDSDDISVLDRIEKQVKRFLNTPELSILGSN

VEYINEASESIGYSNYPLDHSSIVNSFPFRCNLAHPTIMVKKEVITTLGGYMYGSLSEDYDLWI

RASRHGNFKFSNIDEPLLKYRIHKGQATNKSNAYNIFAFDSSLKIREFLLNGNVQYLLGAARGF

FAFLYVRFIKK*

Te2FT BAC08546.1

(SEQ ID NO: 7)

ATGATTATCGTTCACCTGTGCGGTGGCCTGGGCAACCAGATGTTCCAGTACGCAGCGGG

TCTGGCAGCAGCGCACCGTATCGGTTCTGAAGTGAAATTCGACACCCATTGGTTCGACGCGACT

TGTCTGCATCAGGGCCTGGAGCTGCGCCGTGTTTTTGGTCTGGAACTGCCGGAGCCGTCCTCTA

AAGACCTGCGTAAAGTTCTGGGCGCGTGTGTTCATCCGGCTGTTCGTCGTCTGCTGGCTGGCCA

CTTCCTGCATGGTCTGCGCCCGAAATCCCTGGTTATCCAGCCGCATTTCCACTACTGGACCGGT

TTTGAGCACCTGCCGGACAACGTTTACCTGGAGGGTTACTGGCAGTCCGAACGTTACTTCTCTA

ACATCGCGGATATCATCCGTCAGCAGTTTCGCTTCGTGGAACCGCTGGACCCGCACAACGCGGC

TCTGATGGATGAAATGCAGTCTGGTGTGTCTGTTTCTCTGCACATTCGTCGCGGCGATTACTTT

AACAACCCGCAGATGCGTCGCGTGCATGGCGTGGATCTGAGCGAATACTACCCGGCTGCTGTTG

CGACCATGATCGAGAAGACTAACGCAGAACGTTTCTACGTTTTCTCCGACGATCCGCAGTGGGT

-continued

TCTGGAGCATCTGAAGCTGCCGGTTAGCTATACCGTTGTGGATCACAACCGTGGTGCTGCGAGC

TACCGTGATATGCAGCTGATGTCCGCGTGCCGTCACCACATCATCGCGAACTCTACCTTCTCTT

GGTGGGGTGCGTGGCTGAACCCGCGTCCGGATAAAGTTGTTATCGCACCGCGCCACTGGTTTAA

CGTTGACGTTTTTGACACCCGCGATCTGTACTGCCCGGGTTGGATTGTTCTGTAA (SEQ ID NO: 8)

MIIVHLCGGLGNQMFQYAAGLAAAHRIGSEVKFDTHWFDATCLHQGLELRRVFGLELPE

PSSKDLRKVLGACVHPAVRRLLAGHFLHGLRPKSLVIQPHFHYWTGFEHLPDNVYLEGYWQSER

YFSNIADIIRQQFRFVEPLDPHNAALMDEMQSGVSVSLHIRRGDYFNNPQMRRVHGVDLSEYYP

AAVATMIEKTNAERFYVESDDPQWVLEHLKLPVSYTVVDHNRGAASYRDMQLMSACRHHIIANS

TFSWWGAWLNPRPDKVVIAPRHWENVDVFDTRDLYCPGWIVL*

NmLgtB Q8KR92

(SEQ ID NO: 9)

ATGCAAAACCACGTTATCAGCTTAGCTTCCGCCGCAGAACGCAGGGCGCACATTGCCGA

TACCTTCGGCAGGCACGGCATCCCGTTTCAGTTTTTCGACGCACTGATGCCGTCTGAAAGGCTG

GAACAGGCAATGGCGGAACTCGTCCCCGGCTTGTCGGCGCACCCCTATTTGAGCGGAGTGGAAA

AAGCCTGCTTTATGAGCCACGCCGTATTGTGGAAGCAGGCATTGGACGAAGGTCTGCCGTATAT

CACCGTATTTGAGGACGACGTTTTACTCGGCGAAGGTGCGGAAAAATTCCTTGCCGAAGACGCT

TGGCTGCAAGAACGCTTTGACCCGGATACCGCCTTTATCGTCCGCTTGGAAACGATGTTTATGC

ACGTCCTGACCTCGCCCTCCGGCGTGGCGGATTACTGCGGGCGCGCCTTTCCGCTGTTGGAAAG

CGAACACTGGGGGACGGCGGGCTATATCATTTCCCGAAAAGCGATGCGGTTTTTCCTGGACAGG

TTTGCCGCCCTGCCGCCCGAAGGGCTGCACCCCGTCGATCTGATGATGTTCAGCGATTTTTTCG

ACAGGGAAGGAATGCCGGTTTGCCAGCTCAATCCCGCCTTGTGCGCCCAAGAGCTGCATTATGC

CAAGTTTCACGACCAAAACAGCGCATTGGGCAGCCTGATCGAACACGACCGCCTCCTGAACCGC

AAACAGCAAAGGCGCGATTCCCCCGCCAACACATTCAAACACCGCCTGATCCGCGCCTTGACCA

AAATCAGCAGGGAAAGGGAAAAACGCCGGCAAAGGCGCGAACAGTTCATTGTGCCTTTCCAATA

A (SEQ ID NO: 10)

MQNHVISLASAAERRAHIADTFGRHGIPFQFFDALMPSERLEQAMAELVPGLSAHPYLS

GVEKACFMSHAVLWKQALDEGLPYITVFEDDVLLGEGAEKFLAEDAWLQERFDPDTAFIVRLET

MFMHVLTSPSGVADYCGRAFPLLESEHWGTAGYIISRKAMRFFLDRFAALPPEGLHPVDLMMFS

DFFDREGMPVCQLNPALCAQELHYAKFHDQNSALGSLIEHDRLLNRKQQRRDSPANTFKHRLIR

ALTKISREREKRRQRREQFIVPFQ*

HP0826 O25500

(SEQ ID NO: 11)

ATGCGTGTTTTTGCCATTTCTTTAAATCAAAAAGTGTGCGATACATTTGGTTTAGTTTT

TAGAGACACCACAACTTTACTCAATAGCATCAATGCCACCCACCACCAAGCGCAAATTTTTGAT

GCGATTTATTCTAAAACTTTTGAAGGCGGGTTGCACCCCTTAGTGAAAAAGCATTTACACCCTT

ATTTCATCACGCAAAACATCAAAGACATGGGGATTACAACCAATCTCATCAGTGAGGTTTCTAA

GTTTTATTACGCTTTAAAATACCATGCGAAGTTTATGAGCTTGGGGGAGCTTGGGTGCTATGCG

AGTCATTATTCCTTGTGGGAAAAAATGCATAGAACTCAATGAAGCGATCTGTATTTTAGAAGACG

ATATAACCTTGAAAGAGGATTTTAAAGAGGGCTTGGATTTTTTAGAAAAACACATCCAAGAGTT

AGGCTATATCCGCTTGATGCATTTATTGTATGATGCCAGTGTAAAAAGTGAGCCATTGAGCCAT

AAAAACCACGAGATACAAGAGCGTGTGGGGATCATTAAAGCTTATAGCGAAGGGGTGGGGACTC

AAGGCTATGTGATCACGCCTAAGATTGCCAAAGTTTTTTTGAAATGCAGCCGAAAATGGGTTGT

-continued

TCCTGTGGATACGATAATGGACGCTACTTTTATCCATGGCGTGAAAAATCTGGTGTTACAACCT

TTTGTGATCGCTGATGATGAGCAAATCTCTACGATAGCACGAAAAGAAGAACCTTATAGCCCTA

AAATCGCCTTAATGAGAGAACTCCATTTTAAATATTTGAAATATTGGCAGTTTGTATAA (SEQ ID NO: 12)

MRVFAISLNQKVCDTFGLVERDTTTLLNSINATHHQAQIFDAIYSKTFEGGLHPLVKKH

LHPYFITQNIKDMGITTNLISEVSKFYYALKYHAKFMSLGELGCYASHYSLWEKCIELNEAICI

LEDDITLKEDFKEGLDFLEKHIQELGYIRLMHLLYDASVKSEPLSHKNHEIQERVGIIKAYSEG

VGTQGYVITPKIAKVFLKCSRKWVVPVDTIMDATFIHGVKNLVLQPFVIADDEQISTIARKEEP

YSPKIALMRELHFKYLKYWQFV*

PMST3 AE004439

(SEQ ID NO: 13)

ATGGATAAATTTGCCGAACATGAAATTCCGAAAGCCGTTATTGTTGCAGGTAATGGTGA

AAGCCTGAGCCAGATTGATTATCGTCTGCTGCCGAAAAATTATGATGTGTTTCGCTGCAATCAG

TTTTATTTTGAAGAACGCTATTTTCTGGGCAATAAAATTAAAGCCGTGTTTTTTACACCGGGTG

TTTTTCTGGAACAGTATTATACCCTGTATCATCTGAAACGCAATAATGAATATTTTGTGGATAA

TGTGATTCTGAGCAGCTTTAATCATCCGACCGTTGATCTGGAAAAAAGCCAGAAAATTCAGGCC

CTGTTTATTGATGTGATTAATGGCTATGAAAAATATCTGAGCAAACTGACCGCCTTTGATGTTT

ATCTGCGCTATAAAGAACTGTATGAAAATCAGCGTATTACCAGCGGTGTTTATATGTGTGCAGT

TGCAATTGCAATGGGCTATACCGATATTTATCTGACCGGCATTGATTTTTATCAGGCCAGCGAA

GAAAATTATGCCTTTGATAATAAAAAACCGAATATTATTCGCCTGCTGCCGGATTTTCGCAAAG

AAAAAACCCTGTTTAGCTATCATAGCAAAGATATTGATCTGGAAGCCCTGAGCTTTCTGCAGCA

GCATTATCATGTGAATTTTTATAGCATTAGCCCGATGAGTCCGCTGAGCAAACATTTTCCGATT

CCGACCGTGGAAGATGATTGTGAAACCACCTTTGTTGCACCGCTGAAAGAAAATTATATTAATG

ATATTCTGCTGCCTCCGCATTTTGTGTATGAAAAACTGGGCGTCGACAAGCTTGCGGCCGCACT

CGAGTGA (SEQ ID NO: 14)

MDKFAEHEIPKAVIVAGNGESLSQIDYRLLPKNYDVFRCNQFYFEERYFLGNKIKAVFF

TPGVFLEQYYTLYHLKRNNEYFVDNVILSSFNHPTVDLEKSQKIQALFIDVINGYEKYLSKLTA

FDVYLRYKELYENQRITSGVYMCAVAIAMGYTDIYLTGIDFYQASEENYAFDNKKPNIIRLLPD

FRKEKTLFSYHSKDIDLEALSFLQQHYHVNFYSISPMSPLSKHFPIPTVEDDCETTEVAPLKEN

YINDILLPPHFVYEKLGVDKLAAALE* nst U60662.2

(SEQ ID NO: 15)

ATGGGCTTGAAAAAGGCTTGTTTGACCGTGTTGTGTTTGATTGTTTTTTGTTTCGGGAT

ATTTTATACATTTGACCGGGTAAATCAGGGGGAAAGGAATGCGGTTTCCCTGCTGAAGGAGAAA

CTTTTCAATGAAGAGGGGGAACCGGTCAATCTGATTTTCTGTTATACCATATTGCAGATGAAGG

TGGCGGAAAGGATTATGGCGCAGCATCCGGGCGAGCGGTTTTATGTGGTGCTGATGTCTGAAAA

CAGGAATGAAAAATACGATTATTATTTCAATCAGATAAAGGATAAGGCGGAGCGGGCGTACTTT

TTCCACCTGCCCTACGGTTTGAACAAATCGTTTAATTTCATTCCGACGATGGCGGAGCTGAAGG

TAAAGTCGATGCTGCTGCCGAAAGTCAAGCGGATTTATTTGGCAAGTTTGGAAAAAGTCAGCAT

TGCCGCCTTTTTGAGCACTTACCCGGATGCGGAAATCAAAACCTTTGACGACGGGACAGGCAAT

TTAATTCAAAGCAGCAGCTATTTGGGCGATGAGTTTTCTGTAAACGGGACGATCAAGCGGAATT

TTGCCCGGATGATGATCGGAGATTGGAGCATCGCCAAAACCCGCAATGCTTCCGACGAGCATTA

-continued

CACGATATTCAAGGGTTTGAAAAACATTATGGACGACGGCCGCCGCAAGATGACTTACCTGCCG

CTGTTCGATGCGTCCGAACTGAAGACGGGGGACGAAACGGGCGGCACGGTGCGGATACTTTTGG

GTTCGCCCGACAAAGAGATGAAGGAAATTTCGGAAAAGGCGGCAAAAAACTTCAAAATACAATA

TGTCGCGCCGCATCCCCGCCAAACCTACGGGCTTTCCGGCGTAACCACATTAAATTCGCCCTAT

GTCATCGAAGACTATATTTTGCGCGAGATTAAGAAAAACCCGCATACGAGGTATGAAATTTATA

CCTTTTTCAGCGGCGCGGCGTTGACGATGAAGGATTTTCCCAATGTGCACGTTTACGCATTGAA

ACCGGCTTCCCTTCCGGAAGATTATTGGCTCAAGCCGGTGTATGCCCTGTTTACCCAATCCGGC

ATCCCGATTTTGACATTTGACGATAAAAATTAA (SEQ ID NO: 16)

MGLKKACLTVLCLIVFCFGIFYTFDRVNQGERNAVSLLKEKLFNEEGEPVNLIFCYTIL

QMKVAERIMAQHPGERFYVVLMSENRNEKYDYYFNQIKDKAERAYFFHLPYGLNKSFNFIPTMA

ELKVKSMLLPKVKRIYLASLEKVSIAAFLSTYPDAEIKTFDDGTGNLIQSSSYLGDEFSVNGTI

KRNFARMMIGDWSIAKTRNASDEHYTIFKGLKNIMDDGRRKMTYLPLFDASELKTGDETGGTVR

ILLGSPDKEMKEISEKAAKNFKIQYVAPHPRQTYGLSGVTTLNSPYVIEDYILREIKKNPHTRY

EIYTFFSGAALTMKDFPNVHVYALKPASLPEDYWLKPVYALFTQSGIPILTFDDKN* st6 AB293985.1

(SEQ ID NO: 17)

ATGAAAAACTTTTTATTATTAACTTTAATATTACTTACTGCTTGTAATAATTCAGAAGA

AAATACACAATCTATTATTAAAAATGATATTAATAAAACTATTATTGATGAGGAGTATGTTAAT

TTAGAGCCAATTAATCAATCAAACATCTCTTTTACAAAACACTCTTGGGTACAAACTTGTGGTA

CGCAACAACTATTAACAGAACAAAATAAAGAGTCAATATCATTATCTGTAGTGGCGCCACGATT

AGATGACGATGAAAAGTACTGCTTTGATTTTAATGGTGTTAGTAATAAAGGTGAAAAATATATA

ACAAAAGTAACATTAAACGTAGTGGCTCCATCTTTAGAGGTTTATGTTGATCATGCATCTCTTC

CAACTCTTCAGCAGCTAATGGATATTATTAAATCGGAAGAAGAAAATCCTACAGCACAAAGATA

TATAGCTTGGGGGAGAATAGTTCCGACTGATGAGCAAATGAAAGAGTTAAATATTACATCGTTT

GCATTGATAAATAACCATACACCAGCTGACTTAGTACAAGAAATTGTTAAGCAAGCACAAACAA

AGCATAGATTGAATGTTAAACTTAGCTCTAACACTGCTCATTCATTTGATAATTTAGTGCCAAT

ACTAAAAGAATTAAATTCGTTTAATAACGTTACGGTAACAAATATAGATTTATATGATGATGGT

TCAGCAGAATATGTAAATTTATATAACTGGAGAGATACATTAAATAAAACAGATAATTTAAAAA

TTGGTAAAGATTATCTTGAGGATGTCATTAATGGTATCAATGAAGACACTTCAAATACAGGAAC

ATCATCTGTTTATAACTGGCAAAAACTATATCCAGCTAACTACCATTTTTTAAGAAAAGATTAT

TTAACTTTAGAACCATCATTACATGAGTTACGAGACTATATTGGTGATAGTTTAAAGCAAATGC

AATGGGATGGTTTCAAAAAATTCAATAGCAAACAACAAGAATTATTCTTATCGATTGTTAATTT

TGACAAACAAAAATTACAAAATGAATATAATTCATCTAATTTACCAAACTTTGTGTTTACAGGT

ACGACTGTATGGGCTGGTAACCATGAAAGAGAGTATTATGCGAAACAACAAATTAATGTCATTA

ATAATGCAATTAATGAATCGAGCCCACATTATTTAGGCAATAGTTATGATTTGTTCTTCAAAGG

TCACCCTGGTGGCGGTATCATTAATACATTAATAATGCAAAACTATCCTTCAATGGTTGATATT

CCATCAAAAATATCATTTGAAGTTTTGATGATGACAGATATGCTTCCTGATGCAGTTGCTGGTA

TAGCGAGCTCTTTATATTTCACGATACCAGCTGAAAAAATTAAATTTATAGTTTTTACATCGAC

AGAAACTATAACTGATCGTGAAACTGCTTTGAGAAGTCCTTTAGTTCAAGTAATGATAAAACTA

GGTATTGTAAAAGAAGAGAATGTACTTTTTTGGGCTGATCTGCCAAATTGTGAAACAGGTGTTT

GTATTGCAGTCTAG

-continued (SEQ ID NO: 18)
MKNFLLLTLILLTACNNSEENTQSIIKNDINKTIIDEEYVNLEPINQSNISFTKHSWVQ

TCGTQQLLTEQNKESISLSVVAPRLDDDEKYCFDFNGVSNKGEKYITKVTLNVVAPSLEVYVDH

ASLPTLQQLMDIIKSEEENPTAQRYIAWGRIVPTDEQMKELNITSFALINNHTPADLVQEIVKQ

AQTKHRLNVKLSSNTAHSFDNLVPILKELNSFNNVTVTNIDLYDDGSAEYVNLYNWRDTLNKTD

NLKIGKDYLEDVINGINEDTSNTGTSSVYNWQKLYPANYHFLRKDYLTLEPSLHELRDYIGDSL

KQMQWDGFKKFNSKQQELFLSIVNFDKQKLQNEYNSSNLPNFVFTGTTVWAGNHEREYYAKQQI

NVINNAINESSPHYLGNSYDLFFKGHPGGGIINTLIMQNYPSMVDIPSKISFEVLMMTDMLPDA

VAGIASSLYFTIPAEKIKFIVFTSTETITDRETALRSPLVQVMIKLGIVKEENVLFWADLPNCE

TGVCIAV* pgi P0A6T1

(SEQ ID NO: 19)
ATGAAAAACATCAATCCAACGCAGACCGCTGCCTGGCAGGCACTACAGAAACACTTCGA

TGAAATGAAAGACGTTACGATCGCCGATCTTTTTGCTAAAGACGGCGATCGTTTTTCTAAGTTC

TCCGCAACCTTCGACGATCAGATGCTGGTGGATTACTCCAAAAACCGCATCACTGAAGAGACGC

TGGCGAAATTACAGGATCTGGCGAAAGAGTGCGATCTGGCGGGCGCGATTAAGTCGATGTTCTC

TGGCGAGAAGATCAACCGCACTGAAAACCGCGCCGTGCTGCACGTAGCGCTGCGTAACCGTAGC

AATACCCCGATTTTGGTTGATGGCAAAGACGTAATGCCGGAAGTCAACGCGGTGCTGGAGAAGA

TGAAAACCTTCTCAGAAGCGATTATTTCCGGTGAGTGGAAAGGTTATACCGGCAAAGCAATCAC

TGACGTAGTGAACATCGGGATCGGCGGTTCTGACCTCGGCCCATACATGGTGACCGAAGCTCTG

CGTCCGTACAAAAACCACCTGAACATGCACTTTGTTTCTAACGTCGATGGGACTCACATCGCGG

AAGTGCTGAAAAAAGTAAACCCGGAAACCACGCTGTTCTTGGTAGCATCTAAAACCTTCACCAC

TCAGGAAACTATGACCAACGCCCATAGCGCGCGTGACTGGTTCCTGAAAGCGGCAGGTGATGAA

AAACACGTTGCAAAACACTTTGCGGCGCTTTCCACCAATGCCAAAGCCGTTGGCGAGTTTGGTA

TTGATACTGCCAACATGTTCGAGTTCTGGGACTGGGTTGGCGGCCGTTACTCTTTGTGGTCAGC

GATTGGCCTGTCGATTGTTCTCTCCATCGGCTTTGATAACTTCGTTGAACTGCTTTCCGGCGCA

CACGCGATGGACAAGCATTTCTCCACCACGCCTGCCGAGAAAAACCTGCCTGTACTGCTGGCGC

TGATTGGCATCTGGTACAACAATTTCTTTGGTGCGGAAACTGAAGCGATTCTGCCGTATGACCA

GTATATGCACCGTTTCGCGGCGTACTTCCAGCAGGGCAATATGGAGTCCAACGGTAAGTATGTT

GACCGTAACGGTAACGTTGTGGATTACCAGACTGGCCCGATTATCTGGGGTGAACCAGGCACTA

ACGGTCAGCACGCGTTCTACCAGCTGATCCACCAGGGAACCAAAATGGTACCGTGCGATTTCAT

CGCTCCGGCTATCACCCATAACCCGCTCTCTGATCATCACCAGAAACTGCTGTCTAACTTCTTC

GCCCAGACCGAAGCGCTGGCGTTTGGTAAATCCCGCGAAGTGGTTGAGCAGGAATATCGTGATC

AGGGTAAAGATCCGGCAACGCTTGACTACGTGGTGCCGTTCAAAGTATTCGAAGGTAACCGCCC

GACCAACTCCATCCTGCTGCGTGAAATCACTCCGTTCAGCCTGGGTGCGTTGATTGCGCTGTAT

GAGCACAAAATCTTTACTCAGGGCGTGATCCTGAACATCTTCACCTTCGACCAGTGGGGCGTGG

AACTGGGTAAACAGCTGGCGAACCGTATTCTGCCAGAGCTGAAAGATGATAAAGAAATCAGCAG

CCACGATAGCTCGACCAATGGTCTGATTAACCGCTATAAAGCGTGGCGCGGTTAA (SEQ ID NO: 20)
MKNINPTQTAAWQALQKHFDEMKDVTIADLFAKDGDRFSKFSATFDDQMLVDYSKNRIT

EETLAKLQDLAKECDLAGAIKSMFSGEKINRTENRAVLHVALRNRSNTPILVDGKDVMPEVNAV

LEKMKTFSEAIISGEWKGYTGKAITDVVNIGIGGSDLGPYMVTEALRPYKNHLNMHFVSNVDGT

HIAEVLKKVNPETTLFLVASKIFTTQETMINAHSARDWFLKAAGDEKHVAKHFAALSTNAKAVG

-continued

EFGIDTANMFEFWDWVGGRYSLWSAIGLSIVLSIGFDNFVELLSGAHAMDKHFSTTPAEKNLPV

LLALIGIWYNNFFGAETEAILPYDQYMHRFAAYFQQGNMESNGKYVDRNGNVVDYQTGPIIWGE

PGTNGQHAFYQLIHQGTKMVPCDFIAPAITHNPLSDHHQKLLSNFFAQTEALAFGKSREVVEQE

YRDQGKDPATLDYVVPFKVFEGNRPTNSILLREITPFSLGALIALYEHKIFTQGVILNIFTFDQ

WGVELGKQLANRILPELKDDKEISSHDSSTNGLINRYKAWRG* pgm P36938

(SEQ ID NO: 21)

ATGGCAATCCACAATCGTGCAGGCCAACCTGCACAACAGAGTGATTTGATTAACGTCGC

CCAACTGACGGCGCAATATTATGTACTGAAACCAGAAGCAGGGAATGCGGAGCACGCGGTGAAA

TTCGGTACTTCCGGTCACCGTGGCAGTGCAGCGCGCCACAGCTTTAACGAGCCGCACATTCTGG

CGATCGCTCAGGCAATTGCTGAAGAACGTGCGAAAAACGGCATCACTGGCCCTTGCTATGTGGG

TAAAGATACTCACGCCCTGTCCGAACCTGCATTCATTTCCGTTCTGGAAGTGCTGGCAGCGAAC

GGCGTTGATGTCATTGTGCAGGAAAACAATGGCTTCACCCCGACGCCTGCCGTTTCCAATGCCA

TCCTGGTTCACAATAAAAAAGGTGGCCCGCTGGCAGACGGTATCGTGATTACACCGTCCCATAA

CCCGCCGGAAGATGGTGGAATCAAATACAATCCGCCAAATGGTGGCCCGGCTGATACCAACGTC

ACTAAAGTGGTGGAAGACAGGGCCAACGCACTGCTGGCCGATGGCCTGAAAGGCGTGAAGCGTA

TCTCCCTCGACGAAGCGATGGCATCCGGTCATGTGAAAGAGCAGGATCTGGTGCAGCCGTTCGT

GGAAGGTCTGGCCGATATCGTTGATATGGCCGCGATTCAGAAAGCGGGCCTGACGCTGGGCGTT

GATCCGCTGGGCGGTTCCGGTATCGAATACTGGAAGCGTATTGGCGAGTATTACAACCTCAACC

TGACTATCGTTAACGATCAGGTCGATCAAACCTTCCGCTTTATGCACCTTGATAAAGACGGCGC

GATCCGTATGGACTGCTCCTCCGAGTGTGCGATGGCGGGCCTGCTGGCACTGCGTGATAAGTTC

GATCTGGCGTTTGCTAACGACCCGGATTATGACCGTCACGGTATCGTCACTCCGGCAGGTTTGA

TGAATCCGAACCACTACCTGGCGGTGGCAATCAATTACCTGTTCCAGCATCGTCCGCAGTGGGG

CAAAGATGTTGCCGTCGGTAAAACGCTGGTTTCATCTGCGATGATCGACCGTGTGGTCAACGAC

TTGGGCCGTAAACTGGTAGAAGTCCCGGTAGGTTTCAAATGGTTTGTCGATGGTCTGTTCGACG

GCAGCTTCGGCTTTGGCGGCGAAGAGAGTGCAGGGGCTTCCTTCCTGCGTTTCGACGGCACGCC

GTGGTCCACCGACAAAGACGGCATCATCATGTGTCTGCTGGCGGCGGAAATCACCGCTGTCACC

GGTAAGAACCCGCAGGAACACTACAACGAACTGGCAAAACGCTTTGGTGCGCCGAGCTACAACC

GTTTGCAGGCAGCTGCGACTTCCGCACAAAAAGCGGCGCTGTCTAAGCTGTCTCCGGAAATGGT

GAGCGCCAGCACCCTGGCAGGTGACCCGATCACCGCGCGCCTGACTGCTGCTCCGGGCAACGGT

GCTTCTATTGGCGGTCTGAAAGTGATGACTGACAACGGCTGGTTCGCCGCGCGTCCGTCAGGCA

CGGAAGACGCATATAAGATCTACTGCGAAAGCTTCCTCGGTGAAGAACATCGCAAGCAGATTGA

GAAAGAAGCGGTTGAGATTGTTAGCGAAGTTCTGAAAAACGCGTAA (SEQ ID NO: 22)

MAIHNRAGQPAQQSDLINVAQLTAQYYVLKPEAGNAEHAVKFGTSGHRGSAARHSFNEP

HILAIAQAIAEERAKNGITGPCYVGKDTHALSEPAFISVLEVLAANGVDVIVQENNGFTPTPAV

SNAILVHNKKGGPLADGIVITPSHNPPEDGGIKYNPPNGGPADTNVTKVVEDRANALLADGLKG

VKRISLDEAMASGHVKEQDLVQPFVEGLADIVDMAAIQKAGLILGVDPLGGSGIEYWKRIGEYY

NLNLTIVNDQVDQTFRFMHLDKDGAIRMDCSSECAMAGLLALRDKFDLAFANDPDYDRHGIVTP

AGLMNPNHYLAVAINYLFQHRPQWGKDVAVGKTLVSSAMIDRVVNDLGRKLVEVPVGFKWFVDG

-continued

LFDGSFGFGGEESAGASFLRFDGTPWSTDKDGIIMCLLAAEITAVTGKNPQEHYNELAKRFGAP

SYNRLQAAATSAQKAALSKLSPEMVSASTLAGDPITARLTAAPGNGASIGGLKVMTDNGWFAAR

PSGTEDAYKIYCESFLGEEHRKQIEKEAVEIVSEVLKNA* galU P0AEP3

(SEQ ID NO: 23)

ATGGCTGCCATTAATACGAAAGTCAAAAAAGCCGTTATCCCCGTTGCGGGATTAGGAAC

CAGGATGTTGCCGGCGACGAAAGCCATCCCGAAAGAGATGCTGCCACTTGTCGATAAGCCATTA

ATTCAATACGTCGTGAATGAATGTATTGCGGCTGGCATTACTGAAATTGTGCTGGTTACACACT

CATCTAAAAACTCTATTGAAAACCACTTTGATACCAGTTTTGAACTGGAAGCAATGCTGGAAAA

ACGTGTAAAACGTCAACTGCTTGATGAAGTGCAGTCTATTTGTCCACCGCACGTGACTATTATG

CAAGTTCGTCAGGGTCTGGCGAAAGGCCTGGGACACGCGGTATTGTGTGCTCACCCGGTAGTGG

GTGATGAACCGGTAGCTGTTATTTTGCCTGATGTTATTCTGGATGAATATGAATCCGATTTGTC

ACAGGATAACCTGGCAGAGATGATCCGCCGCTTTGATGAAACGGGTCATAGCCAGATCATGGTT

GAACCGGTTGCTGATGTGACCGCATATGGCGTTGTGGATTGCAAAGGCGTTGAATTAGCGCCGG

GTGAAAGCGTACCGATGGTTGGTGTGGTAGAAAAACCGAAAGCGGATGTTGCGCCGTCTAATCT

CGCTATTGTGGGTCGTTACGTACTTAGCGCGGATATTTGGCCGTTGCTGGCAAAAACCCCTCCG

GGAGCTGGTGATGAAATTCAGCTCACCGACGCAATTGATATGCTGATCGAAAAAGAAACGGTGG

AAGCCTATCATATGAAAGGGAAGAGCCATGACTGCGGTAATAAATTAGGTTACATGCAGGCCTT

CGTTGAATACGGTATTCGTCATAACACCCTTGGCACGGAATTTAAAGCCTGGCTTGAAGAAGAG

ATGGGCATTAAGAAGTAA (SEQ ID NO: 24)

MAAINTKVKKAVIPVAGLGTRMLPATKAIPKEMLPLVDKPLIQYVVNECIAAGITEIVL

VTHSSKNSIENHFDTSFELEAMLEKRVKRQLLDEVQSICPPHVTIMQVRQGLAKGLGHAVLCAH

PVVGDEPVAVILPDVILDEYESDLSQDNLAEMIRRFDETGHSQIMVEPVADVTAYGVVDCKGVE

LAPGESVPMVGVVEKPKADVAPSNLAIVGRYVLSADIWPLLAKTPPGAGDEIQLTDAIDMLIEK

ETVEAYHMKGKSHDCGNKLGYMQAFVEYGIRHNTLGTEFKAWLEEEMGIKK* galE P09147

(SEQ ID NO: 25)

ATGAGAGTTCTGGTTACCGGTGGTAGCGGTTACATTGGAAGTCATACCTGTGTGCAATT

ACTGCAAAACGGTCATGATGTCATCATTCTTGATAACCTCTGTAACAGTAAGCGCAGCGTACTG

CCTGTTATCGAGCGTTTAGGCGGCAAACATCCAACGTTTGTTGAAGGCGATATTCGTAACGAAG

CGTTGATGACCGAGATCCTGCACGATCACGCTATCGACACCGTGATCCACTTCGCCGGGCTGAA

AGCCGTGGGCGAATCGGTACAAAAACCGCTGGAATATTACGACAACAATGTCAACGGCACTCTG

CGCCTGATTAGCGCCATGCGCGCCGCTAACGTCAAAAACTTTATTTTTAGCTCCTCCGCCACCG

TTTATGGCGATCAGCCCAAAATTCCATACGTTGAAAGCTTCCCGACCGGCACACCGCAAAGCCC

TTACGGCAAAAGCAAGCTGATGGTGGAACAGATCCTCACCGATCTGCAAAAAGCCCAGCCGGAC

TGGAGCATTGCCCTGCTGCGCTACTTCAACCCGGTTGGCGCGCATCCGTCGGGCGATATGGGCG

AAGATCCGCAAGGCATTCCGAATAACCTGATGCCATACATCGCCCAGGTTGCTGTAGGCCGTCG

CGACTCGCTGGCGATTTTTGGTAACGATTATCCGACCGAAGATGGTACTGGCGTACGCGATTAC

ATCCACGTAATGGATCTGGCGGACGGTCACGTCGTGGCGATGGAAAAACTGGCGAACAAGCCAG

GCGTACACATCTACAACCTCGGCGCTGGCGTAGGCAACAGCGTGCTGGACGTGGTTAATGCCTT

-continued

CAGCAAAGCCTGCGGCAAACCGGTTAATTATCATTTTGCACCGCGTCGCGAGGGCGACCTTCCG

GCCTACTGGGCGGACGCCAGCAAAGCCGACCGTGAACTGAACTGGCGCGTAACGCGCACACTCG

ATGAAATGGCGCAGGACACCTGGCACTGGCAGTCACGCCATCCACAGGGATATCCCGATTAA (SEQ ID NO: 26)

MRVLVTGGSGYIGSHTCVQLLQNGHDVIILDNLCNSKRSVLPVIERLGGKHPTFVEGDI

RNEALMTEILHDHAIDTVIHFAGLKAVGESVQKPLEYYDNNVNGTLRLISAMRAANVKNFIFSS

SATVYGDQPKIPYVESFPTGTPQSPYGKSKLMVEQILTDLQKAQPDWSIALLRYENPVGAHPSG

DMGEDPQGIPNNLMPYIAQVAVGRRDSLAIFGNDYPTEDGTGVRDYIHVMDLADGHVVAMEKLA

NKPGVHIYNLGAGVGNSVLDVVNAFSKACGKPVNYHFAPRREGDLPAYWADASKADRELNWRVT

RTLDEMAQDTWHWQSRHPQGYPD*

ManA P00946

(SEQ ID NO: 27)

ATGCAAAAACTCATTAACTCAGTGCAAAACTATGCCTGGGGCAGCAAAACGGCGTTGAC

TGAACTTTATGGTATGGAAAATCCGTCCAGCCAGCCGATGGCCGAGCTGTGGATGGGCGCACAT

CCGAAAAGCAGTTCACGAGTGCAGAATGCCGCCGGAGATATCGTTTCACTGCGTGATGTGATTG

AGAGTGATAAATCGACTCTGCTCGGAGAGGCCGTTGCCAAACGCTTTGGCGAACTGCCTTTCCT

GTTCAAAGTATTATGCGCAGCACAGCCACTCTCCATTCAGGTTCATCCAAACAAACACAATTCT

GAAATCGGTTTTGCCAAAGAAAATGCCGCAGGTATCCCGATGGATGCCGCCGAGCGTAACTATA

AAGATCCTAACCACAAGCCGGAGCTGGTTTTTGCGCTGACGCCTTTCCTTGCGATGAACGCGTT

TCGTGAATTTTCCGAGATTGTCTCCCTACTCCAGCCGGTCGCAGGTGCACATCCGGCGATTGCT

CACTTTTTACAACAGCCTGATGCCGAACGTTTAAGCGAACTGTTCGCCAGCCTGTTGAATATGC

AGGGTGAAGAAAAATCCCGCGCGCTGGCGATTTTAAAATCGGCCCTCGATAGCCAGCAGGGTGA

ACCGTGGCAAACGATTCGTTTAATTTCTGAATTTTACCCGGAAGACAGCGGTCTGTTCTCCCCG

CTATTGCTGAATGTGGTGAAATTGAACCCTGGCGAAGCGATGTTCCTGTTCGCTGAAACACCGC

ACGCTTACCTGCAAGGCGTGGCGCTGGAAGTGATGGCAAACTCCGATAACGTGCTGCGTGCGGG

TCTGACGCCTAAATACATTGATATTCCGGAACTGGTTGCCAATGTGAAATTCGAAGCCAAACCG

GCTAACCAGTTGTTGACCCAGCCGGTGAAACAAGGTGCAGAACTGGACTTCCCGATTCCAGTGG

ATGATTTTGCCTTCTCGCTGCATGACCTTAGTGATAAAGAAACCACCATTAGCCAGCAGAGTGC

CGCCATTTTGTTCTGCGTCGAAGGCGATGCAACGTTGTGGAAAGGTTCTCAGCAGTTACAGCTT

AAACCGGGTGAATCAGCGTTTATTGCCGCCAACGAATCACCGGTGACTGTCAAAGGCCACGGCC

GTTTAGCGCGTGTTTACAACAAGCTGTAA (SEQ ID NO: 28)

MQKLINSVQNYAWGSKTALTELYGMENPSSQPMAELWMGAHPKSSSRVQNAAGDIVSLR

DVIESDKSTLLGEAVAKRFGELPFLFKVLCAAQPLSIQVHPNKHNSEIGFAKENAAGIPMDAAE

RNYKDPNHKPELVFALTPFLAMNAFREFSEIVSLLQPVAGAHPAIAHFLQQPDAERLSELFASL

LNMQGEEKSRALAILKSALDSQQGEPWQTIRLISEFYPEDSGLFSPLLLNVVKLNPGEAMFLFA

ETPHAYLQGVALEVMANSDNVLRAGLIPKYIDIPELVANVKFEAKPANQLLTQPVKQGAELDFP

IPVDDFAFSLHDLSDKETTISQQSAAILFCVEGDATLWKGSQQLQLKPGESAFIAANESPVTVK

GHGRLARVYNKL*

ManB P24175

(SEQ ID NO: 29)

ATGAAAAAATTAACCTGCTTTAAAGCCTATGATATTCGCGGGAAATTAGGCGAAGAACT

GAATGAAGATATCGCCTGGCGCATTGGTCGCGCCTATGGCGAATTTCTCAAACCGAAAACCATT

-continued

GTGTTAGGCGGTGATGTCCGCCTCACCAGCGAAACCTTAAAACTGGCGCTGGCGAAAGGTTTAC

AGGATGCGGGCGTTGACGTGCTGGATATTGGTATGTCCGGCACCGAAGAGATCTATTTCGCCAC

GTTCCATCTCGGCGTGGATGGCGGCATTGAAGTTACCGCCAGCCATAATCCGATGGATTATAAC

GGCATGAAGCTGGTTCGCGAGGGGGCTCGCCCGATCAGCGGAGATACCGGACTGCGCGACGTCC

AGCGTCTGGCTGAAGCCAACGACTTTCCTCCCGTCGATGAAACCAAACGCGGTCGCTATCAGCA

AATCAACCTGCGTGACGCTTACGTTGATCACCTGTTCGGTTATATCAATGTCAAAAACCTCACG

CCGCTCAAGCTGGTGATCAACTCCGGGAACGGCGCAGCGGGTCCGGTGGTGGACGCCATTGAAG

CCCGCTTTAAAGCCCTCGGCGCGCCCGTGGAATTAATCAAAGTGCACAACACGCCGGACGGCAA

TTTCCCCAACGGTATTCCTAACCCACTACTGCCGGAATGCCGCGACGACACCCGCAATGCGGTC

ATCAAACACGGCGCGGATATGGGCATTGCTTTTGATGGCGATTTTGACCGCTGTTTCCTGTTTG

ACGAAAAAGGGCAGTTTATTGAGGGCTACTACATTGTCGGCCTGTTGGCAGAAGCATTCCTCGA

AAAAAATCCCGGCGCGAAGATCATCCACGATCCACGTCTCTCCTGGAACACCGTTGATGTGGTG

ACTGCCGCAGGTGGCACGCCGGTAATGTCGAAAACCGGACACGCCTTTATTAAAGAACGTATGC

GCAAGGAAGACGCCATCTATGGTGGCGAAATGAGCGCCCACCATTACTTCCGTGATTTCGCTTA

CTGCGACAGCGGCATGATCCCGTGGCTGCTGGTCGCCGAACTGGTGTGCCTGAAAGATAAAACG

CTGGGCGAACTGGTACGCGACCGGATGGCGGCGTTTCCGGCAAGCGGTGAGATCAACAGCAAAC

TGGCGCAACCCGTTGAGGCGATTAACCGCGTGGAACAGCATTTTAGCCGTGAGGCGCTGGCGGT

GGATCGCACCGATGGCATCAGCATGACCTTTGCCGACTGGCGCTTTAACCTGCGCACCTCCAAT

ACCGAACCGGTGGTGCGCCTGAATGTGGAATCGCGCGGTGATGTGCCGCTGATGGAAGCGCGAA

CGCGAACTCTGCTGACGTTGCTGAACGAGTAA (SEQ ID NO: 30)

MKKLTCFKAYDIRGKLGEELNEDIAWRIGRAYGEFLKPKTIVLGGDVRLTSETLKLALA

KGLQDAGVDVLDIGMSGTEEIYFATFHLGVDGGIEVTASHNPMDYNGMKLVREGARPISGDTGL

RDVQRLAEANDFPPVDETKRGRYQQINLRDAYVDHLFGYINVKNLTPLKLVINSGNGAAGPVVD

AIEARFKALGAPVELIKVHNTPDGNFPNGIPNPLLPECRDDTRNAVIKHGADMGIAFDGDEDRC

FLFDEKGQFIEGYYIVGLLAEAFLEKNPGAKIIHDPRLSWNTVDVVTAAGGTPVMSKTGHAFIK

ERMRKEDAIYGGEMSAHHYFRDFAYCDSGMIPWLLVAELVCLKDKTLGELVRDRMAAFPASGEI

NSKLAQPVEAINRVEQHFSREALAVDRTDGISMTFADWRFNLRISNTEPVVRLNVESRGDVPLM

EARTRTLLTLLNE*

ManC P24174

(SEQ ID NO: 31)

ATGGCGCAGTCGAAACTCTATCCAGTTGTGATGGCAGGTGGCTCCGGTAGCCGCTTATG

GCCGCTTTCCCGCGTACTTTATCCCAAGCAGTTTTTATGCCTGAAAGGCGATCTCACCATGCTG

CAAACCACCATCTGCCGCCTGAACGGCGTGGAGTGCGAAAGCCCGGTGGTGATTTGCAATGAGC

AGCACCGCTTTATTGTCGCGGAACAGCTGCGTCAACTGAACAAACTTACCGAGAACATTATTCT

CGAACCGGCAGGGCGAAACACGGCACCTGCCATTGCGCTGGCGGCGCTGGCGGCAAAACGTCAT

AGCCCGGAGAGCGACCCGTTAATGCTGGTATTGGCGGCGGATCATGTGATTGCCGATGAAGACG

CGTTCCGTGCCGCCGTGCGTAATGCCATGCCATATGCCGAAGCGGGCAAGCTGGTGACCTTCGG

CATTGTGCCGGATCTACCAGAAACCGGTTATGGCTATATTCGTCGCGGTGAAGTGTCTGCGGGT

GAGCAGGATATGGTGGCCTTTGAAGTGGCGCAGTTTGTCGAAAAACCGAATCTGGAAACCGCTC

AGGCCTATGTGGCAAGCGGCGAATATTACTGGAACAGCGGTATGTTCCTGTTCCGCGCCGGACG

CTATCTCGAAGAACTGAAAAAATATCGCCCGGATATCCTCGATGCCTGTGAAAAAGCGATGAGC

-continued

GCCGTCGATCCGGATCTCAATTTTATTCGCGTGGATGAAGAAGCGTTTCTCGCCTGCCCGGAAG

AGTCGGTGGATTACGCGGTCATGGAACGTACGGCAGATGCTGTTGTGGTGCCGATGGATGCGGG

CTGGAGCGATGTTGGCTCCTGGTCTTCATTATGGGAGATCAGCGCCCACACCGCCGAGGGCAAC

GTTTGCCACGGCGATGTGATTAATCACAAAACTGAAAACAGCTATGTGTATGCTGAATCTGGCC

TGGTCACCACCGTCGGGGTGAAAGATCTGGTAGTGGTGCAGACCAAAGATGCGGTGCTGATTGC

CGACCGTAACGCGGTACAGGATGTGAAAAAAGTGGTCGAGCAGATCAAAGCCGATGGTCGCCAT

GAGCATCGGGTGCATCGCGAAGTGTATCGTCCGTGGGGCAAATATGACTCTATCGACGCGGGCG

ACCGCTACCAGGTGAAACGCATCACCGTGAAACCGGGCGAGGGCTTGTCGGTACAGATGCACCA

TCACCGCGCGGAACACTGGGTGGTTGTCGCGGGAACGGCAAAAGTCACCATTGATGGTGATATC

AAACTGCTTGGTGAAAACGAGTCCATTTATATTCCGCTGGGGGCGACGCATTGCCTGGAAAACC

CGGGGAAAATTCCGCTCGATTTAATTGAAGTGCGCTCCGGCTCTTATCTCGAAGAGGATGATGT

GGTGCGTTTCGCGGATCGCTACGGACGGGTGTAA (SEQ ID NO: 32)

MAQSKLYPVVMAGGSGSRLWPLSRVLYPKQFLCLKGDLIMLQTTICRLNGVECESPVVI

CNEQHRFIVAEQLRQLNKLTENIILEPAGRNTAPAIALAALAAKRHSPESDPLMLVLAADHVIA

DEDAFRAAVRNAMPYAEAGKLVTFGIVPDLPETGYGYIRRGEVSAGEQDMVAFEVAQFVEKPNL

ETAQAYVASGEYYWNSGMFLFRAGRYLEELKKYRPDILDACEKAMSAVDPDLNFIRVDEEAFLA

CPEESVDYAVMERTADAVVVPMDAGWSDVGSWSSLWEISAHTAEGNVCHGDVINHKTENSYVYA

ESGLVTTVGVKDLVVVQTKDAVLIADRNAVQDVKKVVEQIKADGRHEHRVHREVYRPWGKYDSI

DAGDRYQVKRITVKPGEGLSVQMHHHRAEHWVVVAGTAKVTIDGDIKLLGENESIYIPLGATHC

LENPGKIPLDLIEVRSGSYLEEDDVVRFADRYGRV*

Gmd P0AC88

(SEQ ID NO: 33)

ATGTCAAAAGTCGCTCTCATCACCGGTGTAACCGGACAAGACGGTTCTTACCTGGCAGA

GTTTCTGCTGGAAAAAGGTTACGAGGTGCATGGTATTAAGCGTCGCGCATCGTCATTCAACACC

GAGCGCGTGGATCACATTTATCAGGATCCGCACACCTGCAACCCGAAATTCCATCTGCATTATG

GCGACCTGAGTGATACCTCTAACCTGACGCGCATTTTGCGTGAAGTACAGCCGGATGAAGTGTA

CAACCTGGGCGCAATGAGCCACGTTGCGGTCTCTTTTGAGTCACCAGAATATACCGCTGACGTC

GACGCGATGGGTACGCTGCGCCTGCTGGAGGCGATCCGCTTCCTCGGTCTGGAAAAGAAAACTC

GTTTCTATCAGGCTTCCACCTCTGAACTGTATGGTCTGGTGCAGGAAATTCCGCAGAAAGAGAC

CACGCCGTTCTACCCGCGATCTCCGTATGCGGTCGCCAAACTGTACGCCTACTGGATCACCGTT

AACTACCGTGAATCCTACGGCATGTACGCCTGTAACGGAATTCTCTTCAACCATGAATCCCCGC

GCCGCGGCGAAACCTTCGTTACCCGCAAAATCACCCGCGCAATCGCCAACATCGCCCAGGGGCT

GGAGTCGTGCCTGTACCTCGGCAATATGGATTCCCTGCGTGACTGGGGCCACGCCAAAGACTAC

GTAAAAATGCAGTGGATGATGCTGCAGCAGGAACAGCCGGAAGATTTCGTTATCGCGACCGGCG

TTCAGTACTCCGTGCGTCAGTTCGTGGAAATGGCGGCAGCACAGCTGGGCATCAAACTGCGCTT

TGAAGGCACGGGCGTTGAAGAGAAGGGCATTGTGGTTTCCGTCACCGGGCATGACGCGCCGGGC

GTTAAACCGGGTGATGTGATTATCGCTGTTGACCCGCGTTACTTCCGTCCGGCTGAAGTTGAAA

CGCTGCTCGGCGACCCGACCAAAGCGCACGAAAAACTGGGCTGGAAACCGGAAATCACCCTCAG

AGAGATGGTGTCTGAAATGGTGGCTAATGACCTCGAAGCGGCGAAAAAACACTCTCTGCTGAAA

TCTCACGGCTACGACGTGGCGATCGCGCTGGAGTCATAA

-continued (SEQ ID NO: 34)
MSKVALITGVTGQDGSYLAEFLLEKGYEVHGIKRRASSENTERVDHIYQDPHTCNPKFH

LHYGDLSDTSNLTRILREVQPDEVYNLGAMSHVAVSFESPEYTADVDAMGTLRLLEAIRFLGLE

KKTRFYQASTSELYGLVQEIPQKETTPFYPRSPYAVAKLYAYWITVNYRESYGMYACNGILFNH

ESPRRGETFVTRKITRAIANIAQGLESCLYLGNMDSLRDWGHAKDYVKMQWMMLQQEQPEDFVI

ATGVQYSVRQFVEMAAAQLGIKLRFEGTGVEEKGIVVSVTGHDAPGVKPGDVIIAVDPRYFRPA

EVETLLGDPTKAHEKLGWKPEITLREMVSEMVANDLEAAKKHSLLKSHGYDVATALES*

WcaG P32055

(SEQ ID NO: 35)
ATGAGTAAACAACGAGTTTTTATTGCTGGTCATCGCGGGATGGTCGGTTCCGCCATCAA

GCGACAGCTCGAACAGCGCGGTGATGTGGAGCTGGTATTACGCACCCGCGATGAACTGAACCTG

CTGGACAGCCGCGCGGTGCATGATTTCTTTGCCAGCGAAAGCATTGACCAGGTCTATCTGGCGG

CGGCGAAAGTGGGCGGCATTGTTGCCAACAACACGTATCCGGCGGATTTCATCTACCAGAACAT

GATGATTGAGAGCAACATCATTCACGCCGCGCATCAGAACGACGTGAACAAACTGCTGTTTCTC

GGATCGTCCTGTATCTACCCGAAACTGGCAAAACAGCCGATGGCAGAAAGCGAGTTATTGCAGG

GCACGCTGGAGCCGACCAACGAGCCTTATGCCATTGCCAAAATTGCCGGGATCAAACTGTGCGA

ATCTTACAACCGCCAGTACGGACGCGATTACCGCTCAGTCATGCCGACCAACCTGTATGGCCCG

CATGACAACTTCCACCCGAGTAATTCGCATGTGATCCCAGCATTGTTGCGTCGCTTCCACGAGG

CGACGGCACAGAATGCGCCGGACGTTGTGGTATGGGGCAGCGGTACACCGATGCGTGAATTCCT

GCACGTCGATGATATGGCGGCGGCCAGCATTCACGTGATGGAGCTGGCGCACGAAGTCTGGCTG

GAGAACACCCAGCCGATGCTGTCGCACATTAACGTCGGTACCGGTGTTGACTGCACTATCCGCG

AGCTGGCGCAAACCATCGCCAAAGTGGTGGATTACAAAGGTCGGGTGGTTTTTGATGCCAGCAA

GCCGGATGGTACGCCGCGCAAACTGCTGGATGTGACGCGCCTGCATCAGCTTGGCTGGTATCAC

GAAATCTCACTGGAAGCGGGGCTTGCCAGCACTTACCAGTGGTTCCTTGAGAATCGAGACCGCT

TTCGGGGGTAA (SEQ ID NO: 36)
MSKQRVFIAGHRGMVGSAIKRQLEQRGDVELVLRTRDELNLLDSRAVHDFFASESIDQV

YLAAAKVGGIVANNTYPADFIYQNMMIESNIIHAAHQNDVNKLLFLGSSCIYPKLAKQPMAESE

LLQGTLEPTNEPYAIAKIAGIKLCESYNRQYGRDYRSVMPINLYGPHDNFHPSNSHVIPALLRR

FHEATAQNAPDVVVWGSGTPMREFLHVDDMAAASIHVMELAHEVWLENTQPMLSHINVGTGVDC

TIRELAQTIAKVVDYKGRVVFDASKPDGTPRKLLDVTRLHQLGWYHEISLEAGLASTYQWFLEN

RDRFRG* glmS AAC76752

(SEQ ID NO: 37)
ATGTGTGGAATTGTTGGCGCGATCGCGCAACGTGATGTAGCAGAAATCCTTCTTGAAGG

TTTACGTCGTCTGGAATACCGCGGATATGACTCTGCCGGTCTGGCCGTTGTTGATGCAGAAGGT

CATATGACCCGCCTGCGTCGCCTCGGTAAAGTCCAGATGCTGGCACAGGCAGCGGAAGAACATC

CTCTGCATGGCGGCACTGGTATTGCTCACACTCGCTGGGCGACCCACGGTGAACCTTCAGAAGT

GAATGCGCATCCGCATGTTTCTGAACACATTGTGGTGGTGCATAACGGCATCATCGAAAACCAT

GAACCGCTGCGTGAAGAGCTAAAAGCGCGTGGCTATACCTTCGTTTCTGAAACCGACACCGAAG

TGATTGCCCATCTGGTGAACTGGGAGCTGAAACAAGGCGGGACTCTGCGTGAGGCCGTTCTGCG

TGCTATCCCGCAGCTGCGTGGTGCGTACGGTACAGTGATCATGGACTCCCGTCACCCGGATACC

CTGCTGGCGGCACGTTCTGGTAGTCCGCTGGTGATTGGCCTGGGGATGGGCGAAAACTTTATCG

-continued

CTTCTGACCAGCTGGCGCTGTTGCCGGTGACCCGTCGCTTTATCTTCCTTGAAGAGGGCGATAT

TGCGGAAATCACTCGCCGTTCGGTAAACATCTTCGATAAAACTGGCGCGGAAGTAAAACGTCAG

GATATCGAATCCAATCTGCAATATGACGCGGGCGATAAAGGCATTTACCGTCACTACATGCAGA

AAGAGATCTACGAACAGCCGAACGCGATCAAAAACACCCTTACCGGACGCATCAGCCACGGTCA

GGTTGATTTAAGCGAGCTGGGACCGAACGCCGACGAACTGCTGTCGAAGGTTGAGCATATTCAG

ATCCTCGCCTGTGGTACTTCTTATAACTCCGGTATGGTTTCCCGCTACTGGTTTGAATCGCTAG

CAGGTATTCCGTGCGACGTCGAAATCGCCTCTGAATTCCGCTATCGCAAATCTGCCGTGCGTCG

TAACAGCCTGATGATCACCTTGTCACAGTCTGGCGAAACCGCGGATACCCTGGCTGGCCTGCGT

CTGTCGAAAGAGCTGGGTTACCTTGGTTCACTGGCAATCTGTAACGTTCCGGGTTCTTCTCTGG

TGCGCGAATCCGATCTGGCGCTAATGACCAACGCGGGTACAGAAATCGGCGTGGCATCCACTAA

AGCATTCACCACTCAGTTAACTGTGCTGTTGATGCTGGTGGCGAAGCTGTCTCGCCTGAAAGGT

CTGGATGCCTCCATTGAACATGACATCGTGCATGGTCTGCAGGCGCTGCCGAGCCGTATTGAGC

AGATGCTGTCTCAGGACAAACGCATTGAAGCGCTGGCAGAAGATTTCTCTGACAAACATCACGC

GCTGTTCCTGGGCCGTGGCGATCAGTACCCAATCGCGCTGGAAGGCGCATTGAAGTTGAAAGAG

ATCTCTTACATTCACGCTGAAGCCTACGCTGCTGGCGAACTGAAACACGGTCCGCTGGCGCTAA

TTGATGCCGATATGCCGGTTATTGTTGTTGCACCGAACAACGAATTGCTGGAAAAACTGAAATC

CAACATTGAAGAAGTTCGCGCGCGTGGCGGTCAGTTGTATGTCTTCGCCGATCAGGATGCGGGT

TTTGTAAGTAGCGATAACATGCACATCATCGAGATGCCGCATGTGGAAGAGGTGATTGCACCGA

TCTTCTACACCGTTCCGCTGCAGCTGCTGGCTTACCATGTCGCGCTGATCAAAGGCACCGACGT

TGACCAGCCGCGTAACCTGGCAAAATCGGTTACGGTTGAGTAA (SEQ ID NO: 38)

MCGIVGAIAQRDVAEILLEGLRRLEYRGYDSAGLAVVDAEGHMTRLRRLGKVQMLAQAA

EEHPLHGGTGIAHTRWATHGEPSEVNAHPHVSEHIVVVHNGIIENHEPLREELKARGYTFVSET

DTEVIAHLVNWELKQGGTLREAVLRAIPQLRGAYGTVIMDSRHPDTLLAARSGSPLVIGLGMGE

NFIASDQLALLPVTRRFIFLEEGDIAEITRRSVNIFDKTGAEVKRQDIESNLQYDAGDKGIYRH

YMQKEIYEQPNAIKNTLTGRISHGQVDLSELGPNADELLSKVEHIQILACGTSYNSGMVSRYWF

ESLAGIPCDVEIASEFRYRKSAVRRNSLMITLSQSGETADTLAGLRLSKELGYLGSLAICNVPG

SSLVRESDLALMTNAGTEIGVASTKAFTTQLTVLLMLVAKLSRLKGLDASIEHDIVHGLQALPS

RIEQMLSQDKRIEALAEDFSDKHHALFLGRGDQYPIALEGALKLKEISYIHAEAYAAGELKHGP

LALIDADMPVIVVAPNNELLEKLKSNIEEVRARGGQLYVFADQDAGFVSSDNMHIIEMPHVEEV

IAPIFYTVPLQLLAYHVALIKGTDVDQPRNLAKSVIVE* glmM AAC76208

(SEQ ID NO: 39)

ATGAGTAATCGTAAATATTTCGGTACCGATGGGATTCGTGGTCGTGTAGGGGATGCGCC

GATCACACCTGATTTTGTGCTTAAGCTGGGTTGGGCCGCGGGTAAAGTGCTGGCGCGCCACGGC

TCCCGTAAGATTATTATTGGTAAAGACACGCGTATTTCTGGCTATATGCTGGAGTCAGCACTGG

AAGCGGGTCTGGCGGCAGCGGGCCTTTCCGCACTCTTCACTGGCCCGATGCCAACACCGGCCGT

GGCTTATCTGACGCGTACCTTCCGCGCAGAGGCCGGAATTGTGATATCTGCATCGCATAACCCG

TTCTACGATAATGGCATTAAATTCTTCTCTATCGACGGCACCAAACTGCCGGATGCGGTAGAAG

AGGCCATCGAAGCGGAAATGGAAAAGGAGATCAGCTGCGTTGATTCGGCAGAACTGGGTAAAGC

CAGCCGTATCGTTGATGCCGCGGGTCGCTATATCGAGTTTTGCAAAGCCACGTTCCCGAACGAA

CTTAGCCTCAGTGAACTGAAGATTGTGGTGGATTGTGCAAACGGTGCGACTTATCACATCGCGC

-continued

CGAACGTGCTGCGCGAACTGGGGGCGAACGTTATCGCTATCGGTTGTGAGCCAAACGGTGTAAA

CATCAATGCCGAAGTGGGGGCTACCGACGTTCGCGCGCTCCAGGCTCGTGTGCTGGCTGAAAAA

GCGGATCTCGGTATTGCCTTCGACGGCGATGGCGATCGCGTGATTATGGTTGACCATGAAGGCA

ATAAAGTCGATGGCGATCAGATCATGTATATCATCGCGCGTGAAGGTCTTCGTCAGGGCCAGCT

GCGTGGTGGCGCTGTGGGTACATTGATGAGCAACATGGGGCTTGAACTGGCGCTGAAACAGTTA

GGAATTCCATTTGCGCGCGCGAAAGTGGGTGACCGCTACGTACTGGAAAAAATGCAGGAGAAAG

GCTGGCGTATCGGTGCAGAGAATTCCGGTCATGTGATCCTGCTGGATAAAACTACTACCGGTGA

CGGCATCGTTGCTGGCTTGCAGGTGCTGGCGGCGATGGCACGTAACCATATGAGCCTGCACGAC

CTTTGCAGCGGCATGAAAATGTTCCCGCAGATTCTGGTTAACGTACGTTACACCGCAGGTAGCG

GCGATCCACTTGAGCATGAGTCAGTTAAAGCCGTGACCGCAGAGGTTGAAGCTGCGCTGGGCAA

CCGTGGACGCGTGTTGCTGCGTAAATCCGGCACCGAACCGTTAATTCGCGTGATGGTGGAAGGC

GAAGACGAAGCGCAGGTGACTGAATTTGCACACCGCATCGCCGATGCAGTAAAAGCCGTTTAA (SEQ ID NO: 40)

MSNRKYFGTDGIRGRVGDAPITPDFVLKLGWAAGKVLARHGSRKIIIGKDTRISGYMLE

SALEAGLAAAGLSALFTGPMPTPAVAYLTRTFRAEAGIVISASHNPFYDNGIKFFSIDGTKLPD

AVEEAIEAEMEKEISCVDSAELGKASRIVDAAGRYIEFCKATFPNELSLSELKIVVDCANGATY

HIAPNVLRELGANVIAIGCEPNGVNINAEVGATDVRALQARVLAEKADLGIAFDGDGDRVIMVD

HEGNKVDGDQIMYIIAREGLRQGQLRGGAVGTLMSNMGLELALKQLGIPFARAKVGDRYVLEKM

QEKGWRIGAENSGHVILLDKITTGDGIVAGLQVLAAMARNHMSLHDLCSGMKMFPQILVNVRYT

AGSGDPLEHESVKAVTAEVEAALGNRGRVLLRKSGTEPLIRVMVEGEDEAQVTEFAHRIADAVK

AV* glmU AAC76753

(SEQ ID NO: 41)

ATGTTGAATAATGCTATGAGCGTAGTGATCCTTGCCGCAGGCAAAGGCACGCGCATGTA

TTCCGATCTTCCGAAAGTGCTGCATACCCTTGCCGGGAAAGCGATGGTTCAGCATGTCATTGAT

GCTGCGAATGAATTAGGCGCAGCGCACGTTCACCTGGTGTACGGTCACGGCGGCGATCTGCTAA

AACAGGCGCTGAAAGACGACAACCTTAACTGGGTGCTTCAGGCAGAGCAGCTGGGTACGGGTCA

TGCAATGCAGCAGGCCGCACCTTTCTTTGCCGATGATGAAGACATTTTAATGCTCTACGGCGAC

GTGCCGCTGATCTCTGTCGAAACACTCCAGCGTCTGCGTGATGCTAAACCGCAGGGTGGCATTG

GTCTGCTGACGGTGAAACTGGATGATCCGACCGGTTATGGACGTATCACCCGTGAAAACGGCAA

AGTTACCGGCATTGTTGAGCACAAAGATGCCACCGACGAGCAGCGTCAGATTCAGGAGATCAAC

ACCGGCATTCTGATTGCCAACGGCGCAGATATGAAACGCTGGCTGGCGAAGCTGACCAACAATA

ATGCTCAGGGCGAATACTACATCACCGACATTATTGCGCTGGCGTATCAGGAAGGGCGTGAAAT

CGTCGCCGTTCATCCGCAACGTTTAAGCGAAGTAGAAGGCGTGAATAACCGCCTGCAACTCTCC

CGTCTGGAGCGTGTTTATCAGTCCGAACAGGCTGAAAAACTGCTGTTAGCAGGCGTTATGCTGC

GCGATCCAGCGCGTTTTGATCTGCGTGGTACGCTAACTCACGGGCGCGATGTTGAAATTGATAC

TAACGTTATCATCGAGGGCAACGTGACTCTCGGTCATCGCGTGAAAATTGGCACCGGTTGCGTG

ATTAAAAACAGCGTGATTGGCGATGATTGCGAAATCAGTCCGTATACCGTTGTGGAAGATGCGA

ATCTGGCAGCGGCCTGTACCATTGGCCCGTTTGCCCGTTTGCGTCCTGGTGCTGAGTTGCTGGA

AGGTGCTCACGTCGGTAACTTCGTTGAGATGAAAAAAGCGCGTCTGGGTAAAGGCTCGAAAGCT

GGTCATCTGACTTACCTGGGCGATGCGGAAATTGGCGATAACGTTAACATCGGCGCGGGAACCA

TTACCTGCAACTACGATGGTGCGAATAAATTTAAGACCATTATCGGCGACGATGTGTTTGTTGG

-continued

TTCCGACACTCAGCTGGTGGCCCCGGTAACAGTAGGCAAAGGCGCGACCATTGCTGCGGGTACA

ACTGTGACGCGTAATGTCGGCGAAAATGCATTAGCTATCAGCCGTGTGCCGCAGACTCAGAAAG

AAGGCTGGCGTCGTCCGGTAAAGAAAAAGTGA (SEQ ID NO: 42)

MLNNAMSVVILAAGKGTRMYSDLPKVLHTLAGKAMVQHVIDAANELGAAHVHLVYGHGG

DLLKQALKDDNLNWVLQAEQLGTGHAMQQAAPFFADDEDILMLYGDVPLISVETLQRLRDAKPQ

GGIGLLTVKLDDPTGYGRITRENGKVTGIVEHKDATDEQRQIQEINTGILIANGADMKRWLAKL

TNNNAQGEYYITDIIALAYQEGREIVAVHPQRLSEVEGVNNRLQLSRLERVYQSEQAEKLLLAG

VMLRDPARFDLRGTLTHGRDVEIDINVIIEGNVTLGHRVKIGTGCVIKNSVIGDDCEISPYTVV

EDANLAAACTIGPFARLRPGAELLEGAHVGNFVEMKKARLGKGSKAGHLTYLGDAEIGDNVNIG

AGTITCNYDGANKFKTIIGDDVFVGSDTQLVAPVTVGKGATIAAGTTVTRNVGENALAISRVPQ

TQKEGWRRPVKKK*

GNE Q9Y223

(SEQ ID NO: 43)

ATGGAGAAGAACGGGAACAACCGAAAGCTCCGGGTTTGCGTTGCCACCTGCAACCGAGC

TGACTACTCCAAACTGGCCCCGATCATGTTCGGCATCAAGACAGAGCCCGCGTTCTTTGAGTTG

GACGTGGTGGTGCTCGGCTCCCACCTGATTGACGACTATGGAAACACATACCGCATGATTGAGC

AAGATGACTTTGACATTAACACCAGGCTCCACACGATTGTTAGAGGGGAAGATGAAGCGGCCAT

GGTAGAGTCGGTAGGCCTAGCGCTCGTGAAGCTACCGGACGTCCTCAATCGCCTGAAGCCCGAC

ATCATGATTGTTCACGGAGATCGATTTGACGCCCTTGCTCTGGCTACGTCTGCTGCCTTGATGA

ACATCCGCATCCTTCACATTGAAGGAGGCGAGGTCAGCGGGACCATTGATGACTCTATCAGACA

CGCCATAACAAAACTGGCTCACTACCATGTGTGCTGCACTAGAAGTGCAGAGCAGCACCTGATC

TCTATGTGCGAGGACCACGACCGCATCCTGTTGGCAGGCTGCCCTTCCTATGACAAACTGCTCT

CCGCCAAGAACAAAGACTATATGAGCATCATTCGGATGTGGCTAGGCGATGATGTAAAATGTAA

GGATTACATCGTTGCCCTGCAGCATCCCGTGACCACTGACATTAAGCATTCCATAAAGATGTTT

GAGCTAACACTGGATGCCCTGATCTCGTTTAACAAGAGGACCCTAGTTCTGTTTCCAAATATCG

ATGCAGGCAGCAAGGAGATGGTTCGAGTGATGCGGAAGAAGGGCATCGAGCATCACCCCAATTT

CCGTGCAGTCAAGCACGTCCCGTTTGACCAGTTCATACAGCTGGTCGCCCACGCTGGCTGCATG

ATTGGGAATAGCAGCTGCGGCGTGCGAGAGGTTGGCGCTTTCGGAACACCCGTGATCAACCTGG

GCACAAGGCAGATAGGAAGAGAAACCGGGGAGAATGTTCTTCATGTCAGGGATGCTGACACCCA

AGATAAAATATTGCAAGCACTACACCTCCAGTTCGGCAAACAGTACCCTTGCTCAAAGATATAT

GGGGATGGGAATGCTGTTCCAAGGATTTTAAAGTTTCTCAAATCCATTGACCTTCAAGAGCCAC

TACAGAAGAAATTCTGCTTCCCCCCTGTAAAGGAGAACATCTCTCAAGACATTGACCACATCCT

GGAAACTCTGAGTGCCTTGGCTGTTGATCTTGGCGGGACAAACCTGAGGGTGGCAATAGTTAGC

ATGAAGGGTGAAATCGTTAAGAAGTACACTCAGTTCAACCCTAAAACCTATGAAGAAAGGATTA

GTTTAATCCTGCAGATGTGTGTGGAAGCTGCCGCGGAAGCTGTGAAACTCAATTGCAGAATACT

GGGAGTAGGCATCTCCACAGGTGGCCGCGTGAATCCCCAGGAAGGAGTTGTGCTGCATTCAACC

AAGCTGATCCAGGAATGGAACTCCGTGGACCTCAGGACACCCCTCTCCGACACCCTGCATCTCC

CCGTGTGGGTGGACAATGACGGCAACTGTGCCGCCATGGCAGAGAGGAAGTTCGGCCAAGGAAA

AGGACAGGAGAACTTCGTGACGCTCATCACGGGGACAGGGATCGGTGGGGGGATCATCCACCAG

CACGAACTGATCCACGGCAGCTCCTTCTGCGCGGCGGAGCTCGGCCATCTCGTGGTGTCCCTGG

ACGGTCCTGACTGCTCCTGTGGAAGCCATGGGTGCATCGAAGCGTACGCCTCTGGAATGGCCTT

GCAGAGGGAAGCAAAGAAACTCCATGATGAGGACCTGCTCTTGGTGGAAGGGATGTCAGTACCA

AAAGACGAAGCTGTGGGTGCCCTCCATCTCATCCAGGCTGCCAAGCTGGGCAACGTGAAGGCCC

AGAGCATCTTACGAACAGCTGGAACTGCTTTGGGACTTGGGGTTGTGAACATCCTCCACACTAT

GAATCCTTCCCTGGTGATCCTGTCTGGAGTCCTGGCCAGTCACTACATCCACATCGTCAAGGAC

GTCATCCGCCAGCAAGCCTTGTCCTCCGTGCAGGATGTGGACGTGGTGGTGTCAGACTTGGTGG

ACCCGGCCCTGCTTGGCGCAGCCAGCATGGTTCTGGACTACACAACGCGCAGGATACACTAG (SEQ ID NO: 44)

MEKNGNNRKLRVCVATCNRADYSKLAPIMFGIKTEPAFFELDVVVLGSHLIDDYGNTYR

MIEQDDFDINTRLHTIVRGEDEAAMVESVGLALVKLPDVLNRLKPDIMIVHGDRFDALALATSA

ALMNIRILHIEGGEVSGTIDDSIRHAITKLAHYHVCCTRSAEQHLISMCEDHDRILLAGCPSYD

KLLSAKNKDYMSIIRMWLGDDVKCKDYIVALQHPVTTDIKHSIKMFELTLDALISFNKRTLVLF

PNIDAGSKEMVRVMRKKGIEHHPNFRAVKHVPFDQFIQLVAHAGCMIGNSSCGVREVGAFGTPV

INLGTRQIGRETGENVLHVRDADTQDKILQALHLQFGKQYPCSKIYGDGNAVPRILKFLKSIDL

QEPLQKKFCFPPVKENISQDIDHILETLSALAVDLGGTNLRVAIVSMKGEIVKKYTQFNPKTYE

ERISLILQMCVEAAAEAVKLNCRILGVGISTGGRVNPQEGVVLHSTKLIQEWNSVDLRTPLSDT

LHLPVWVDNDGNCAAMAERKFGQGKGQENFVTLITGTGIGGGIIHQHELIHGSSFCAAELGHLV

VSLDGPDCSCGSHGCIEAYASGMALQREAKKLHDEDLLLVEGMSVPKDEAVGALHLIQAAKLGN

VKAQSILRTAGTALGLGVVNILHTMNPSLVILSGVLASHYIHIVKDVIRQQALSSVQDVDVVVS

DLVDPALLGAASMVLDYTTRRIH*

NANS Q9NR45

(SEQ ID NO: 45)

ATGCCGCTGGAGCTGGAGCTGTGTCCCGGGCGCTGGGTGGGAGGTCAACACCCGTGCTT

CATCATTGCCGAGATCGGCCAGAACCACCAGGGCGACCTGGACGTAGCCAAGCGCATGATCCGC

ATGGCCAAGGAGTGTGGGGCTGATTGTGCTAAGTTCCAGAAGAGTGAGCTAGAATTTAAGTTTA

ATCGGAAAGCCTTGGAGAGGCCATACACCTCGAAGCATTCCTGGGGGAAAACGTACGGGGAGCA

CAAACGACATCTGGAGTTCAGCCATGACCAGTACAGGGAGCTGCAGAGGTACGCCGAGGAGGTT

GGGATCTTCTTCACTGCCTCTGGCATGGATGAGATGGCAGTTGAATTTCTGCATGAACTGAATG

TTCCATTTTTCAAAGTTGGATCTGGAGACACTAATAATTTTCCTTATCTGGAAAAGACAGCCAA

AAAAGGTCGCCCAATGGTGATCTCCAGTGGGATGCAGTCAATGGACACCATGAAGCAAGTTTAT

CAGATCGTGAAGCCCCTCAACCCCAACTTCTGCTTCTTGCAGTGTACCAGCGCATACCCGCTCC

AGCCTGAGGACGTCAACCTGCGGGTCATCTCGGAATATCAGAAGCTCTTTCCTGACATTCCCAT

AGGGTATTCTGGGCATGAAACAGGCATAGCGATATCTGTGGCCGCAGTGGCTCTGGGGGCCAAG

GTGTTGGAACGTCACATAACTTTGGACAAGACCTGGAAGGGGAGTGACCACTCGGCCTCGCTGG

AGCCTGGAGAACTGGCCGAGCTGGTGCGGTCAGTGCGTCTTGTGGAGCGTGCCCTGGGCTCCCC

AACCAAGCAGCTGCTGCCCTGTGAGATGGCCTGCAATGAGAAGCTGGGCAAGTCTGTGGTGGCC

AAAGTGAAAATTCCGGAAGGCACCATTCTAACAATGGACATGCTCACCGTGAAGGTGGGTGAGC

CCAAAGGCTATCCTCCTGAGGACATCTTTAATCTAGTGGGCAAGAAGGTCCTGGTCACTGTTGA

AGAGGATGACACCATCATGGAAGAATTGGTAGATAATCATGGCAAAAAAATCAAGTCTTAA (SEQ ID NO: 46)

MPLELELCPGRWVGGQHPCFIIAEIGQNHQGDLDVAKRMIRMAKECGADCAKFQKSELE

FKFNRKALERPYTSKHSWGKTYGEHKRHLEFSHDQYRELQRYAEEVGIFFTASGMDEMAVEFLH

ELNVPFFKVGSGDTNNFPYLEKTAKKGRPMVISSGMQSMDTMKQVYQIVKPLNPNFCFLQCTSA

YPLQPEDVNLRVISEYQKLFPDIPIGYSGHETGIAISVAAVALGAKVLERHITLDKTWKGSDHS

-continued

ASLEPGELAELVRSVRLVERALGSPTKQLLPCEMACNEKLGKSVVAKVKIPEGTILTMDMLTVK

VGEPKGYPPEDIFNLVGKKVLVTVEEDDTIMEELVDNHGKKIKS*

NANP Q8TBE9

(SEQ ID NO: 47)
ATGGGGCTGAGCCGCGTGCGGGCGGTTTTCTTTGACTTGGACAACACTCTCATCGACAC

GGCCGGGGCGAGCAGGAGAGGCATGTTGGAGGTGATAAAACTCTTACAATCAAAATACCATTAT

AAAGAAGAGGCTGAAATCATCTGTGATAAAGTTCAAGTTAAACTCAGCAAGGAATGTTTTCATC

CTTACAATACATGCATTACTGATTTAAGGACTTCACATTGGGAAGAAGCAATCCAGGAAACAAA

AGGTGGTGCAGCCAATAGAAAATTGGCTGAAGAATGTTATTTCCTTTGGAAATCTACACGTTTA

CAGCACATGACACTAGCAGAAGATGTCAAAGCCATGCTTACTGAACTTCGAAAGGAGGTCCGCC

TACTTCTATTAACGAATGGGGACAGACAGACCCAGAGGGAGAAGATTGAGGCTTGTGCCTGTCA

GTCCTATTTTGACGCTGTTGTTGTAGGTGGAGAGCAGAGAGAGGAGAAACCAGCACCGTCCATA

TTTTATTACTGCTGCAATCTTCTCGGAGTACAACCTGGGGACTGTGTGATGGTCGGTGACACAT

TAGAAACCGACATCCAAGGAGGCCTCAATGCAGGATTGAAAGCAACAGTCTGGATCAATAAAAA

TGGAATAGTGCCACTGAAGTCCTCCCCAGTTCCGCATTACATGGTTTCTTCTGTGCTAGAGTTA

CCTGCTCTCTTACAAAGTATAGACTGCAAAGTCAGTATGTCCACTTAA (SEQ ID NO: 48)
MGLSRVRAVFFDLDNTLIDTAGASRRGMLEVIKLLQSKYHYKEEAEIICDKVQVKLSKE

CFHPYNTCITDLRISHWEEAIQETKGGAANRKLAEECYFLWKSTRLQHMTLAEDVKAMLTELRK

EVRLLLLINGDRQTQREKIEACACQSYFDAVVVGGEQREEKPAPSIFYYCCNLLGVQPGDCVMV

GDTLETDIQGGLNAGLKATVWINKNGIVPLKSSPVPHYMVSSVLELPALLQSIDCKVSMST*

CMAS Q8NFW8

(SEQ ID NO: 49)
ATGGACTCGGTGGAGAAGGGTGCTGCTACATCAGTGTCCAACCCGCGTGGACGACCATC

CCGAGGCCGGCCTCCTAAGCTGCAGCGAAACTCTCGCGGCGGCCAGGGCCGAGGTGTGGAGAAG

CCCCCGCACCTGGCAGCCCTAATTCTGGCCCGGGGAGGCAGCAAAGGCATCCCCCTGAAGAACA

TTAAGCACCTGGCGGGGGTCCCGCTCATTGGCTGGGTCCTGCGTGCGGCCCTGGATTCAGGGGC

CTTCCAGAGTGTATGGGTTTCGACAGACCATGATGAAATTGAGAATGTGGCCAAACAATTTGGT

GCACAAGTTCATCGAAGAAGTTCTGAAGTTTCAAAAGACAGCTCTACCTCACTAGATGCCATCA

TAGAATTTCTTAATTATCATAATGAGGTTGACATTGTAGGAAATATTCAAGCTACTTCTCCATG

TTTACATCCTACTGATCTTCAAAAAGTTGCAGAAATGATTCGAGAAGAAGGATATGATTCTGTT

TTCTCTGTTGTGAGGCGCCATCAGTTTCGATGGAGTGAAATTCAGAAAGGAGTTCGTGAAGTGA

CCGAACCTCTGAATTTAAATCCAGCTAAACGGCCTCGTCGACAAGACTGGGATGGAGAATTATA

TGAAAATGGCTCATTTTATTTTGCTAAAAGACATTTGATAGAGATGGGTTACTTGCAGGGTGGA

AAAATGGCATACTACGAAATGCGAGCTGAACATAGTGTGGATATAGATGTGGATATTGATTGGC

CTATTGCAGAGCAAAGAGTATTAAGATATGGCTATTTTGGCAAAGAGAAGCTTAAGGAAATAAA

ACTTTTGGTTTGCAATATTGATGGATGTCTCACCAATGGCCACATTTATGTATCAGGTGACCAA

AAAGAAATAATATCTTATGATGTAAAAGATGCTATTGGGATAAGTTTATTAAAGAAAAGTGGTA

TTGAGGTGAGGCTAATCTCAGAAAGGGCCTGTTCAAAGCAGACGCTGTCATCTTTAAAACTGGA

TTGCAAAATGGAAGTCAGTGTATCAGACAAGCTAGCAGTTGTAGATGAATGGAGAAAAGAAATG

GGCCTGTGCTGGAAAGAAGTGGCATATCTTGGAAATGAAGTGTCTGATGAAGAGTGCTTGAAGA

-continued

GAGTGGGCCTAAGTGGCGCTCCTGCTGATGCCTGTTCTACTGCCCAGAAGGCTGTTGGATACAT

TTGCAAATGTAATGGTGGCCGTGGTGCCATCCGAGAATTTGCAGAGCACATTTGCCTACTAATG

GAAAAGGTTAATAATTCATGCCAAAAATAG (SEQ ID NO: 50)

MDSVEKGAATSVSNPRGRPSRGRPPKLQRNSRGGQGRGVEKPPHLAALILARGGSKGIP

LKNIKHLAGVPLIGWVLRAALDSGAFQSVWVSTDHDEIENVAKQFGAQVHRRSSEVSKDSSTSL

DAIIEFLNYHNEVDIVGNIQATSPCLHPTDLQKVAEMIREEGYDSVFSVVRRHQFRWSEIQKGV

REVTEPLNLNPAKRPRRQDWDGELYENGSFYFAKRHLIEMGYLQGGKMAYYEMRAEHSVDIDVD

IDWPIAEQRVLRYGYFGKEKLKEIKLLVCNIDGCLINGHIYVSGDQKEIISYDVKDAIGISLLK

KSGIEVRLISERACSKQTLSSLKLDCKMEVSVSDKLAVVDEWRKEMGLCWKEVAYLGNEVSDEE

CLKRVGLSGAPADACSTAQKAVGYICKCNGGRGAIREFAEHICLLMEKVNNSCQK*

The invention claimed is:

1. A method of producing a mammalian milk oligosaccharide (MMO) in a plant or plant part, comprising growing a plant comprising and expressing a recombinant MMO biosynthetic pathway sufficient to produce the MMO, wherein the pathway produces the MMO in the plant or plant part, wherein the pathway comprises recombinant enzymes:

a β1-4 galactosyltransferase (β1-4-GalT), which glycosylates glucose using UDP-galactose to make lactose; and a β1-3 N-acetylglucosaminyltransferase (1-3-GlcNAc), which generates lacto-N-triose (LNTII) through the transfer of GlcNAC from UDP-GlcNAc to the galactose in the lactose; and at least one of:

a β1-3-galactosyltransferase (β1-3-GalT) and a β1-4-galactosyltransferase (β1-4-GalT), which converts the LNTII to lacto-N-tetraose (LNT) and lacto-N-neotetraose (LNnT), respectively, wherein the plant is tobacco.

2. A method of claim 1, wherein the pathway comprises recombinant enzyme:

a α1-2-fucosyltransferase (α1-2-FucT) to produce lacto-N-fucopentaose I (LNFPI), a fucosylated pentasaccharide generated by the addition of an α-1,2-linked fucose to the terminal galactose in the lacto-N-tetraose (LNT).

3. The method of claim 1, wherein the pathway comprises recombinant enzyme:

a α2-3-sialyltransferase or a α2-6-sialyltransferase to add an α-2,6-linked or α-2,3-linked Neu5Ac to the lacto-N-neotetraose (LNnT) to produce sialyllacto-N-neotetraose d (LSTd) or sialyllacto-N-neotetraose c (LSTc), respectively.

4. The method of claim 1, wherein the plant is comprising and expressing a eukaryotic or prokaryotic nucleotide sugar biosynthetic pathway sufficient to increase the production of the MMO.

5. The method of claim 1, wherein the plant is further comprising and expressing a prokaryotic nucleotide sugar biosynthetic pathway sufficient to increase the production of the MMO, wherein the pathway comprises one, two or three of the following pathways and corresponding enzymes:

a) GDP-fucose pathway and enzymes: ManA, ManB, ManC, Gmd, and WcaG, b) UDP-galactose pathway and enzymes: pgi, pgm, GalU, and GalE, and c) UDP-GlcNAc pathway and enzymes: glmS, glmM, and glmU.

6. The method of claim 1, wherein the MMO is of a mammal selected from human, cow and goat, preferably wherein the MMO is a human milk oligosaccharide (HMO).

7. The method of claim 1, the plant comprising and expressing a plurality of recombinant MMO biosynthetic pathways sufficient to produce a plurality of different MMOs.

8. The method of claim 1, wherein:

the β1-4 galactosyltransferase (β1-4-GalT) is GalTPM1141;

the β1-3 N-acetylglucosaminyltransferase (β1-3-GnT) is NmLgtA;

the β1-3-galactosyltransferase (β1-3-GalT) is Cvβ3GalT;

the β1-4-galactosyltransferase (β1-4-GalT) is HP0826 or NmLgtB;

the α1-2-fucosyltransferase (α1-2-FucT) is Te2FT;

the α2-3-sialyltransferase is PmSt3); and the α2-6-sialyltransferase is St6.

9. The method of claim 1, wherein the plant or plant part is comprising and expressing of a β1-4-GalT, a β1-3-GlcNAcT, a β1-4-GalT, and a 1-3-GalT to produce LNnT and LNT.

10. The method of claim 1, wherein the plant or plant part is producing non-fucosylated neutral MMOs (nMMOs) comprising a lactose core with decorations of galactose and N-acetylglucosamine (GlcNAc).

11. The method of claim 1, wherein the plant or plant part is producing fucosylated MMOs, particularly comprising a lactose core decorated with one or more fucose moieties.

12. The method of claim 1, wherein the plant or plant part is comprising and expressing a β1-4-GalT, a β1-3-GlcNAcT, a β1-4-GalT, a β1-3-GalT and a α1-2-fucosyltransferase (α1-2-FucT) to produce lacto-N-fucopentaose I (LNFPI), a fucosylated pentasaccharide generated by the addition of an α-1,2-linked fucose to the terminal galactose in lacto-N-tetraose (LNT).

13. The method of claim 1, wherein the plant or plant part is producing fucosyllactose, lacto-N-tetraose or lacto-N-neotetraose, and lacto-N-fucopentaose I.

14. The method of claim 1, wherein to improve LNFPI yields, nucleotide sugar biosynthetic pathways (FIG. 1B) are expressed to increase the availability of GDP-fucose, UDP-galactose, and UDP-GlcNAc, combinatorially.

15. The method of claim 1, wherein the pathway comprises recombinant enzyme:

a α1-2-fucosyltransferase (α1-2-FucT) to produce lacto-N-fucopentaose I (LNFPI), a fucosylated pentasaccharide generated by the addition of an α-1,2-linked fucose to the terminal galactose in the lacto-N-tetraose (LNT), and the plant further comprises a prokaryotic GDP-fucose biosynthetic pathway comprising enzymes: ManA, ManB, ManC, Gmd and WcaG.

16. The method of claim 1, producing CMP-Neu5Ac.

17. The method of claim 1, wherein the plant or plant part is comprising and expressing a three gene bacterial pathway comprising genes: neuA, neuB, and neuC, or a four gene mammalian pathway comprising genes: GNE, NANS, NANP, and CMAS, which utilize UDP-GlcNAc as a precursor for the production of CMP-Neu5Ac.

18. The method of claim 1, wherein the plant or plant part is comprising and expressing a mammalian CMP-Neu5Ac pathway, comprising genes: GalTPM1141, NmLgtA, Cvβ3GalT, and Hp0826 for NmLgtB, and either PmSt3 or St6, to produce 3'SL, 6'SL and isomers of LST.

19. The method of claim 1, wherein the plant is a stable, transgenic plant, comprising constructs for the constitutive production of 2'FL and LNFPI.

20. The method of claim 1, further comprising isolating the MMO from the plant or plant part.

* * * * *

SEQUENCE LISTING

```
Sequence total quantity: 50
SEQ ID NO: 1           moltype = DNA  length = 843
FEATURE                Location/Qualifiers
source                 1..843
                       mol_type = genomic DNA
                       organism = Homo sapiens
SEQUENCE: 1
atgcccatga cgaactacgt aatatcacta agttcagcca gagagcgtag gcgtcatgtg  60
atgaacgaat tttccaagca ccacgttcca ttccagttct tcgacgcagt ttcaccatct  120
tctcagctgg atttcctcat tcaaagactt gtgcctaacc ttaacggaac aagccttaca  180
ggtggagaga aagggtgcct tatctcacat gtggccttat ggcataagtg catacaagac  240
aatctgccat atatagcaat cttcgaagat gacatactcc ttggcaggga cgcccgtgcc  300
ttcttggcag aggacgagtg gctattctct cgattcaact gtgacgatat cttcattatc  360
agactggaaa cttttcttca ggaaactatc tgcgaagcgc tccccaaccc cgtgtcatat  420
tgcggcaggg acttcttggc acttaaagat gaacaccttg ggacggctgg ttatatcatt  480
tcacttgggg ccgccaaata tttattggaa atctttaaga acatggagag taacaacatt  540
ttcccaatcg accacttgat tttcaatcgt ttcttagcgg gtgaagaact gatggtttac  600
cagctatctc ctgctctgtg cattcaagag cttcaattga acgaaaacga gtctttgttg  660
gacagccaac ttgagtccga acgcaagaac tatcgtcttg ctgagaaggc tagaaagaag  720
aaaacctggc gtgaaaaggt ttaccacatc ttcacaaagc cacaaagaat gcttaagaaa  780
agaaaggaaa gggctgagaa gaatgccaaa atgaaactca aatgcatcgt caaattcgag  840
taa                                                                 843

SEQ ID NO: 2           moltype = AA  length = 280
FEATURE                Location/Qualifiers
source                 1..280
                       mol_type = protein
                       organism = Homo sapiens
SEQUENCE: 2
MPMTNYVISL SSARERRRHV MNEFSKHHVP FQFFDAVSPS SQLDFLIQRL VPNLNGTSLT  60
GGEKGCLISH VALWHKCIQD NLPYIAIFED DILLGRDARA FLAEDEWLFS RFNCDDIFII  120
RLETFLQETI CEALPNPVSY CGRDFLALKD EHLGTAGYII SLGAAKYLLE IFKNMESNNI  180
FPIDHLIFNR FLAGEELMVY QLSPALCIQE LQLNENESLL DSQLESERKN YRLAEKARKK  240
KTWREKVYHI FTKPQRMLKK RKERAEKNAK MKLKCIVKFE                       280

SEQ ID NO: 3           moltype = DNA  length = 999
FEATURE                Location/Qualifiers
source                 1..999
                       mol_type = genomic DNA
                       organism = Homo sapiens
SEQUENCE: 3
atgcagcctt tagtcagcgt attgatttgc gcctacaacg tagaaaaata tttcgcccaa  60
tcattagccg ccgtcgtgaa tcaaacttgg tgcaacttgg atattttgat tgtcgatgac  120
ggctcgacag acggtacgct tgccattgcc aaggattttc aaaagcggga cagccgtatc  180
aaaatccttg cacaagctca aaattccggc ctgattccct ctttaaacat cgggctggac  240
gaattggcaa agtcgggggg gggggaatat attgcacgca ccgatgccga cgatattgcc  300
gcccccgact ggattgagaa aatcgtgggc gagatggaaa aagaccgcag catcatcgcg  360
atgggcgcgt ggctggaagt gttgtcggaa gaaaaggacg gcaaccggct ggcgcggcat  420
cacaggcacg gcaaaatttg gaaaaagccg acccgacacg aagatattgc cgactttttc  480
cctttcggca accccataca caacaacacg atgattatga ggcgcagcgt cattgacggc  540
ggtttgcgtt acaacaccga gcgggattgg gcggaagatt accaattttg gtacgatgtc  600
agcaaattgg gcaggctggc ttattatccc gaagccttgg tcaaataccg ccttcacgcc  660
aatcaggttt catccaaata cagcatccgc caacacgaaa tcgcgcaagg catccaaaaa  720
```

```
accgccagaa acgatttttt gcagtctatg ggttttaaaa cccggttcga cagccttgaa  780
taccgccaaa taaaagcagt agcgtatgaa ttgctggaga aacatttgcc ggaagaagat  840
tttgaacgcg cccgccggtt tttgtaccaa tgcttcaaac ggacggacac gccgcccgcc  900
ggcgcgtggc tggattttgc ggcagacggc aggatgcggc ggctgtttac cttgaggcaa  960
tacttcggca ttttgcaccg attgctgaaa aaccgttaa                         999

SEQ ID NO: 4           moltype = AA  length = 332
FEATURE                Location/Qualifiers
source                 1..332
                       mol_type = protein
                       organism = Homo sapiens
SEQUENCE: 4
MQPLVSVLIC AYNVEKYFAQ SLAAVVNQTW CNLDILIVDD GSTDGTLAIA KDFQKRDSRI  60
KILAQAQNSG LIPSLNIGLD ELAKSGGGEY IARTDADDIA APDWIEKIVG EMEKDRSIIA  120
MGAWLEVLSE EKDGNRLARH HRHGKIWKKP TRHEDIADFF PFGNPIHNNT MIMRRSVIDG  180
GLRYNTERDW AEDYQFWYDV SKLGRLAYYP EALVKYRLHA NQVSSKYSIR QHEIAQGIQK  240
TARNDFLQSM GFKTRFDSLE YRQIKAVAYE LLEKHLPEED FERARRFLYQ CFKRTDTPPA  300
GAWLDFAADG RMRRLFTLRQ YFGILHRLLK NR                                332

SEQ ID NO: 5           moltype = DNA  length = 789
FEATURE                Location/Qualifiers
source                 1..789
                       mol_type = genomic DNA
                       organism = Homo sapiens
SEQUENCE: 5
atggacacca tcatgattaa acgtccgctg gttagcgtta ttctgccggt gaataaaaac  60
aatccgcatc tggaagaagc aatccagagc attaaaaacc agacctataa agagctggaa  120
ctgatcatta ttgccaacaa ctgcgaggat aacttttata gcctgctgct gaaatatcag  180
gaccagaaaa ccaaaattat ccgcaccagc atcaaatatc tgccgtttag cctgaatctg  240
ggtgttcatc tgagccaggg tgaatatatt gcacgtatgg attcagatga tatcagcgtt  300
ctggatcgca ttgaaaaaca ggttaaacgc tttctgaata caccggaact gagcattctg  360
ggtagcaatg ttgaatatat caatgaagcc agcgaaagca ttggctatag caactatccg  420
ctggatcata gcagcattgt taatagcttt ccgtttcgtt gtaatctggc acatccgacc  480
attatggtta aaaaagaagt gattaccacg cttggtggct atatgtatgg tagcctgagc  540
gaagattatg atctgtggat tcgtgcaagc cgtcatggca atttcaaatt tagcaatatt  600
gatgaaccgc tgctgaagta ccgtattcat aaaggtcagg caaccaataa aagcaacgcc  660
tataacatct ttgcctttga tagcagcctg aaaatccgtg aatttctgct gaatggtaat  720
gtgcagtatc tgctgggtgc agcacgtggt ttttttgcat ttctgtatgt gcgtttcatc  780
aaaaaataa                                                          789

SEQ ID NO: 6           moltype = AA  length = 262
FEATURE                Location/Qualifiers
source                 1..262
                       mol_type = protein
                       organism = Homo sapiens
SEQUENCE: 6
MDTIMIKRPL VSVILPVNKN NPHLEEAIQS IKNQTYKELE LIIIANNCED NFYSLLLKYQ  60
DQKTKIIRTS IKYLPFSLNL GVHLSQGEYI ARMDSDDISV LDRIEKQVKR FLNTPELSIL  120
GSNVEYINEA SESIGYSNYP LDHSSIVNSF PFRCNLAHPT IMVKKEVITT LGGYMYGSLS  180
EDYDLWIRAS RHGNFKFSNI DEPLLKYRIH KGQATNKSNA YNIFAFDSSL KIREFLLNGN  240
VQYLLGAARG FFAFLYVRFI KK                                           262

SEQ ID NO: 7           moltype = DNA  length = 882
FEATURE                Location/Qualifiers
source                 1..882
                       mol_type = genomic DNA
                       organism = Homo sapiens
SEQUENCE: 7
atgattatcg ttcacctgtg cggtggcctg ggcaaccaga tgttccagta cgcagcgggt  60
ctggcagcag cgcaccgtat cggttctgaa gtgaaattcg acacccattg gttcgacgcg  120
acttgtctgc atcagggcct ggagctgcgc cgtgtttttg gtctggaact gccggagccg  180
tcctctaaag acctgcgtaa agttctgggc gcgtgtgttc atccggctgt tcgtcgtctg  240
ctggctggcc acttcctgca tggtctgcgc ccgaaatccc tggttatcca gccgcatttc  300
cactactgga ccggttttga gcacctgccg gacaacgttt acctggaggg ttactggcag  360
tccgaacgtt acttctctaa catcgcggat atcatccgtc agcagtttcg cttcgtggaa  420
ccgctggacc cgcacaacgc ggctctgatg gatgaaatgc agtctggtgt gtctgtttct  480
ctgcacattc gtcgcggcga ttactttaac aacccgcaga tgcgtcgcgt gcatggcgtg  540
gatctgagcg aatactaccc ggctgctgtt gcgaccatga tcgagaagac taacgcagaa  600
cgtttctacg ttttctccga cgatccgcag tgggttctgg agcatctgaa gctgccggtt  660
agctataccg ttgtggatca caaccgtggt gctgcgagct accgtgatat gcagctgatg  720
tccgcgtgcc gtcaccacat catcgcgaac tctaccttct cttggtgggg tgcgtggctg  780
aacccgcgtc cggataaagt tgttatcgca ccgcgccact ggtttaacgt tgacgttttt  840
gacacccgcg atctgtactg cccgggttgg attgttctgt aa                     882

SEQ ID NO: 8           moltype = AA  length = 293
FEATURE                Location/Qualifiers
source                 1..293
                       mol_type = protein
                       organism = Homo sapiens
```

```
SEQUENCE: 8
MIIVHLCGGL GNQMFQYAAG LAAAHRIGSE VKFDTHWFDA TCLHQGLELR RVFGLELPEP  60
SSKDLRKVLG ACVHPAVRRL LAGHFLHGLR PKSLVIQPHF HYWTGFEHLP DNVYLEGYWQ  120
SERYFSNIAD IIRQQFRFVE PLDPHNAALM DEMQSGVSVS LHIRRGDYFN NPQMRRVHGV  180
DLSEYYPAAV ATMIEKTNAE RFYVFSDDPQ WVLEHLKLPV SYTVVDHNRG AASYRDMQLM  240
SACRHHIIAN STFSWWGAWL NPRPDKVVIA PRHWFNVDVF DTRDLYCPGW IVL         293

SEQ ID NO: 9           moltype = DNA  length = 828
FEATURE                Location/Qualifiers
source                 1..828
                       mol_type = genomic DNA
                       organism = Homo sapiens
SEQUENCE: 9
atgcaaaacc acgttatcag cttagcttcc gccgcagaac gcagggcgca cattgccgat  60
accttcggca ggcacggcat cccgtttcag tttttcgacg cactgatgcc gtctgaaagg  120
ctggaacagg caatggcgga actcgtcccc ggcttgtcgg cgcacccccta tttgagcgga  180
gtggaaaaag cctgctttat gagccacgcc gtattgtgga agcaggcatt ggacgaaggt  240
ctgccgtata tcaccgtatt tgaggacgac gttttactcg gcgaaggtgc ggaaaaattc  300
cttgccgaag acgcttggct gcaagaacgc tttgacccgg ataccgcctt tatcgtccgc  360
ttggaaacga tgtttatgca cgtcctgacc tcgccctccg gcgtggcgga ttactgcggg  420
cgcgcctttc cgcttgttgga aagcgaacac tgggggacgg cgggctatat catttcccga  480
aaagcgatgc ggtttttcct ggacaggttt gccgccctgc cgcccgaagg gctgcacccc  540
gtcgatctga tgatgttcag cgattttttc gacagggaag gaatgccggt ttgccagctc  600
aatcccgcct tgtgcgccca agagctgcat tatgccaagt ttcacgacca aaacagcgca  660
ttgggcagcc tgatcgaaca cgaccgcctc ctgaaccgca aacagcaaag gcgcgattcc  720
cccgccaaca cattcaaaca ccgcctgatc cgcgccttga ccaaaatcag cagggaaagg  780
gaaaaacgcc ggcaaaggcg cgaacagttc attgtgcctt tccaataa              828

SEQ ID NO: 10          moltype = AA  length = 275
FEATURE                Location/Qualifiers
source                 1..275
                       mol_type = protein
                       organism = Homo sapiens
SEQUENCE: 10
MQNHVISLAS AAERRAHIAD TFGRHGIPFQ FFDALMPSER LEQAMAELVP GLSAHPYLSG  60
VEKACFMSHA VLWKQALDEG LPYITVFEDD VLLGEGAEKF LAEDAWLQER FDPDTAFIVR  120
LETMFMHVLT SPSGVADYCG RAFPLLESEH WGTAGYIISR KAMRFFLDRF AALPPEGLHP  180
VDLMMFSDFF DREGMPVCQL NPALCAQELH YAKFHDQNSA LGSLIEHDRL LNRKQQRRDS  240
PANTFKHRLI RALTKISRER EKRRQRREQF IVPFQ                             275

SEQ ID NO: 11          moltype = DNA  length = 822
FEATURE                Location/Qualifiers
source                 1..822
                       mol_type = genomic DNA
                       organism = Homo sapiens
SEQUENCE: 11
atgcgtgttt ttgccatttc tttaaatcaa aaagtgtgcg atacatttgg tttagttttt  60
agagacacca caactttact caatagcatc aatgccaccc accaccaagc gcaaattttt  120
gatgcgattt attctaaaac ttttgaaggc gggttgcacc ccttagtgaa aaagcattta  180
cacccttatt tcatcacgca aaacatcaaa gacatgggga ttacaaccaa tctcatcagt  240
gaggtttcta agttttatta cgctttaaaa taccatgcga agtttatgag cttgggggag  300
cttgggtgct atgcgagtca ttattccttg tgggaaaaat gcatagaact caatgaagcg  360
atctgtattt tagaagacga tataaccttg aaagaggatt ttaaagaggg cttggatttt  420
ttagaaaaac acatccaaga gttaggctat atccgcttga tgcatttatt gtatgatgcc  480
agtgtaaaaa gtgagccatt gagccataaa aaccacgaga tacaagagcg tgtggggatc  540
attaaagctt atagcgaagg ggtggggact caaggctatg tgatcacgcc taagattgcc  600
aaagtttttt tgaaatgcag ccgaaaatgg gttgttcctg tggatacgat aatggacgct  660
acttttatcc atggcgtgaa aaatctggtg ttacaacctt ttgtgatcgc tgatgatgag  720
caaatctcta cgatagcacg aaaagaagaa ccttatagcc ctaaaatcgc cttaatgaga  780
gaactccatt ttaaatattt gaaatattgg cagtttgtat aa                    822

SEQ ID NO: 12          moltype = AA  length = 273
FEATURE                Location/Qualifiers
source                 1..273
                       mol_type = protein
                       organism = Homo sapiens
SEQUENCE: 12
MRVFAISLNQ KVCDTFGLVF RDTTTLLNSI NATHHQAQIF DAIYSKTFEG GLHPLVKKHL  60
HPYFITQNIK DMGITTNLIS EVSKFYYALK YHAKFMSLGE LGCYASHYSL WEKCIELNEA  120
ICILEDDITL KEDFKEGLDF LEKHIQELGY IRLMHLLYDA SVKSEPLSHK NHEIQERVGI  180
IKAYSEGVGT QGYVITPKIA KVFLKCSRKW VVPVDTIMDA TFIHGVKNLV LQPFVIADDE  240
QISTIARKEE PYSPKIALMR ELHFKYLKYW QFV                               273

SEQ ID NO: 13          moltype = DNA  length = 834
FEATURE                Location/Qualifiers
source                 1..834
                       mol_type = genomic DNA
                       organism = Homo sapiens
SEQUENCE: 13
```

```
atggataaat ttgccgaaca tgaaattccg aaagccgtta ttgttgcagg taatggtgaa  60
agcctgagcc agattgatta tcgtctgctg ccgaaaaatt atgatgtgtt tcgctgcaat  120
cagttttatt ttgaagaacg ctattttctg ggcaataaaa ttaaagccgt gtttttttaca  180
ccgggtgttt ttctggaaca gtattatacc ctgtatcatc tgaaacgcaa taatgaatat  240
tttgtggata atgtgattct gagcagcttt aatcatccga ccgttgatct ggaaaaaagc  300
cagaaaattc aggccctgtt tattgatgtg attaatggct atgaaaaata tctgagcaaa  360
ctgaccgcct ttgatgttta tctgcgctat aaagaactgt atgaaaatca gcgtattacc  420
agcggtgttt atatgtgtgc agttgcaatt gcaatgggct ataccgatat ttatctgacc  480
ggcattgatt tttatcaggc cagcgaagaa aattatgcct ttgataataa aaaaccgaat  540
attattcgcc tgctgccgga ttttcgcaaa gaaaaaaccc tgtttagcta tcatagcaaa  600
gatattgatc tggaagccct gagctttctg cagcagcatt atcatgtgaa tttttatagc  660
attagcccga tgagtccgct gagcaaacat tttccgattc cgaccgtgga agatgattgt  720
gaaaccacct ttgttgcacc gctgaaagaa aattatatta atgatattct gctgcctccg  780
cattttgtgt atgaaaaact gggcgtcgac aagcttgcgg ccgcactcga gtga        834
```

```
SEQ ID NO: 14           moltype = AA  length = 277
FEATURE                 Location/Qualifiers
source                  1..277
                        mol_type = protein
                        organism = Homo sapiens
SEQUENCE: 14
MDKFAEHEIP KAVIVAGNGE SLSQIDYRLL PKNYDVFRCN QFYFEERYFL GNKIKAVFFT  60
PGVFLEQYYT LYHLKRNNEY FVDNVILSSF NHPTVDLEKS QKIQALFIDV INGYEKYLSK  120
LTAFDVYLRY KELYENQRIT SGVYMCAVAI AMGYTDIYLT GIDFYQASEE NYAFDNKKPN  180
IIRLLPDFRK EKTLFSYHSK DIDLEALSFL QQHYHVNFYS ISPMSPLSKH FPIPTVEDDC  240
ETTFVAPLKE NYINDILLPP HFVYEKLGVD KLAAALE                            277
```

```
SEQ ID NO: 15           moltype = DNA  length = 1116
FEATURE                 Location/Qualifiers
source                  1..1116
                        mol_type = genomic DNA
                        organism = Homo sapiens
SEQUENCE: 15
atgggcttga aaaaggcttg tttgaccgtg ttgtgtttga ttgtttttg tttcgggata  60
ttttatacat ttgaccgggt aaatcagggg gaaaggaatg cggtttccct gctgaaggag  120
aaactttca atgaagaggg ggaaccggtc aatctgattt tctgttatac catattgcag  180
atgaaggtgg cggaaaggat tatggcgcag catccgggcg agcggtttta tgtggtgctg  240
atgtctgaaa acaggaatga aaaatacgat tattatttca atcagataaa ggataaggcg  300
gagcgggcgt actttttcca cctgccctac ggtttgaaca aatcgtttaa tttcattccg  360
acgatggcgg agctgaaggt aaagtcgatg ctgctgccga aagtcaagcg gatttatttg  420
gcaagtttgg aaaaagtcag cattgccgcc tttttgagca cttacccgga tgcggaaatc  480
aaaacctttg acgacgggac aggcaattta attcaaagca gcagctattt gggcgatgag  540
ttttctgtaa acgggacgat caagcggaat tttgcccgga tgatgatcgg agattggagc  600
atcgccaaaa cccgcaatgc ttccgacgag cattacacga tattcaaggg tttgaaaaac  660
attatggacg acggccgccg caagatgact tacctgccgc tgttcgatgc gtccgaactg  720
aagacggggg acgaaacggg cggcacggtg cggatacttt tgggttcgcc cgacaaagag  780
atgaaggaaa tttcggaaaa ggcggcaaaa aacttcaaaa tacaatatgt cgcgccgcat  840
ccccgccaaa cctacgggct ttccggcgta accacattaa attcgcccta tgtcatcgaa  900
gactatattt tgcgcgagat taagaaaaac ccgcatacga ggtatgaaat ttataccttt  960
ttcagcggcg cggcgttgac gatgaaggat ttcccaatg tgcacgttta cgcattgaaa  1020
ccggcttccc ttccggaaga ttattggctc aagccggtgt atgccctgtt tacccaatcc  1080
ggcatcccga ttttgacatt tgacgataaa aattaa                            1116
```

```
SEQ ID NO: 16           moltype = AA  length = 371
FEATURE                 Location/Qualifiers
source                  1..371
                        mol_type = protein
                        organism = Homo sapiens
SEQUENCE: 16
MGLKKACLTV LCLIVFCFGI FYTFDRVNQG ERNAVSLLKE KLFNEEGEPV NLIFCYTILQ  60
MKVAERIMAQ HPGERFYVVL MSENRNEKYD YYFNQIKDKA ERAYFFHLPY GLNKSFNFIP  120
TMAELKVKSM LLPKVKRIYL ASLEKVSIAA FLSTYPDAEI KTFDDGTGNL IQSSSYLGDE  180
FSVNGTIKRN FARMMIGDWS IAKTRNASDE HYTIFKGLKN IMDDGRRKMT YLPLFDASEL  240
KTGDETGGTV RILLGSPDKE MKEISEKAAK NFKIQYVAPH PRQTYGLSGV TTLNSPYVIE  300
DYILREIKKN PHTRYEIYTF FSGAALTMKD FPNVHVYALK PASLPEDYWL KPVYALFTQS  360
GIPILTFDDK N                                                        371
```

```
SEQ ID NO: 17           moltype = DNA  length = 1545
FEATURE                 Location/Qualifiers
source                  1..1545
                        mol_type = genomic DNA
                        organism = Homo sapiens
SEQUENCE: 17
atgaaaaact ttttattatt aactttaata ttacttactg cttgtaataa ttcagaagaa  60
aatacacaat ctattattaa aaatgatatt aataaaacta ttattgatga ggagtatgtt  120
aatttagagc caattaatca atcaaacatc tcttttacaa aacactcttg ggtacaaact  180
tgtggtacgc aacaactatt aacagaacaa aataaagagt caatatcatt atctgtagtg  240
gcgccacgat tagatgacga tgaaaagtac tgctttgatt ttaatggtgt tagtaataaa  300
ggtgaaaaat atataacaaa agtaacatta aacgtagtgg ctccatcttt agaggtttat  360
```

```
gttgatcatg catctcttcc aactcttcag cagctaatgg atattattaa atcggaagaa  420
gaaaatccta cagcacaaag atatatagct tgggggagaa tagttccgac tgatgagcaa  480
atgaaagagt taaatattac atcgtttgca ttgataaata accatacacc agctgactta  540
gtacaagaaa ttgttaagca agcacaaaca aagcatagat tgaatgttaa acttagctct  600
aacactgctc attcatttga taatttagtg ccaatactaa aagaattaaa ttcgtttaat  660
aacgttacgg taacaaatat agatttatat gatgatggtt cagcagaata tgtaaattta  720
tataactgga gagatacatt aaataaaaca gataatttaa aaattggtaa agattatctt  780
gaggatgtca ttaatggtat caatgaagac acttcaaata caggaacatc atctgtttat  840
aactggcaaa aactatatcc agctaactac catttttttaa gaaaagatta tttaacttta  900
gaaccatcat tacatgagtt acgagactat attggtgata gtttaaagca aatgcaatgg  960
gatggtttca aaaaattcaa tagcaaacaa caagaattat tcttatcgat tgttaatttt  1020
gacaaacaaa aattacaaaa tgaatataat tcatctaatt taccaaactt tgtgtttaca  1080
ggtacgactg tatgggctgg taaccatgaa agagagtatt atgcgaaaca acaaattaat  1140
gtcattaata atgcaattaa tgaatcgagc ccacattatt taggcaatag ttatgatttg  1200
ttcttcaaag gtcaccctgg tggcggtatc attaatacat taataatgca aaactatcct  1260
tcaatggttg atattccatc aaaaatatca tttgaagttt tgatgatgac agatatgctt  1320
cctgatgcag ttgctggtat agcgagctct ttatatttca cgataccagc tgaaaaaatt  1380
aaatttatag tttttacatc gacagaaact ataactgatc gtgaaactgc tttgagaagt  1440
cctttagttc aagtaatgat aaaactaggt attgtaaaag aagagaatgt actttttttgg  1500
gctgatctgc caaattgtga aacaggtgtt tgtattgcag tctag              1545

SEQ ID NO: 18          moltype = AA  length = 514
FEATURE                Location/Qualifiers
source                 1..514
                       mol_type = protein
                       organism = Homo sapiens
SEQUENCE: 18
MKNFLLLTLI LLTACNNSEE NTQSIIKNDI NKTIIDEEYV NLEPINQSNI SFTKHSWVQT  60
CGTQQLLTEQ NKESISLSVV APRLDDDEKY CFDFNGVSNK GEKYITKVTL NVVAPSLEVY  120
VDHASLPTLQ QLMDIIKSEE ENPTAQRYIA WGRIVPTDEQ MKELNITSFA LINNHTPADL  180
VQEIVKQAQT KHRLNVKLSS NTAHSFDNLV PILKELNSFN NVTVTNIDLY DDGSAEYVNL  240
YNWRDTLNKT DNLKIGKDYL EDVINGINED TSNTGTSSVY NWQKLYPANY HFLRKDYLTL  300
EPSLHELRDY IGDSLKQMQW DGFKKFNSKQ QELFLSIVNF DKQKLQNEYN SSNLPNFVFT  360
GTTVWAGNHE REYYAKQQIN VINNAINESS PHYLGNSYDL FFKGHPGGGI INTLIMQNYP  420
SMVDIPSKIS FEVLMMTDML PDAVAGIASS LYFTIPAEKI KFIVFTSTET ITDRETALRS  480
PLVQVMIKLG IVKEENVLFW ADLPNCETGV CIAV                              514

SEQ ID NO: 19          moltype = DNA  length = 1650
FEATURE                Location/Qualifiers
source                 1..1650
                       mol_type = genomic DNA
                       organism = Homo sapiens
SEQUENCE: 19
atgaaaaaca tcaatccaac gcagaccgct gcctggcagg cactacagaa acacttcgat  60
gaaatgaaag acgttacgat cgccgatctt tttgctaaag acggcgatcg tttttctaag  120
ttctccgcaa ccttcgacga tcagatgctg gtggattact ccaaaaaccg catcactgaa  180
gagacgctgg cgaaattaca ggatctggcg aaagagtgcg atctggcggg cgcgattaag  240
tcgatgttct ctggcgagaa gatcaaccgc actgaaaacc gcgccgtgct gcacgtagcg  300
ctgcgtaacc gtagcaatac cccgattttg gttgatggca aagacgtaat gccggaagtc  360
aacgcggtgc tggagaagat gaaaaccttc tcagaagcga ttatttccgg tgagtggaaa  420
ggttataccg gcaaagcaat cactgacgta gtgaacatcg ggatcggcgg ttctgacctc  480
ggcccataca tggtgaccga agctctgcgt ccgtacaaaa accacctgaa catgcacttt  540
gtttctaacg tcgatgggac tcacatcgcg gaagtgctga aaaaagtaaa cccggaaacc  600
acgctgttct tggtagcatc taaaaccttc accactcagg aaactatgac caacgcccat  660
agcgcgcgtg actggttcct gaaagcggca ggtgatgaaa aacacgttgc aaaacacttt  720
gcggcgcttt ccaccaatgc caaagccgtt ggcgagtttg gtattgatac tgccaacatg  780
ttcgagttct gggactgggt tggcggccgt tactctttgt ggtcagcgat tggcctgtcg  840
attgttctct ccatcggctt tgataacttc gttgaactgc tttccggcgc acacgcgatg  900
gacaagcatt tctccaccac gcctgccgag aaaaacctgc ctgtactgct ggcgctgatt  960
ggcatctggt acaacaattt ctttggtgcg gaaactgaag cgattctgcc gtatgaccag  1020
tatatgcacc gtttcgcggc gtacttccag cagggcaata tggagtccaa cggtaagtat  1080
gttgaccgta acggtaacgt tgtggattac cagactggcc cgattatctg ggggtgaacca  1140
ggcactaacg gtcagcacgc gttctaccag ctgatccacc agggaaccaa aatggtaccg  1200
tgcgatttca tcgctccggc tatcacccat aacccgctct ctgatcatca ccagaaactg  1260
ctgtctaact tcttcgccca gaccgaagcg ctggcgtttg gtaaatcccg cgaagtggtt  1320
gagcaggaat atcgtgatca gggtaaagat ccggcaacgc ttgactacgt ggtgccgttc  1380
aaagtattcg aaggtaaccg cccgaccaac tccatcctgc tgcgtgaaat cactccgttc  1440
agcctgggtg cgttgattgc gctgtatgag cacaaaatct ttactcaggg cgtgatcctg  1500
aacatcttca ccttcgacca gtggggcgtg gaactgggta aacagctggc gaaccgtatt  1560
ctgccagagc tgaaagatga taaagaaatc agcagccacg atagctcgac caatggtctg  1620
attaaccgct ataaagcgtg gcgcggttaa                                  1650

SEQ ID NO: 20          moltype = AA  length = 549
FEATURE                Location/Qualifiers
source                 1..549
                       mol_type = protein
                       organism = Homo sapiens
SEQUENCE: 20
MKNINPTQTA AWQALQKHFD EMKDVTIADL FAKDGDRFSK FSATFDDQML VDYSKNRITE  60
```

-continued

```
ETLAKLQDLA KECDLAGAIK SMFSGEKINR TENRAVLHVA LRNRSNTPIL VDGKDVMPEV  120
NAVLEKMKTF SEAIISGEWK GYTGKAITDV VNIGIGGSDL GPYMVTEALR PYKNHLNMHF  180
VSNVDGTHIA EVLKKVNPET TLFLVASKTF TTQETMTNAH SARDWFLKAA GDEKHVAKHF  240
AALSTNAKAV GEFGIDTANM FEFWDWVGGR YSLWSAIGLS IVLSIGFDNF VELLSGAHAM  300
DKHFSTTPAE KNLPVLLALI GIWYNNFFGA ETEAILPYDQ YMHRFAAYFQ QGNMESNGKY  360
VDRNGNVVDY QTGPIIWGEP GTNGQHAFYQ LIHQGTKMVP CDFIAPAITH NPLSDHHQKL  420
LSNFFAQTEA LAFGKSREVV EQEYRDQGKD PATLDYVVPF KVFEGNRPTN SILLREITPF  480
SLGALIALYE HKIFTQGVIL NIFTFDQWGV ELGKQLANRI LPELKDDKEI SSHDSSTNGL  540
INRYKAWRG                                                          549

SEQ ID NO: 21           moltype = DNA  length = 1641
FEATURE                 Location/Qualifiers
source                  1..1641
                        mol_type = genomic DNA
                        organism = Homo sapiens
SEQUENCE: 21
atggcaatcc acaatcgtgc aggccaacct gcacaacaga gtgatttgat taacgtcgcc  60
caactgacgg cgcaatatta tgtactgaaa ccagaagcag ggaatgcgga gcacgcggtg  120
aaattcggta cttccggtca ccgtggcagt gcagcgcgcc acagctttaa cgagccgcac  180
attctggcga tcgctcaggc aattgctgaa gaacgtgcga aaaacggcat cactggccct  240
tgctatgtgg gtaaagatac tcacgccctg tccgaacctg cattcatttc cgttctggaa  300
gtgctggcag cgaacggcgt tgatgtcatt gtgcaggaaa acaatggctt caccccgacg  360
cctgccgttt ccaatgccat cctggttcac aataaaaaag gtggcccgct ggcagacggt  420
atcgtgatta caccgtccca taacccgccg gaagatggtg gaatcaaata caatccgcca  480
aatggtggcc cggctgatac caacgtcact aaagtggtgg aagacagggc caacgcactg  540
ctggccgatg gcctgaaagg cgtgaagcgt atctccctcg acgaagcgat ggcatccggt  600
catgtgaaag agcaggatct ggtgcagccg ttcgtggaag gtctggccga tatcgttgat  660
atggccgcga ttcagaaagc gggcctgacg ctgggcgttg atccgctggg cggttccggt  720
atcgaatact ggaagcgtat tggcgagtat tacaacctca acctgactat cgttaacgat  780
caggtcgatc aaaccttccg ctttatgcac cttgataaag acggcgcgat ccgtatggac  840
tgctcctccg agtgtgcgat ggcgggcctg ctggcactgc gtgataagtt cgatctggcg  900
tttgctaacg acccggatta tgaccgtcac ggtatcgtca ctccggcagg tttgatgaat  960
ccgaaccact acctggcggt ggcaatcaat tacctgttcc agcatcgtcc gcagtggggc  1020
aaagatgttg ccgtcggtaa aacgctggtt tcatctgcga tgatcgaccg tgtggtcaac  1080
gacttgggcc gtaaactggt agaagtcccg gtaggtttca aatggtttgt cgatggtctg  1140
ttcgacggca gcttcggctt tggcggcgaa gagagtgcag gggcttcctt cctgcgtttc  1200
gacggcacgc cgtggtccac cgacaaagac ggcatcatca tgtgtctgct ggcggcggaa  1260
atcaccgctg tcaccggtaa gaacccgcag gaacactaca acgaactggc aaaacgcttt  1320
ggtgcgccga gctacaaccg tttgcaggca gctgcgactt ccgcacaaaa agcggcgctg  1380
tctaagctgt ctccggaaat ggtgagcgcc agcaccctgg caggtgaccc gatcaccgcg  1440
cgcctgactg ctgctccggg caacggtgct tctattggcg gtctgaaagt gatgactgac  1500
aacggctggt tcgccgcgcg tccgtcaggc acggaagacg catataagat ctactgcgaa  1560
agcttcctcg gtgaagaaca tcgcaagcag attgagaaag aagcggttga gattgttagc  1620
gaagttctga aaaacgcgta a                                            1641

SEQ ID NO: 22           moltype = AA  length = 546
FEATURE                 Location/Qualifiers
source                  1..546
                        mol_type = protein
                        organism = Homo sapiens
SEQUENCE: 22
MAIHNRAGQP AQQSDLINVA QLTAQYYVLK PEAGNAEHAV KFGTSGHRGS AARHSFNEPH  60
ILAIAQAIAE ERAKNGITGP CYVGKDTHAL SEPAFISVLE VLAANGVDVI VQENNGFTPT  120
PAVSNAILVH NKKGGPLADG IVITPSHNPP EDGGIKYNPP NGGPADTNVT KVVEDRANAL  180
LADGLKGVKR ISLDEAMASG HVKEQDLVQP FVEGLADIVD MAAIQKAGLT LGVDPLGGSG  240
IEYWKRIGEY YNLNLTIVND QVDQTFRFMH LDKDGAIRMD CSSECAMAGL LALRDKFDLA  300
FANDPDYDRH GIVTPAGLMN PNHYLAVAIN YLFQHRPQWG KDVAVGKTLV SSAMIDRVVN  360
DLGRKLVEVP VGFKWFVDGL FDGSFGFGGE ESAGASFLRF DGTPWSTDKD GIIMCLLAAE  420
ITAVTGKNPQ EHYNELAKRF GAPSYNRLQA AATSAQKAAL SKLSPEMVSA STLAGDPITA  480
RLTAAPGNGA SIGGLKVMTD NGWFAARPSG TEDAYKIYCE SFLGEEHRKQ IEKEAVEIVS  540
EVLKNA                                                             546

SEQ ID NO: 23           moltype = DNA  length = 909
FEATURE                 Location/Qualifiers
source                  1..909
                        mol_type = genomic DNA
                        organism = Homo sapiens
SEQUENCE: 23
atggctgcca ttaatacgaa agtcaaaaaa gccgttatcc ccgttgcggg attaggaacc  60
aggatgttgc cggcgacgaa agccatcccg aaagagatgc tgccacttgt cgataagcca  120
ttaattcaat acgtcgtgaa tgaatgtatt gcggctggca ttactgaaat tgtgctggtt  180
acacactcat ctaaaaactc tattgaaaac cactttgata ccagttttga actggaagca  240
atgctggaaa aacgtgtaaa acgtcaactg cttgatgaag tgcagtctat ttgtccaccg  300
cacgtgacta ttatgcaagt tcgtcagggt ctggcgaaag gcctgggaca cgcggtattg  360
tgtgctcacc cggtagtggg tgatgaaccg gtagctgtta ttttgcctga tgttattctg  420
gatgaatatg aatccgattt gtcacaggat aacctggcag agatgatccg ccgctttgat  480
gaaacgggtc atagccagat catggttgaa ccggttgctg atgtgaccgc atatggcgtt  540
gtggattgca aaggcgttga attagcgccg ggtgaaagcg taccgatggt tggtgtggta  600
gaaaaaccga aagcggatgt tgcgccgtct aatctcgcta ttgtgggtcg ttacgtactt  660
```

```
agcgcggata tttggccgtt gctggcaaaa acccctccgg gagctggtga tgaaattcag  720
ctcaccgacg caattgatat gctgatcgaa aaagaaacgg tggaagccta tcatatgaaa  780
gggaagagcc atgactgcgg taataaatta ggttacatgc aggccttcgt tgaatacggt  840
attcgtcata acacccttgg cacggaattt aaagcctggc ttgaagaaga gatgggcatt  900
aagaagtaa                                                          909

SEQ ID NO: 24          moltype = AA  length = 302
FEATURE                Location/Qualifiers
source                 1..302
                       mol_type = protein
                       organism = Homo sapiens
SEQUENCE: 24
MAAINTKVKK AVIPVAGLGT RMLPATKAIP KEMLPLVDKP LIQYVVNECI AAGITEIVLV  60
THSSKNSIEN HFDTSFELEA MLEKRVKRQL LDEVQSICPP HVTIMQVRQG LAKGLGHAVL  120
CAHPVVGDEP VAVILPDVIL DEYESDLSQD NLAEMIRRFD ETGHSQIMVE PVADVTAYGV  180
VDCKGVELAP GESVPMVGVV EKPKADVAPS NLAIVGRYVL SADIWPLLAK TPPGAGDEIQ  240
LTDAIDMLIE KETVEAYHMK GKSHDCGNKL GYMQAFVEYG IRHNTLGTEF KAWLEEEMGI  300
KK                                                                 302

SEQ ID NO: 25          moltype = DNA  length = 1017
FEATURE                Location/Qualifiers
source                 1..1017
                       mol_type = genomic DNA
                       organism = Homo sapiens
SEQUENCE: 25
atgagagttc tggttaccgg tggtagcggt tacattggaa gtcatacctg tgtgcaatta  60
ctgcaaaacg gtcatgatgt catcattctt gataacctct gtaacagtaa gcgcagcgta  120
ctgcctgtta tcgagcgttt aggcggcaaa catccaacgt ttgttgaagg cgatattcgt  180
aacgaagcgt tgatgaccga gatcctgcac gatcacgcta tcgacaccgt gatccacttc  240
gccgggctga aagccgtggg cgaatcggta caaaaaccgc tggaatatta cgacaacaat  300
gtcaacggca ctctgcgcct gattagcgcc atgcgcgccg ctaacgtcaa aaactttatt  360
tttagctcct ccgccaccgt ttatggcgat cagcccaaaa ttccatacgt tgaaagcttc  420
ccgaccggca caccgcaaag cccttacggc aaaagcaagc tgatggtgga acagatcctc  480
accgatctgc aaaaagccca gccggactgg agcattgccc tgctgcgcta cttcaacccg  540
gttggcgcgc atccgtcggg cgatatgggc gaagatccgc aaggcattcc gaataacctg  600
atgccataca tcgcccaggt tgctgtaggc cgtcgcgact cgctggcgat ttttggtaac  660
gattatccga ccgaagatgg tactggcgta cgcgattaca tccacgtaat ggatctggcg  720
gacggtcacg tcgtggcgat ggaaaaactg gcgaacaagc caggcgtaca catctacaac  780
ctcggcgctg gcgtaggcaa cagcgtgctg gacgtggtta atgccttcag caaagcctgc  840
ggcaaaccgg ttaattatca ttttgcaccg cgtcgcgagg gcgaccttcc ggcctactgg  900
gcggacgcca gcaaagccga ccgtgaactg aactggcgcg taacgcgcac actcgatgaa  960
atggcgcagg acacctggca ctggcagtca cgccatccac agggatatcc cgattaa     1017

SEQ ID NO: 26          moltype = AA  length = 338
FEATURE                Location/Qualifiers
source                 1..338
                       mol_type = protein
                       organism = Homo sapiens
SEQUENCE: 26
MRVLVTGGSG YIGSHTCVQL LQNGHDVIIL DNLCNSKRSV LPVIERLGGK HPTFVEGDIR  60
NEALMTEILH DHAIDTVIHF AGLKAVGESV QKPLEYYDNN VNGTLRLISA MRAANVKNFI  120
FSSSATVYGD QPKIPYVESF PTGTPQSPYG KSKLMVEQIL TDLQKAQPDW SIALLRYFNP  180
VGAHPSGDMG EDPQGIPNNL MPYIAQVAVG RRDSLAIFGN DYPTEDGTGV RDYIHVMDLA  240
DGHVVAMEKL ANKPGVHIYN LGAGVGNSVL DVVNAFSKAC GKPVNYHFAP RREGDLPAYW  300
ADASKADREL NWRVTRTLDE MAQDTWHWQS RHPQGYPD                          338

SEQ ID NO: 27          moltype = DNA  length = 1176
FEATURE                Location/Qualifiers
source                 1..1176
                       mol_type = genomic DNA
                       organism = Homo sapiens
SEQUENCE: 27
atgcaaaaac tcattaactc agtgcaaaac tatgcctggg gcagcaaaac ggcgttgact  60
gaactttatg gtatggaaaa tccgtccagc cagccgatgg ccgagctgtg gatgggcgca  120
catccgaaaa gcagttcacg agtgcagaat gccgccggag atatcgtttc actgcgtgat  180
gtgattgaga gtgataaatc gactctgctc ggagaggccg ttgccaaacg ctttggcgaa  240
ctgcctttcc tgttcaaagt attatgcgca gcacagccac tctccattca ggttcatcca  300
aacaaacaca attctgaaat cggttttgcc aaagaaaatg ccgcaggtat cccgatggat  360
gccgccgagc gtaactataa agatcctaac cacaagccgg agctggtttt tgcgctgacg  420
cctttccttg cgatgaacgc gtttcgtgaa ttttccgaga ttgtctccct actccagccg  480
gtcgcaggtg cacatccggc gattgctcac tttttacaac agcctgatgc cgaacgttta  540
agcgaactgt tcgccagcct gttgaatatg cagggtgaag aaaaatcccg cgcgctggcg  600
attttaaaat cggccctcga tagccagcag ggtgaaccgt ggcaaacgat tcgtttaatt  660
tctgaatttt acccggaaga cagcggtctg ttctccccgc tattgctgaa tgtggtgaaa  720
ttgaaccctg gcgaagcgat gttcctgttc gctgaaacac cgcacgctta cctgcaaggc  780
gtggcgctgg aagtgatggc aaactccgat aacgtgctgc gtgcgggtct gacgcctaaa  840
tacattgata ttccggaact ggttgccaat gtgaaattcg aagccaaacc ggctaaccag  900
ttgttgaccc agccggtgaa acaaggtgca gaactggact tcccgattcc agtggatgat  960
tttgccttct cgctgcatga ccttagtgat aaagaaacca ccattagcca gcagagtgcc  1020
```

```
gccattttgt tctgcgtcga aggcgatgca acgttgtgga aaggttctca gcagttacag  1080
cttaaaccgg gtgaatcagc gtttattgcc gccaacgaat caccggtgac tgtcaaaggc  1140
cacggccgtt tagcgcgtgt ttacaacaag ctgtaa                            1176

SEQ ID NO: 28          moltype = AA  length = 391
FEATURE                Location/Qualifiers
source                 1..391
                       mol_type = protein
                       organism = Homo sapiens
SEQUENCE: 28
MQKLINSVQN YAWGSKTALT ELYGMENPSS QPMAELWMGA HPKSSSRVQN AAGDIVSLRD  60
VIESDKSTLL GEAVAKRFGE LPFLFKVLCA AQPLSIQVHP NKHNSEIGFA KENAAGIPMD  120
AAERNYKDPN HKPELVFALT PFLAMNAFRE FSEIVSLLQP VAGAHPAIAH FLQQPDAERL  180
SELFASLLNM QGEEKSRALA ILKSALDSQQ GEPWQTIRLI SEFYPEDSGL FSPLLLNVVK  240
LNPGEAMFLF AETPHAYLQG VALEVMANSD NVLRAGLTPK YIDIPELVAN VKFEAKPANQ  300
LLTQPVKQGA ELDFPIPVDD FAFSLHDLSD KETTISQQSA AILFCVEGDA TLWKGSQQLQ  360
LKPGESAFIA ANESPVTVKG HGRLARVYNK L                                 391

SEQ ID NO: 29          moltype = DNA  length = 1371
FEATURE                Location/Qualifiers
source                 1..1371
                       mol_type = genomic DNA
                       organism = Homo sapiens
SEQUENCE: 29
atgaaaaaat taacctgctt taaagcctat gatattcgcg ggaaattagg cgaagaactg  60
aatgaagata tcgcctggcg cattggtcgc gcctatggcg aatttctcaa accgaaaacc  120
attgtgttag gcggtgatgt ccgcctcacc agcgaaacct taaaactggc gctggcgaaa  180
ggtttacagg atgcgggcgt tgacgtgctg gatattggta tgtccggcac cgaagagatc  240
tatttcgcca cgttccatct cggcgtggat ggcggcattg aagttaccgc cagccataat  300
ccgatggatt ataacggcat gaagctggtt cgcgaggggg ctcgcccgat cagcggagat  360
accggactgc gcgacgtcca gcgtctggct gaagccaacg actttcctcc cgtcgatgaa  420
accaaacgcg gtcgctatca gcaaatcaac ctgcgtgacg cttacgttga tcacctgttc  480
ggttatatca atgtcaaaaa cctcacgccg ctcaagctgg tgatcaactc cgggaacggc  540
gcagcgggtc cggtggtgga cgccattgaa gcccgcttta aagccctcgg cgcgcccgtg  600
gaattaatca aagtgcacaa cacgccggac ggcaatttcc ccaacggtat tcctaaccca  660
ctactgccgg aatgccgcga cgacacccgc aatgcggtca tcaaacacgg cgcggatatg  720
ggcattgctt ttgatggcga ttttgaccgc tgtttcctgt ttgacgaaaa agggcagttt  780
attgagggct actacattgt cggcctgttg gcagaagcat tcctcgaaaa aaatcccggc  840
gcgaagatca tccacgatcc acgtctctcc tggaacaccg ttgatgtggt gactgccgca  900
ggtggcacgc cggtaatgtc gaaaaccgga cacgccttta ttaaagaacg tatgcgcaag  960
gaagacgcca tctatggtgg cgaaatgagc gcccaccatt acttccgtga tttcgcttac  1020
tgcgacagcg gcatgatccc gtggctgctg gtcgccgaac tggtgtgcct gaaagataaa  1080
acgctgggcg aactggtacg cgaccggatg gcggcgtttc cggcaagcgg tgagatcaac  1140
agcaaactgg cgcaacccgt tgaggcgatt aaccgcgtgg aacagcattt tagccgtgag  1200
gcgctggcgg tggatcgcac cgatggcatc agcatgacct ttgccgactg gcgctttaac  1260
ctgcgcacct ccaataccga accggtggtg cgcctgaatg tggaatcgcg cggtgatgtg  1320
ccgctgatgg aagcgcgaac gcgaactctg ctgacgttgc tgaacgagta a           1371

SEQ ID NO: 30          moltype = AA  length = 456
FEATURE                Location/Qualifiers
source                 1..456
                       mol_type = protein
                       organism = Homo sapiens
SEQUENCE: 30
MKKLTCFKAY DIRGKLGEEL NEDIAWRIGR AYGEFLKPKT IVLGGDVRLT SETLKLALAK  60
GLQDAGVDVL DIGMSGTEEI YFATFHLGVD GGIEVTASHN PMDYNGMKLV REGARPISGD  120
TGLRDVQRLA EANDFPPVDE TKRGRYQQIN LRDAYVDHLF GYINVKNLTP LKLVINSGNG  180
AAGPVVDAIE ARFKALGAPV ELIKVHNTPD GNFPNGIPNP LLPECRDDTR NAVIKHGADM  240
GIAFDGDFDR CFLFDEKGQF IEGYYIVGLL AEAFLEKNPG AKIIHDPRLS WNTVDVVTAA  300
GGTPVMSKTG HAFIKERMRK EDAIYGGEMS AHHYFRDFAY CDSGMIPWLL VAELVCLKDK  360
TLGELVRDRM AAFPASGEIN SKLAQPVEAI NRVEQHFSRE ALAVDRTDGI SMTFADWRFN  420
LRTSNTEPVV RLNVESRGDV PLMEARTRTL LTLLNE                            456

SEQ ID NO: 31          moltype = DNA  length = 1437
FEATURE                Location/Qualifiers
source                 1..1437
                       mol_type = genomic DNA
                       organism = Homo sapiens
SEQUENCE: 31
atggcgcagt cgaaactcta tccagttgtg atggcaggtg gctccggtag ccgcttatgg  60
ccgctttccc gcgtacttta tcccaagcag tttttatgcc tgaaaggcga tctcaccatg  120
ctgcaaacca ccatctgccg cctgaacggc gtggagtgcg aaagcccggt ggtgatttgc  180
aatgagcagc accgctttat tgtcgcggaa cagctgcgtc aactgaacaa acttaccgag  240
aacattattc tcgaaccggc agggcgaaac acggcacctg ccattgcgct ggcggcgctg  300
gcggcaaaac gtcatagccc ggagagcgac ccgttaatgc tggtattggc ggcggatcat  360
gtgattgccg atgaagacgc gttccgtgcc gccgtgcgta atgccatgcc atatgccgaa  420
gcgggcaagc tggtgacctt cggcattgtg ccggatctac cagaaaccgg ttatggctat  480
attcgtcgcg gtgaagtgtc tgcgggtgag caggatatgg tggcctttga agtggcgcag  540
tttgtcgaaa aaccgaatct ggaaaccgct caggcctatg tggcaagcgg cgaatattac  600
```

```
tggaacagcg gtatgttcct gttccgcgcc ggacgctatc tcgaagaact gaaaaaatat  660
cgcccggata tcctcgatgc ctgtgaaaaa gcgatgagcg ccgtcgatcc ggatctcaat  720
tttattcgcg tggatgaaga agcgtttctc gcctgcccgg aagagtcggt ggattacgcg  780
gtcatggaac gtacggcaga tgctgttgtg gtgccgatgg atgcgggctg gagcgatgtt  840
ggctcctggt cttcattatg ggagatcagc gcccacaccg ccgagggcaa cgtttgccac  900
ggcgatgtga ttaatcacaa aactgaaaac agctatgtgt atgctgaatc tggcctggtc  960
accaccgtcg ggtgaaaga tctggtagtg gtgcagacca aagatgcggt gctgattgcc  1020
gaccgtaacg cggtacagga tgtgaaaaaa gtggtcgagc agatcaaagc cgatggtcgc  1080
catgagcatc gggtgcatcg cgaagtgtat cgtccgtggg gcaaatatga ctctatcgac  1140
gcgggcgacc gctaccaggt gaaacgcatc accgtgaaac cgggcgaggg cttgtcggta  1200
cagatgcacc atcaccgcgc ggaacactgg gtggttgtcg cgggaacggc aaaagtcacc  1260
attgatggtg atatcaaact gcttggtgaa aacgagtcca tttatattcc gctgggggcg  1320
acgcattgcc tggaaaaccc ggggaaaatt ccgctcgatt taattgaagt gcgctccggc  1380
tcttatctcg aagaggatga tgtggtgcgt ttcgcggatc gctacggacg ggtgtaa     1437

SEQ ID NO: 32           moltype = AA  length = 478
FEATURE                 Location/Qualifiers
source                  1..478
                        mol_type = protein
                        organism = Homo sapiens
SEQUENCE: 32
MAQSKLYPVV MAGGSGSRLW PLSRVLYPKQ FLCLKGDLTM LQTTICRLNG VECESPVVIC  60
NEQHRFIVAE QLRQLNKLTE NIILEPAGRN TAPAIALAAL AAKRHSPESD PLMLVLAADH  120
VIADEDAFRA AVRNAMPYAE AGKLVTFGIV PDLPETGYGY IRRGEVSAGE QDMVAFEVAQ  180
FVEKPNLETA QAYVASGEYY WNSGMFLFRA GRYLEELKKY RPDILDACEK AMSAVDPDLN  240
FIRVDEEAFL ACPEESVDYA VMERTADAVV VPMDAGWSDV GSWSSLWEIS AHTAEGNVCH  300
GDVINHKTEN SYVYAESGLV TTVGVKDLVV VQTKDAVLIA DRNAVQDVKK VVEQIKADGR  360
HEHRVHREVY RPWGKYDSID AGDRYQVKRI TVKPGEGLSV QMHHHRAEHW VVVAGTAKVT  420
IDGDIKLLGE NESIYIPLGA THCLENPGKI PLDLIEVRSG SYLEEDDVVR FADRYGRV    478

SEQ ID NO: 33           moltype = DNA  length = 1122
FEATURE                 Location/Qualifiers
source                  1..1122
                        mol_type = genomic DNA
                        organism = Homo sapiens
SEQUENCE: 33
atgtcaaaag tcgctctcat caccggtgta accggacaag acggttctta cctggcagag  60
tttctgctgg aaaaaggtta cgaggtgcat ggtattaagc gtcgcgcatc gtcattcaac  120
accgagcgcg tggatcacat ttatcaggat ccgcacacct gcaacccgaa attccatctg  180
cattatggcg acctgagtga tacctctaac ctgacgcgca ttttgcgtga agtacagccg  240
gatgaagtgt acaacctggg cgcaatgagc cacgttgcgg tctcttttga gtcaccagaa  300
tataccgctg acgtcgacgc gatgggtacg ctgcgcctgc tggaggcgat ccgcttcctc  360
ggtctggaaa agaaaaactcg tttctatcag gcttccacct ctgaactgta tggtctggtg  420
caggaaattc cgcagaaaga gaccacgccg ttctacccgc gatctccgta tgcggtcgcc  480
aaactgtacg cctactggat caccgttaac taccgtgaat cctacggcat gtacgcctgt  540
aacggaattc tcttcaacca tgaatccccg cgccgcggcg aaaccttcgt tacccgcaaa  600
atcacccgcg caatcgccaa catcgcccag ggctggagt cgtgcctgta cctcggcaat  660
atggattccc tgcgtgactg gggccacgcc aaagactacg taaaaatgca gtggatgatg  720
ctgcagcagg aacagccgga agatttcgtt atcgcgaccg gcgttcagta ctccgtgcgt  780
cagttcgtgg aaatggcggc agcacagctg ggcatcaaac tgcgctttga aggcacgggc  840
gttgaagaga agggcattgt ggtttccgtc accgggcatg acgcgccggg cgttaaaccg  900
ggtgatgtga ttatcgctgt tgacccgcgt tacttccgtc cggctgaagt tgaaacgctg  960
ctcggcgacc cgaccaaagc gcacgaaaaa ctgggctgga aaccggaaat caccctcaga  1020
gagatggtgt ctgaaatggt ggctaatgac ctcgaagcgg cgaaaaaaca ctctctgctg  1080
aaatctcacg gctacgacgt ggcgatcgcg ctggagtcat aa                    1122

SEQ ID NO: 34           moltype = AA  length = 373
FEATURE                 Location/Qualifiers
source                  1..373
                        mol_type = protein
                        organism = Homo sapiens
SEQUENCE: 34
MSKVALITGV TGQDGSYLAE FLLEKGYEVH GIKRRASSFN TERVDHIYQD PHTCNPKFHL  60
HYGDLSDTSN LTRILREVQP DEVYNLGAMS HVAVSFESPE YTADVDAMGT LRLLEAIRFL  120
GLEKKTRFYQ ASTSELYGLV QEIPQKETTP FYPRSPYAVA KLYAYWITVN YRESYGMYAC  180
NGILFNHESP RRGETFVTRK ITRAIANIAQ GLESCLYLGN MDSLRDWGHA KDYVKMQWMM  240
LQQEQPEDFV IATGVQYSVR QFVEMAAAQL GIKLRFEGTG VEEKGIVVSV TGHDAPGVKP  300
GDVIIAVDPR YFRPAEVETL LGDPTKAHEK LGWKPEITLR EMVSEMVAND LEAAKKHSLL  360
KSHGYDVAIA LES                                                    373

SEQ ID NO: 35           moltype = DNA  length = 966
FEATURE                 Location/Qualifiers
source                  1..966
                        mol_type = genomic DNA
                        organism = Homo sapiens
SEQUENCE: 35
atgagtaaac aacgagtttt tattgctggt catcgcggga tggtcggttc cgccatcaag  60
cgacagctcg aacagcgcgg tgatgtggag ctggtattac gcacccgcga tgaactgaac  120
ctgctggaca gccgcgcggt gcatgatttc tttgccagcg aaagcattga ccaggtctat  180
```

```
ctggcggcgg cgaaagtggg cggcattgtt gccaacaaca cgtatccggc ggatttcatc  240
taccagaaca tgatgattga gagcaacatc attcacgccg cgcatcagaa cgacgtgaac  300
aaactgctgt ttctcggatc gtcctgtatc tacccgaaac tggcaaaaca gccgatggca  360
gaaagcgagt tattgcaggg cacgctggag ccgaccaacg agccttatgc cattgccaaa  420
attgccggga tcaaactgtg cgaatcttac aaccgccagt acggacgcga ttaccgctca  480
gtcatgccga ccaacctgta tggcccgcat gacaacttcc acccgagtaa ttcgcatgtg  540
atcccagcat tgttgcgtcg cttccacgag gcgacggcac agaatgcgcc ggacgttgtg  600
gtatggggca gcggtacacc gatgcgtgaa ttcctgcacg tcgatgatat ggcggcggcc  660
agcattcacg tgatggagct ggcgcacgaa gtctggctgg agaacaccca gccgatgctg  720
tcgcacatta acgtcggtac cggtgttgac tgcactatcc gcgagctggc gcaaaccatc  780
gccaaagtgg tggattacaa aggtcgggtg gtttttgatg ccagcaagcc ggatggtacg  840
ccgcgcaaac tgctggatgt gacgcgcctg catcagcttg gctggtatca cgaaatctca  900
ctggaagcgg ggcttgccag cacttaccag tggttccttg agaatcgaga ccgctttcgg  960
gggtaa                                                              966
```

```
SEQ ID NO: 36           moltype = AA  length = 321
FEATURE                 Location/Qualifiers
source                  1..321
                        mol_type = protein
                        organism = Homo sapiens
SEQUENCE: 36
MSKQRVFIAG HRGMVGSAIK RQLEQRGDVE LVLRTRDELN LLDSRAVHDF FASESIDQVY  60
LAAAKVGGIV ANNTYPADFI YQNMMIESNI IHAAHQNDVN KLLFLGSSCI YPKLAKQPMA  120
ESELLQGTLE PTNEPYAIAK IAGIKLCESY NRQYGRDYRS VMPTNLYGPH DNFHPSNSHV  180
IPALLRRFHE ATAQNAPDVV VWGSGTPMRE FLHVDDMAAA SIHVMELAHE VWLENTQPML  240
SHINVGTGVD CTIRELAQTI AKVVDYKGRV VFDASKPDGT PRKLLDVTRL HQLGWYHEIS  300
LEAGLASTYQ WFLENRDRFR G                                             321
```

```
SEQ ID NO: 37           moltype = DNA  length = 1830
FEATURE                 Location/Qualifiers
source                  1..1830
                        mol_type = genomic DNA
                        organism = Homo sapiens
SEQUENCE: 37
atgtgtggaa ttgttggcgc gatcgcgcaa cgtgatgtag cagaaatcct tcttgaaggt  60
ttacgtcgtc tggaataccg cggatatgac tctgccggtc tggccgttgt tgatgcagaa  120
ggtcatatga cccgcctgcg tcgcctcggt aaagtccaga tgctggcaca ggcagcggaa  180
gaacatcctc tgcatggcgg cactggtatt gctcacactc gctgggcgac ccacggtgaa  240
ccttcagaag tgaatgcgca tccgcatgtt tctgaacaca ttgtggtggt gcataacggc  300
atcatcgaaa accatgaacc gctgcgtgaa gagctaaaag cgcgtggcta taccttcgtt  360
tctgaaaccg acaccgaagt gattgcccat ctggtgaact gggagctgaa acaaggcggg  420
actctgcgtg aggccgttct gcgtgctatc ccgcagctgc gtggtgcgta cggtacagtg  480
atcatggact cccgtcaccc ggataccctg ctggcggcac gttctggtag tccgctggtg  540
attggcctgg ggatgggcga aaactttatc gcttctgacc agctggcgct gttgccggtg  600
acccgtcgct ttatcttcct tgaagagggc gatattgcgg aaatcactcg ccgttcggta  660
aacatcttcg ataaaactgg cgcggaagta aaacgtcagg atatcgaatc caatctgcaa  720
tatgacgcgg gcgataaagg catttaccgt cactacatgc agaaagagat ctacgaacag  780
ccgaacgcga tcaaaaacac ccttaccgga cgcatcagcc acggtcaggt tgatttaagc  840
gagctgggac cgaacgccga cgaactgctg tcgaaggttg agcatattca gatcctcgcc  900
tgtggtactt cttataactc cggtatggtt tcccgctact ggtttgaatc gctagcaggt  960
attccgtgcg acgtcgaaat cgcctctgaa ttccgctatc gcaaatctgc cgtgcgtcgt  1020
aacagcctga tgatcacctt gtcacagtct ggcgaaaccg cggataccct ggctggcctg  1080
cgtctgtcga aagagctggg ttaccttggt tcactggcaa tctgtaacgt tccgggttct  1140
tctctggtgc gcgaatccga tctggcgcta atgaccaacg cgggtacaga aatcggcgtg  1200
gcatccacta aagcattcac cactcagtta actgtgctgt tgatgctggt ggcgaagctg  1260
tctcgcctga aaggtctgga tgcctccatt gaacatgaca tcgtgcatgg tctgcaggcg  1320
ctgccgagcc gtattgagca gatgctgtct caggacaaac gcattgaagc gctggcagaa  1380
gatttctctg acaaacatca cgcgctgttc ctgggccgtg gcgatcagta cccaatcgcg  1440
ctggaaggcg cattgaagtt gaaagagatc tcttacattc acgctgaagc ctacgctgct  1500
ggcgaactga aacacggtcc gctggcgcta attgatgccg atatgccggt tattgttgtt  1560
gcaccgaaca acgaattgct ggaaaaactg aaatccaaca ttgaagaagt tcgcgcgcgt  1620
ggcggtcagt tgtatgtctt cgccgatcag gatgcgggtt ttgtaagtag cgataacatg  1680
cacatcatcg agatgccgca tgtggaagag gtgattgcac cgatcttcta caccgttccg  1740
ctgcagctgc tggcttacca tgtcgcgctg atcaaaggca ccgacgttga ccagccgcgt  1800
aacctggcaa aatcggttac ggttgagtaa                                    1830
```

```
SEQ ID NO: 38           moltype = AA  length = 609
FEATURE                 Location/Qualifiers
source                  1..609
                        mol_type = protein
                        organism = Homo sapiens
SEQUENCE: 38
MCGIVGAIAQ RDVAEILLEG LRRLEYRGYD SAGLAVVDAE GHMTRLRRLG KVQMLAQAAE  60
EHPLHGGTGI AHTRWATHGE PSEVNAHPHV SEHIVVVHNG IIENHEPLRE ELKARGYTFV  120
SETDTEVIAH LVNWELKQGG TLREAVLRAI PQLRGAYGTV IMDSRHPDTL LAARSGSPLV  180
IGLGMGENFI ASDQLALLPV TRRFIFLEEG DIAEITRRSV NIFDKTGAEV KRQDIESNLQ  240
YDAGDKGIYR HYMQKEIYEQ PNAIKNTLTG RISHGQVDLS ELGPNADELL SKVEHIQILA  300
CGTSYNSGMV SRYWFESLAG IPCDVEIASE FRYRKSAVRR NSLMITLSQS GETADTLAGL  360
RLSKELGYLG SLAICNVPGS SLVRESDLAL MTNAGTEIGV ASTKAFTTQL TVLLMLVAKL  420
```

```
SRLKGLDASI EHDIVHGLQA LPSRIEQMLS QDKRIEALAE DFSDKHHALF LGRGDQYPIA  480
LEGALKLKEI SYIHAEAYAA GELKHGPLAL IDADMPVIVV APNNELLEKL KSNIEEVRAR  540
GGQLYVFADQ DAGFVSSDNM HIIEMPHVEE VIAPIFYTVP LQLLAYHVAL IKGTDVDQPR  600
NLAKSVTVE                                                         609

SEQ ID NO: 39          moltype = DNA  length = 1338
FEATURE                Location/Qualifiers
source                 1..1338
                       mol_type = genomic DNA
                       organism = Homo sapiens
SEQUENCE: 39
atgagtaatc gtaaatattt cggtaccgat gggattcgtg gtcgtgtagg ggatgcgccg  60
atcacacctg attttgtgct taagctgggt tgggccgcgg gtaaagtgct ggcgcgccac  120
ggctcccgta agattattat tggtaaagac acgcgtattt ctggctatat gctggagtca  180
gcactggaag cgggtctggc ggcagcgggc ctttccgcac tcttcactgg cccgatgcca  240
acaccggccg tggcttatct gacgcgtacc ttccgcgcag aggccggaat tgtgatatct  300
gcatcgcata acccgttcta cgataatggc attaaattct tctctatcga cggcaccaaa  360
ctgccggatg cggtagaaga ggccatcgaa gcggaaatgg aaaaggagat cagctgcgtt  420
gattcggcag aactgggtaa agccagccgt atcgttgatg ccgcgggtcg ctatatcgag  480
ttttgcaaag ccacgttccc gaacgaactt agcctcagtg aactgaagat tgtggtggat  540
tgtgcaaacg gtgcgactta tcacatcgcg ccgaacgtgc tgcgcgaact gggggcgaac  600
gttatcgcta tcggttgtga gccaaacggt gtaaacatca atgccgaagt gggggctacc  660
gacgttcgcg cgctccaggc tcgtgtgctg gctgaaaaag cggatctcgg tattgccttc  720
gacggcgatg gcgatcgcgt gattatggtt gaccatgaag gcaataaagt cgatggcgat  780
cagatcatgt atatcatcgc gcgtgaaggt cttcgtcagg gccagctgcg tggtggcgct  840
gtgggtacat tgatgagcaa catggggctt gaactggcgc tgaaacagtt aggaattcca  900
tttgcgcgcg cgaaagtggg tgaccgctac gtactggaaa aaatgcagga gaaaggctgg  960
cgtatcggtg cagagaattc cggtcatgtg atcctgctgg ataaaactac taccggtgac  1020
ggcatcgttg ctggcttgca ggtgctggcg gcgatggcac gtaaccatat gagcctgcac  1080
gacctttgca gcggcatgaa aatgttcccg cagattctgg ttaacgtacg ttacaccgca  1140
ggtagcggcg atccacttga gcatgagtca gttaaagccg tgaccgcaga ggttgaagct  1200
gcgctgggca accgtggacg cgtgttgctg cgtaaatccg gcaccgaacc gttaattcgc  1260
gtgatggtgg aaggcgaaga cgaagcgcag gtgactgaat ttgcacaccg catcgccgat  1320
gcagtaaaag ccgtttaa                                               1338

SEQ ID NO: 40          moltype = AA  length = 445
FEATURE                Location/Qualifiers
source                 1..445
                       mol_type = protein
                       organism = Homo sapiens
SEQUENCE: 40
MSNRKYFGTD GIRGRVGDAP ITPDFVLKLG WAAGKVLARH GSRKIIIGKD TRISGYMLES  60
ALEAGLAAAG LSALFTGPMP TPAVAYLTRT FRAEAGIVIS ASHNPFYDNG IKFFSIDGTK  120
LPDAVEEAIE AEMEKEISCV DSAELGKASR IVDAAGRYIE FCKATFPNEL SLSELKIVVD  180
CANGATYHIA PNVLRELGAN VIAIGCEPNG VNINAEVGAT DVRALQARVL AEKADLGIAF  240
DGDGDRVIMV DHEGNKVDGD QIMYIIAREG LRQGQLRGGA VGTLMSNMGL ELALKQLGIP  300
FARAKVGDRY VLEKMQEKGW RIGAENSGHV ILLDKTTTGD GIVAGLQVLA AMARNHMSLH  360
DLCSGMKMFP QILVNVRYTA GSGDPLEHES VKAVTAEVEA ALGNRGRVLL RKSGTEPLIR  420
VMVEGEDEAQ VTEFAHRIAD AVKAV                                       445

SEQ ID NO: 41          moltype = DNA  length = 1371
FEATURE                Location/Qualifiers
source                 1..1371
                       mol_type = genomic DNA
                       organism = Homo sapiens
SEQUENCE: 41
atgttgaata atgctatgag cgtagtgatc cttgccgcag gcaaaggcac gcgcatgtat  60
tccgatcttc cgaaagtgct gcataccctt gccgggaaag cgatggttca gcatgtcatt  120
gatgctgcga atgaattagg cgcagcgcac gttcacctgg tgtacggtca cggcggcgat  180
ctgctaaaac aggcgctgaa agacgacaac cttaactggg tgcttcaggc agagcagctg  240
ggtacgggtc atgcaatgca gcaggccgca cctttctttg ccgatgatga agacatttta  300
atgctctacg gcgacgtgcc gctgatctct gtcgaaacac tccagcgtct gcgtgatgct  360
aaaccgcagg gtggcattgg tctgctgacg gtgaaactgg atgatccgac cggttatgga  420
cgtatcaccc gtgaaaacgg caaagttacc ggcattgttg agcacaaaga tgccaccgac  480
gagcagcgtc agattcagga gatcaacacc ggcattctga ttgccaacgg cgcagatatg  540
aaacgctggc tggcgaagct gaccaacaat aatgctcagg gcgaatacta catcaccgac  600
attattgcgc tggcgtatca ggaagggcgt gaaatcgtcg ccgttcatcc gcaacgttta  660
agcgaagtag aaggcgtgaa taaccgcctg caactctccc gtctggagcg tgtttatcag  720
tccgaacagg ctgaaaaact gctgttagca ggcgttatgc tgcgcgatcc agcgcgtttt  780
gatctgcgtg gtacgctaac tcacgggcgc gatgttgaaa ttgatactaa cgttatcatc  840
gagggcaacg tgactctcgg tcatcgcgtg aaaattggca ccggttgcgt gattaaaaac  900
agcgtgattg gcgatgattg cgaaatcagt ccgtataccg ttgtggaaga tgcgaatctg  960
gcagcggcct gtaccattgg cccgtttgcc cgtttgcgtc ctggtgctga gttgctggaa  1020
ggtgctcacg tcggtaactt cgttgagatg aaaaaagcgc gtctgggtaa aggctcgaaa  1080
gctggtcatc tgacttacct gggcgatgcg gaaattggcg ataacgttaa catcggcgcg  1140
ggaaccatta cctgcaacta cgatggtgcg aataaattta agaccattat cggcgacgat  1200
gtgtttgttg gttccgacac tcagctggtg gccccggtaa cagtaggcaa aggcgcgacc  1260
attgctgcgg gtacaactgt gacgcgtaat gtcggcgaaa atgcattagc tatcagccgt  1320
gtgccgcaga ctcagaaaga aggctggcgt cgtccggtaa agaaaaagtg a          1371
```

```
SEQ ID NO: 42          moltype = AA  length = 456
FEATURE                Location/Qualifiers
source                 1..456
                       mol_type = protein
                       organism = Homo sapiens
SEQUENCE: 42
MLNNAMSVVI LAAGKGTRMY SDLPKVLHTL AGKAMVQHVI DAANELGAAH VHLVYGHGGD  60
LLKQALKDDN LNWVLQAEQL GTGHAMQQAA PFFADDEDIL MLYGDVPLIS VETLQRLRDA  120
KPQGGIGLLT VKLDDPTGYG RITRENGKVT GIVEHKDATD EQRQIQEINT GILIANGADM  180
KRWLAKLTNN NAQGEYYITD IIALAYQEGR EIVAVHPQRL SEVEGVNNRL QLSRLERVYQ  240
SEQAEKLLLA GVMLRDPARF DLRGTLTHGR DVEIDTNVII EGNVTLGHRV KIGTGCVIKN  300
SVIGDDCEIS PYTVVEDANL AAACTIGPFA RLRPGAELLE GAHVGNFVEM KKARLGKGSK  360
AGHLTYLGDA EIGDNVNIGA GTITCNYDGA NKFKTIIGDD VFVGSDTQLV APVTVGKGAT  420
IAAGTTVTRN VGENALAISR VPQTQKEGWR RPVKKK                            456

SEQ ID NO: 43          moltype = DNA  length = 2169
FEATURE                Location/Qualifiers
source                 1..2169
                       mol_type = genomic DNA
                       organism = Homo sapiens
SEQUENCE: 43
atggagaaga acgggaacaa ccgaaagctc cgggtttgcg ttgccacctg caaccgagct  60
gactactcca aactggcccc gatcatgttc ggcatcaaga cagagcccgc gttctttgag  120
ttggacgtgg tggtgctcgg ctcccacctg attgacgact atggaaacac ataccgcatg  180
attgagcaag atgactttga cattaacacc aggctcccaca cgattgttag aggggaagat  240
gaagcggcca tggtagagtc ggtaggccta gcgctcgtga agctaccgga cgtcctcaat  300
cgcctgaagc ccgacatcat gattgttcac ggagatcgat ttgacgccct tgctctggct  360
acgtctgctg ccttgatgaa catccgcatc cttcacattg aaggaggcga ggtcagcggg  420
accattgatg actctatcag acacgccata acaaaactgg ctcactacca tgtgtgctgc  480
actagaagtg cagagcagca cctgatctct atgtgcgagg accacgaccg catcctgttg  540
gcaggctgcc cttcctatga caaactgctc tccgccaaga acaaagacta tatgagcatc  600
attcggatgt ggctaggcga tgatgtaaaa tgtaaggatt acatcgttgc cctgcagcat  660
cccgtgacca ctgacattaa gcattccata aagatgtttg agctaacact ggatgccctg  720
atctcgttta acaagaggac cctagttctg tttccaaata tcgatgcagg cagcaaggag  780
atggttcgag tgatgcggaa gaagggcatc gagcatcacc ccaatttccg tgcagtcaag  840
cacgtcccgt ttgaccagtt catacagctg gtcgcccacg ctggctgcat gattgggaat  900
agcagctgcg gcgtgcgaga ggttggcgct ttcggaacac ccgtgatcaa cctgggcaca  960
aggcagatag gaagagaaac cggggagaat gttcttcatg tcagggatgc tgacacccaa  1020
gataaaatat tgcaagcact acacctccag ttcggcaaac agtacccttg ctcaaagata  1080
tatggggatg ggaatgctgt tccaaggatt ttaaagtttc tcaaatccat tgaccttcaa  1140
gagccactac agaagaaatt ctgcttcccc cctgtaaagg agaacatctc tcaagacatt  1200
gaccacatcc tggaaactct gagtgccttg gctgttgatc ttggcgggac aaacctgagg  1260
gtggcaatag ttagcatgaa gggtgaaatc gttaagaagt acactcagtt caaccctaaa  1320
acctatgaag aaaggattag tttaatcctg cagatgtgtg tggaagctgc cgcggaagct  1380
gtgaaactca attgcagaat actgggagta ggcatctcca caggtggccg cgtgaatccc  1440
caggaaggag ttgtgctgca ttcaaccaag ctgatccagg aatggaactc cgtggacctc  1500
aggacacccc tctccgacac cctgcatctc cccgtgtggg tggacaatga cggcaactgt  1560
gccgccatgg cagagaggaa gttcggccaa ggaaaaggac aggagaactt cgtgacgctc  1620
atcacgggga cagggatcgg tggggggatc atccaccagc acgaactgat ccacggcagc  1680
tccttctgcg cggcggagct cggccatctc gtggtgtccc tggacggtcc tgactgctcc  1740
tgtggaagcc atgggtgcat cgaagcgtac gcctctggaa tggccttgca gagggaagca  1800
aagaaactcc atgatgagga cctgctcttg gtggaaggga tgtcagtacc aaaagacgaa  1860
gctgtgggtg ccctccatct catccaggct gccaagctgg gcaacgtgaa ggcccagagc  1920
atcttacgaa cagctggaac tgctttggga cttggggttg tgaacatcct ccacactatg  1980
aatccttccc tggtgatcct gtctggagtc ctggccagtc actacatcca catcgtcaag  2040
gacgtcatcc gccagcaagc cttgtcctcc gtgcaggatg tggacgtggt ggtgtcagac  2100
ttggtggacc cggccctgct tggcgcagcc agcatggttc tggactacac aacgcgcagg  2160
atacactag                                                         2169

SEQ ID NO: 44          moltype = AA  length = 722
FEATURE                Location/Qualifiers
source                 1..722
                       mol_type = protein
                       organism = Homo sapiens
SEQUENCE: 44
MEKNGNNRKL RVCVATCNRA DYSKLAPIMF GIKTEPAFFE LDVVVLGSHL IDDYGNTYRM  60
IEQDDFDINT RLHTIVRGED EAAMVESVGL ALVKLPDVLN RLKPDIMIVH GDRFDALALA  120
TSAALMNIRI LHIEGGEVSG TIDDSIRHAI TKLAHYHVCC TRSAEQHLIS MCEDHDRILL  180
AGCPSYDKLL SAKNKDYMSI IRMWLGDDVK CKDYIVALQH PVTTDIKHSI KMFELTLDAL  240
ISFNKRTLVL FPNIDAGSKE MVRVMRKKGI EHHPNFRAVK HVPFDQFIQL VAHAGCMIGN  300
SSCGVREVGA FGTPVINLGT RQIGRETGEN VLHVRDADTQ DKILQALHLQ FGKQYPCSKI  360
YGDGNAVPRI LKFLKSIDLQ EPLQKKFCFP PVKENISQDI DHILETLSAL AVDLGGTNLR  420
VAIVSMKGEI VKKYTQFNPK TYEERISLIL QMCVEAAAEA VKLNCRILGV GISTGGRVNP  480
QEGVVLHSTK LIQEWNSVDL RTPLSDTLHL PVWVDNDGNC AAMAERKFGQ GKGQENFVTL  540
ITGTGIGGGI IHQHELIHGS SFCAAELGHL VVSLDGPDCS CGSHGCIEAY ASGMALQREA  600
KKLHDEDLLL VEGMSVPKDE AVGALHLIQA AKLGNVKAQS ILRTAGTALG LGVVNILHTM  660
NPSLVILSGV LASHYIHIVK DVIRQQALSS VQDVDVVVSD LVDPALLGAA SMVLDYTTRR  720
IH                                                                722
```

```
SEQ ID NO: 45          moltype = DNA  length = 1080
FEATURE                Location/Qualifiers
source                 1..1080
                       mol_type = genomic DNA
                       organism = Homo sapiens
SEQUENCE: 45
atgccgctgg agctggagct gtgtcccggg cgctgggtgg gaggtcaaca cccgtgcttc  60
atcattgccg agatcggcca gaaccaccag ggcgacctgg acgtagccaa gcgcatgatc  120
cgcatggcca aggagtgtgg ggctgattgt gctaagttcc agaagagtga gctagaattt  180
aagtttaatc ggaaagcctt ggagaggcca tacacctcga agcattcctg gggaaaaacg  240
tacggggagc acaaacgaca tctggagttc agccatgacc agtacaggga gctgcagagg  300
tacgccgagg aggttgggat cttcttcact gcctctggca tggatgagat ggcagttgaa  360
tttctgcatg aactgaatgt tccatttttc aaagttggat ctggagacac taataatttt  420
ccttatctgg aaaagacagc caaaaaaggt cgcccaatgg tgatctccag tgggatgcag  480
tcaatggaca ccatgaagca agtttatcag atcgtgaagc ccctcaaccc caacttctgc  540
ttcttgcagt gtaccagcgc atacccgctc cagcctgagg acgtcaacct gcgggtcatc  600
tcggaatatc agaagctctt tcctgacatt cccatagggt attctgggca tgaaacaggc  660
atagcgatat ctgtggccgc agtggctctg gggggccaagg tgttggaacg tcacataact  720
ttggacaaga cctggaaggg gagtgaccac tcggcctcgc tggagcctgg agaactggcc  780
gagctggtgc ggtcagtgcg tcttgtggag cgtgccctgg gctccccaac caagcagctg  840
ctgccctgtg agatggcctg caatgagaag ctgggcaagt ctgtggtggc caaagtgaaa  900
attccggaag gcaccattct aacaatggac atgctcaccg tgaaggtggg tgagcccaaa  960
ggctatcctc ctgaggacat ctttaatcta gtgggcaaga aggtcctggt cactgttgaa  1020
gaggatgaca ccatcatgga agaattggta gataatcatg gcaaaaaaat caagtcttaa  1080

SEQ ID NO: 46          moltype = AA  length = 359
FEATURE                Location/Qualifiers
source                 1..359
                       mol_type = protein
                       organism = Homo sapiens
SEQUENCE: 46
MPLELELCPG RWVGGQHPCF IIAEIGQNHQ GDLDVAKRMI RMAKECGADC AKFQKSELEF  60
KFNRKALERP YTSKHSWGKT YGEHKRHLEF SHDQYRELQR YAEEVGIFFT ASGMDEMAVE  120
FLHELNVPFF KVGSGDTNNF PYLEKTAKKG RPMVISSGMQ SMDTMKQVYQ IVKPLNPNFC  180
FLQCTSAYPL QPEDVNLRVI SEYQKLFPDI PIGYSGHETG IAISVAAVAL GAKVLERHIT  240
LDKTWKGSDH SASLEPGELA ELVRSVRLVE RALGSPTKQL LPCEMACNEK LGKSVVAKVK  300
IPEGTILTMD MLTVKVGEPK GYPPEDIFNL VGKKVLVTVE EDDTIMEELV DNHGKKIKS   359

SEQ ID NO: 47          moltype = DNA  length = 747
FEATURE                Location/Qualifiers
source                 1..747
                       mol_type = genomic DNA
                       organism = Homo sapiens
SEQUENCE: 47
atggggctga gccgcgtgcg ggcggttttc tttgacttgg acaacactct catcgacacg  60
gccggggcga gcaggagagg catgttggag gtgataaaac tcttacaatc aaaataccat  120
tataaagaag aggctgaaat catctgtgat aaagttcaag ttaaactcag caaggaatgt  180
tttcatcctt acaatacatg cattactgat ttaaggactt cacattggga agaagcaatc  240
caggaaacaa aaggtggtgc agccaataga aaattggctg aagaatgtta tttcctttgg  300
aaatctacac gtttacagca catgacacta gcagaagatg tcaaagccat gcttactgaa  360
cttcgaaagg aggtccgcct acttctatta acgaatgggg acagacagac ccagagggag  420
aagattgagg cttgtgcctg tcagtcctat tttgacgctg ttgttgtagg tggagagcag  480
agagaggaga aaccagcacc gtccatattt tattactgct gcaatcttct cggagtacaa  540
cctggggact gtgtgatggt cggtgacaca ttagaaaccg acatccaagg aggcctcaat  600
gcaggattga aagcaacagt ctggatcaat aaaaatggaa tagtgccact gaagtcctcc  660
ccagttccgc attacatggt ttcttctgtg ctagagttac ctgctctctt acaaagtata  720
gactgcaaag tcagtatgtc cacttaa                                    747

SEQ ID NO: 48          moltype = AA  length = 248
FEATURE                Location/Qualifiers
source                 1..248
                       mol_type = protein
                       organism = Homo sapiens
SEQUENCE: 48
MGLSRVRAVF FDLDNTLIDT AGASRRGMLE VIKLLQSKYH YKEEAEIICD KVQVKLSKEC  60
FHPYNTCITD LRTSHWEEAI QETKGGAANR KLAEECYFLW KSTRLQHMTL AEDVKAMLTE  120
LRKEVRLLLL TNGDRQTQRE KIEACACQSY FDAVVVGGEQ REEKPAPSIF YYCCNLLGVQ  180
PGDCVMVGDT LETDIQGGLN AGLKATVWIN KNGIVPLKSS PVPHYMVSSV LELPALLQSI  240
DCKVSMST                                                         248

SEQ ID NO: 49          moltype = DNA  length = 1305
FEATURE                Location/Qualifiers
source                 1..1305
                       mol_type = genomic DNA
                       organism = Homo sapiens
SEQUENCE: 49
atggactcgg tggagaaggg tgctgctaca tcagtgtcca acccgcgtgg acgaccatcc  60
cgaggccggc ctcctaagct gcagcgaaac tctcgcggcg gccagggccg aggtgtggag  120
```

-continued

```
aagccccgc acctggcagc cctaattctg gcccggggag gcagcaaagg catcccccctg  180
aagaacatta agcacctggc gggggtcccg ctcattggct gggtcctgcg tgcggccctg  240
gattcagggg ccttccagag tgtatgggtt tcgacagacc atgatgaaat tgagaatgtg  300
gccaaacaat ttggtgcaca agttcatcga agaagttctg aagtttcaaa agacagctct  360
acctcactag atgccatcat agaatttctt aattatcata atgaggttga cattgtagga  420
aatattcaag ctacttctcc atgtttacat cctactgatc ttcaaaaagt tgcagaaatg  480
attcgagaag aaggatatga ttctgttttc tctgttgtga ggcgccatca gtttcgatgg  540
agtgaaattc agaaaggagt tcgtgaagtg accgaacctc tgaatttaaa tccagctaaa  600
cggcctcgtc gacaagactg ggatggagaa ttatatgaaa atggctcatt ttattttgct  660
aaaagacatt tgatagagat gggttacttg cagggtggaa aaatggcata ctacgaaatg  720
cgagctgaac atagtgtgga tatagatgtg gatattgatt ggcctattgc agagcaaaga  780
gtattaagat atggctattt tggcaaagag aagcttaagg aaataaaact tttggtttgc  840
aatattgatg gatgtctcac caatggccac atttatgtat caggtgacca aaaagaaata  900
atatcttatg atgtaaaaga tgctattggg ataagtttat taaagaaaag tggtattgag  960
gtgaggctaa tctcagaaag ggcctgttca aagcagacgc tgtcatcttt aaaactggat  1020
tgcaaaatgg aagtcagtgt atcagacaag ctagcagttg tagatgaatg gagaaaagaa  1080
atgggcctgt gctggaaaga agtggcatat cttggaaatg aagtgtctga tgaagagtgc  1140
ttgaagagag tgggcctaag tggcgctcct gctgatgcct gttctactgc ccagaaggct  1200
gttggataca tttgcaaatg taatggtggc cgtggtgcca tccgagaatt tgcagagcac  1260
atttgcctac taatggaaaa ggttaataat tcatgccaaa aatag                    1305

SEQ ID NO: 50          moltype = AA  length = 434
FEATURE                Location/Qualifiers
source                 1..434
                       mol_type = protein
                       organism = Homo sapiens
SEQUENCE: 50
MDSVEKGAAT SVSNPRGRPS RGRPPKLQRN SRGGQGRGVE KPPHLAALIL ARGGSKGIPL  60
KNIKHLAGVP LIGWVLRAAL DSGAFQSVWV STDHDEIENV AKQFGAQVHR RSSEVSKDSS  120
TSLDAIIEFL NYHNEVDIVG NIQATSPCLH PTDLQKVAEM IREEGYDSVF SVVRRHQFRW  180
SEIQKGVREV TEPLNLNPAK RPRRQDWDGE LYENGSFYFA KRHLIEMGYL QGGKMAYYEM  240
RAEHSVDIDV DIDWPIAEQR VLRYGYFGKE KLKEIKLLVC NIDGCLTNGH IYVSGDQKEI  300
ISYDVKDAIG ISLLKKSGIE VRLISERACS KQTLSSLKLD CKMEVSVSDK LAVVDEWRKE  360
MGLCWKEVAY LGNEVSDEEC LKRVGLSGAP ADACSTAQKA VGYICKCNGG RGAIREFAEH  420
ICLLMEKVNN SCQK                                                      434
```